US008372092B2

(12) United States Patent
Gabel et al.

(10) Patent No.: US 8,372,092 B2
(45) Date of Patent: Feb. 12, 2013

(54) APPLICATOR INSTRUMENTS HAVING PROTECTIVE CARRIERS FOR HEMOSTATS AND METHODS THEREFOR

(75) Inventors: Jonathan Gabel, Randolph, NJ (US); Jason C. Livingston, Scotch Plains, NJ (US); Dwayne Looney, Flemington, NJ (US); Michael E. Guglielmo, Aberdeen, NJ (US); Greg R. Furnish, Louisville, KY (US); John Miser, Crestwood, KY (US)

(73) Assignee: Ethicon, Inc., Somerville, NJ (US)

( * ) Notice: Subject to any disclaimer, the term of this patent is extended or adjusted under 35 U.S.C. 154(b) by 499 days.

(21) Appl. No.: 12/049,869

(22) Filed: Mar. 17, 2008

(65) Prior Publication Data

US 2009/0234380 A1  Sep. 17, 2009

(51) Int. Cl.
*A61B 17/08* (2006.01)
(52) U.S. Cl. ......... 606/151; 606/191; 606/192; 606/213
(58) Field of Classification Search .................. 606/192, 606/190, 191, 194, 195, 198, 151–156, 213–217; 604/103.05, 15–17, 57–64
See application file for complete search history.

(56) References Cited

U.S. PATENT DOCUMENTS

| | | |
|---|---|---|
| 3,760,808 A | 9/1973 | Bleuer |
| 3,857,395 A | 12/1974 | Johnson et al. |
| 4,900,303 A | 2/1990 | Lemelson |
| 5,147,374 A | 9/1992 | Fernandez |
| 5,176,692 A | 1/1993 | Wilk et al. |
| 5,281,197 A * | 1/1994 | Arias et al. ...................... 604/57 |
| 5,395,383 A | 3/1995 | Adams et al. |
| 5,397,332 A * | 3/1995 | Kammerer et al. ........... 606/151 |
| 5,405,360 A | 4/1995 | Tovey |
| 5,419,765 A * | 5/1995 | Weldon et al. ............. 604/99.02 |
| 5,626,601 A * | 5/1997 | Gershony et al. ............. 606/194 |
| 5,645,566 A | 7/1997 | Brenneman et al. |

(Continued)

FOREIGN PATENT DOCUMENTS

| | | |
|---|---|---|
| EP | 0948932 | 10/1999 |
| EP | 2002779 | 12/2008 |

(Continued)

OTHER PUBLICATIONS

International Search Report re: PCT/US2009/037270 dated Oct. 7, 2009.

(Continued)

*Primary Examiner* — Gary Jackson
*Assistant Examiner* — Katrina Stransky
(74) *Attorney, Agent, or Firm* — David R. Crichton

(57) ABSTRACT

An instrument for controlling bleeding includes an outer shaft, an intermediate shaft telescopically received within a central lumen of the outer shaft, and an inner shaft telescopically received within a central lumen of the intermediate shaft, the inner shaft having a proximal end and a distal end that extends distally from the intermediate shaft. The instrument includes a hemostat disposed at the distal end of the inner shaft, and a fluid-resistant element connected to the distal end of the outer shaft and surrounding the hemostat. The fluid-resistant element has a breakable, fluid-resistant seal at a distal end thereof that protects the hemostat from fluids until the hemostat is delivered and deployed onto tissue. In one embodiment, the instrument includes an inflatable balloon to deploy and tamponade the hemostat.

27 Claims, 47 Drawing Sheets

U.S. PATENT DOCUMENTS

| | | | |
|---|---|---|---|
| 5,653,726 A | 8/1997 | Kieturakis | |
| 5,692,642 A * | 12/1997 | Brattesani | 222/1 |
| 6,027,471 A | 2/2000 | Fallon et al. | |
| 6,039,721 A | 3/2000 | Johnson et al. | |
| 6,156,045 A | 12/2000 | Ulbrich et al. | |
| 6,251,093 B1 | 6/2001 | Valley et al. | |
| 6,475,177 B1 | 11/2002 | Suzuki | |
| 6,613,070 B2 * | 9/2003 | Redmond et al. | 606/213 |
| 6,695,856 B2 | 2/2004 | Kieturakis et al. | |
| 6,706,051 B2 | 3/2004 | Hudson et al. | |
| 6,764,497 B2 | 7/2004 | Fogarty et al. | |
| 6,780,183 B2 | 8/2004 | Jimenez, Jr. et al. | |
| 6,989,018 B2 * | 1/2006 | Fogarty et al. | 606/190 |
| 7,018,392 B2 | 3/2006 | Hudson et al. | |
| 7,166,133 B2 | 1/2007 | Evans et al. | |
| 7,175,646 B2 | 2/2007 | Brenneman et al. | |
| 7,192,436 B2 | 3/2007 | Sing et al. | |
| 7,331,979 B2 * | 2/2008 | Khosravi et al. | 606/213 |
| 7,789,893 B2 | 9/2010 | Drasler et al. | |
| 2003/0040705 A1 | 2/2003 | Dorros et al. | |
| 2004/0006305 A1 * | 1/2004 | Hebert et al. | 604/96.01 |
| 2004/0019323 A1 | 1/2004 | Carter et al. | |
| 2004/0249342 A1 | 12/2004 | Khosravi et al. | |
| 2004/0267307 A1 * | 12/2004 | Bagaoisan et al. | 606/213 |
| 2004/0267308 A1 | 12/2004 | Bagaoisan et al. | |
| 2005/0113858 A1 | 5/2005 | Deutsch | |
| 2005/0149099 A1 | 7/2005 | Yamano et al. | |
| 2005/0149117 A1 | 7/2005 | Khosravi et al. | |
| 2005/0155608 A1 | 7/2005 | Pavcnik et al. | |
| 2005/0222605 A1 | 10/2005 | Greenhalgh et al. | |
| 2005/0234499 A1 | 10/2005 | Olson et al. | |
| 2005/0245876 A1 | 11/2005 | Khosravi et al. | |
| 2006/0034930 A1 | 2/2006 | Khosravi et al. | |
| 2007/0021774 A1 | 1/2007 | Hogendijk | |
| 2007/0088380 A1 | 4/2007 | Hirszowicz et al. | |
| 2007/0162067 A1 | 7/2007 | Lunsford et al. | |
| 2007/0173785 A1 | 7/2007 | Ostroot | |
| 2007/0213670 A1 | 9/2007 | Gabel | |
| 2007/0255306 A1 | 11/2007 | Conlon et al. | |
| 2007/0260179 A1 | 11/2007 | Sholev et al. | |
| 2008/0086083 A1 | 4/2008 | Towler | |
| 2011/0066137 A1 * | 3/2011 | Parks et al. | 604/515 |

FOREIGN PATENT DOCUMENTS

| | | |
|---|---|---|
| GB | 651524 | 4/1951 |
| JP | 10-328306 | 12/1998 |
| NL | 1016743 | 12/2001 |
| WO | WO 01/76678 | 10/2001 |
| WO | WO 2007/004221 | 1/2007 |
| WO | WO 2009079607 A1 * | 6/2009 |

OTHER PUBLICATIONS

International Search Report re: PCT/US2009/037276 dated Oct. 7, 2009.

International Search Report re: PCT/US2009/038218 dated Jun. 17, 2009.

* cited by examiner

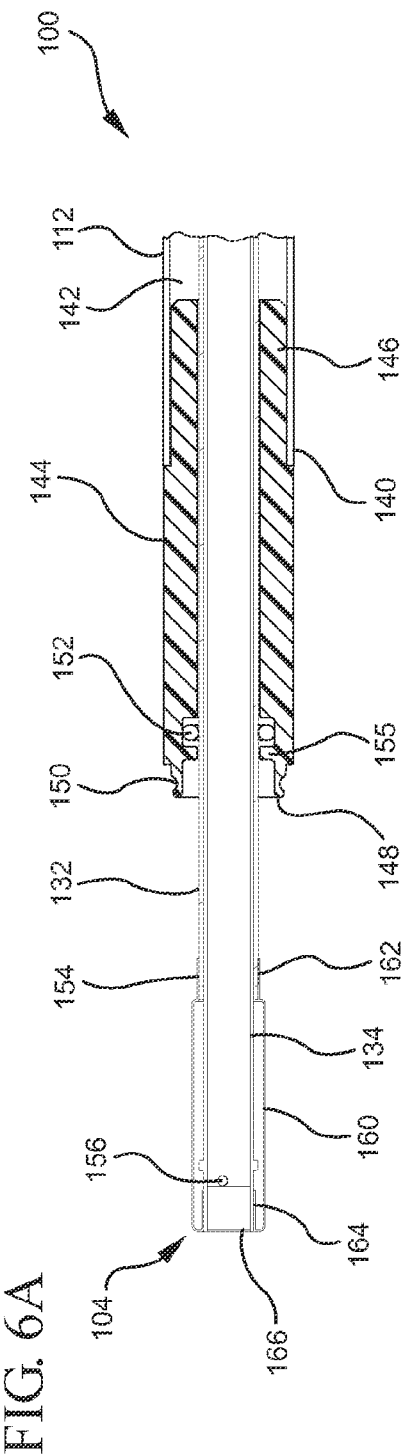
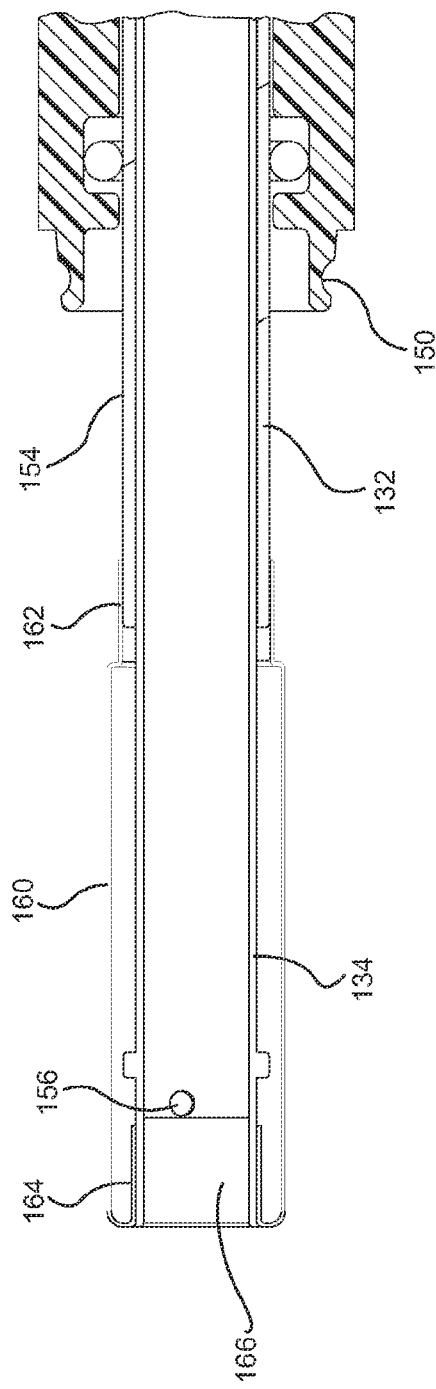
FIG. 6A
FIG. 6B

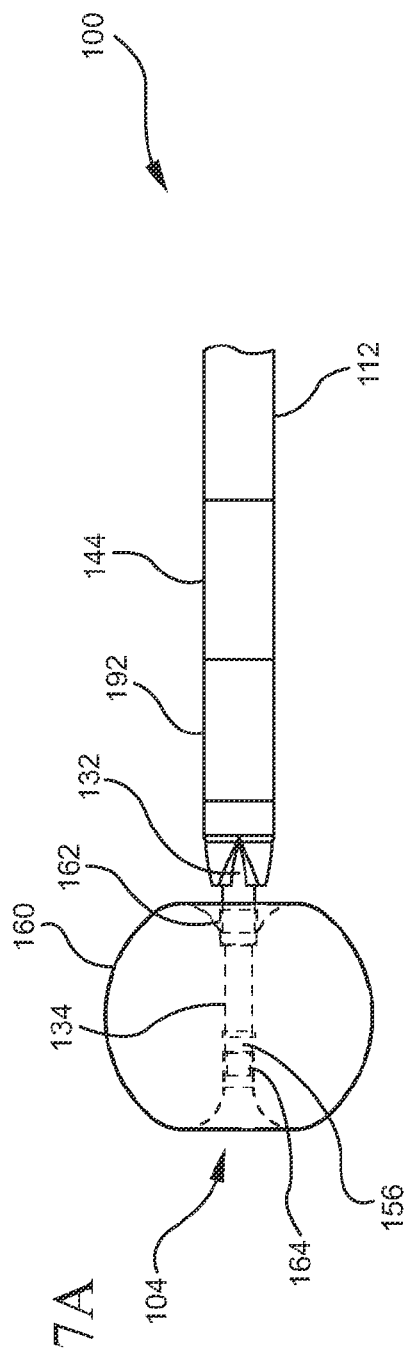
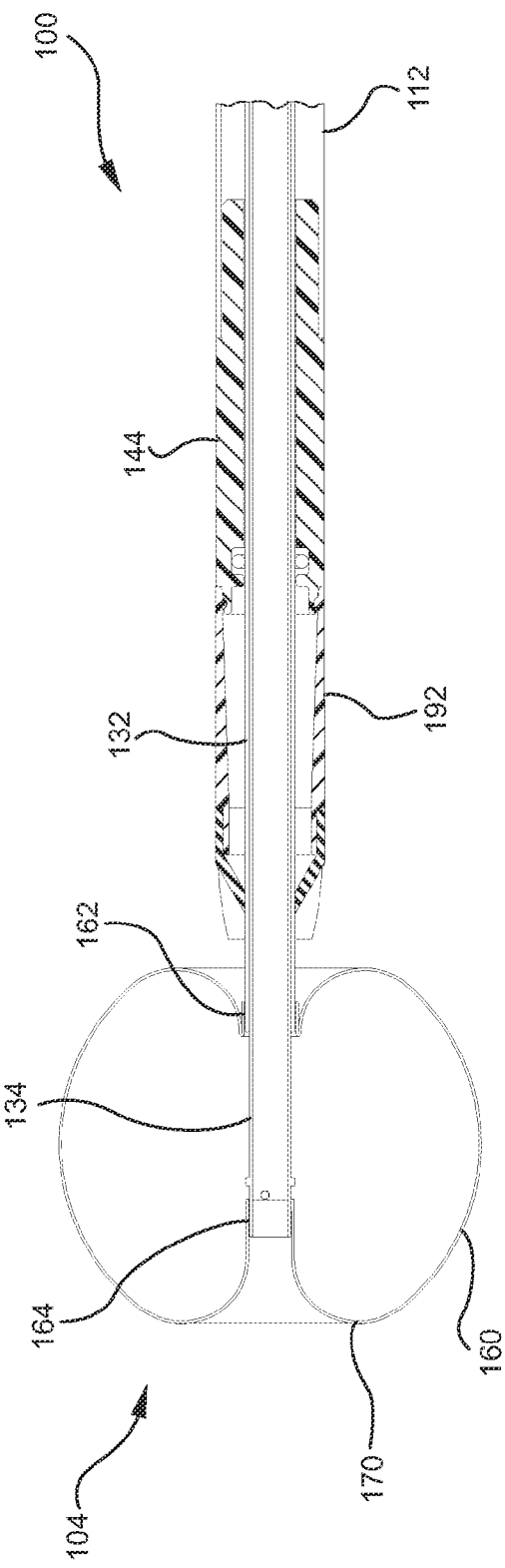
FIG. 7A
FIG. 7A-1

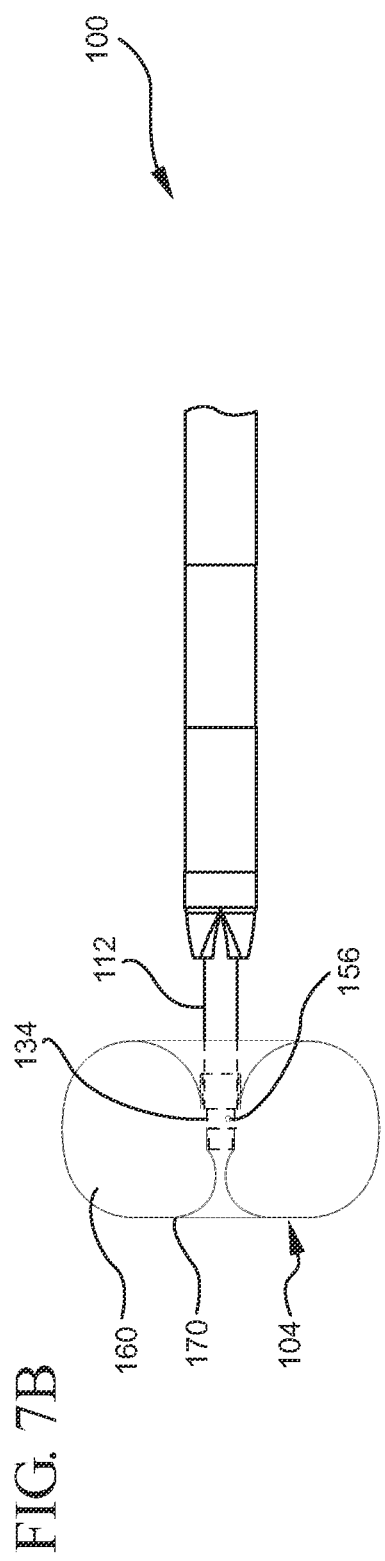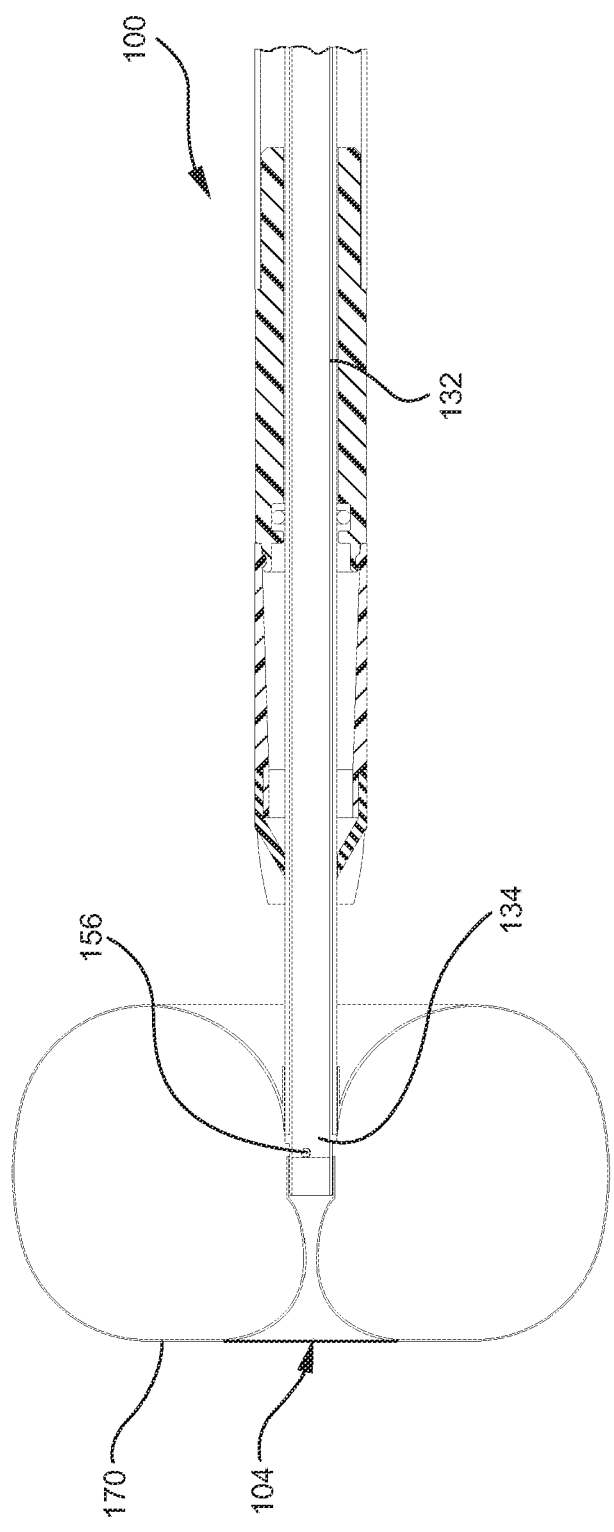

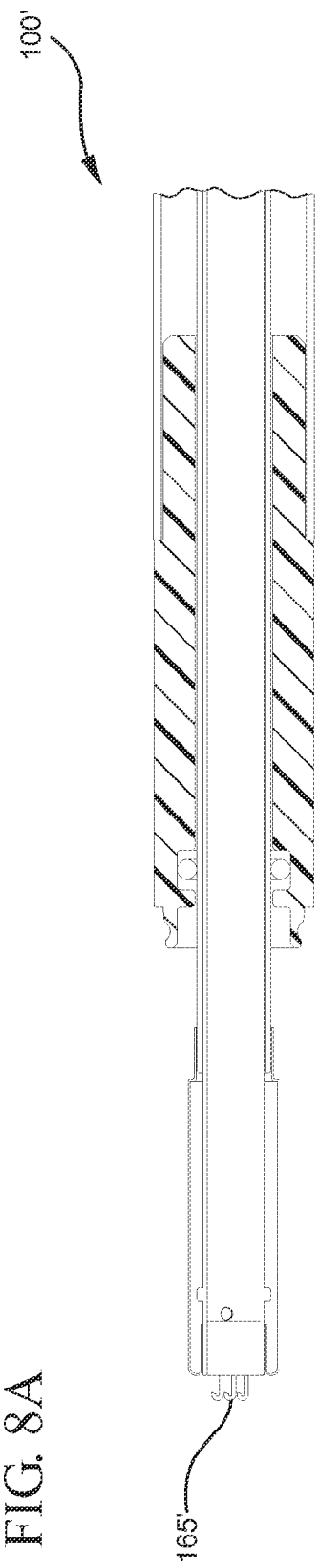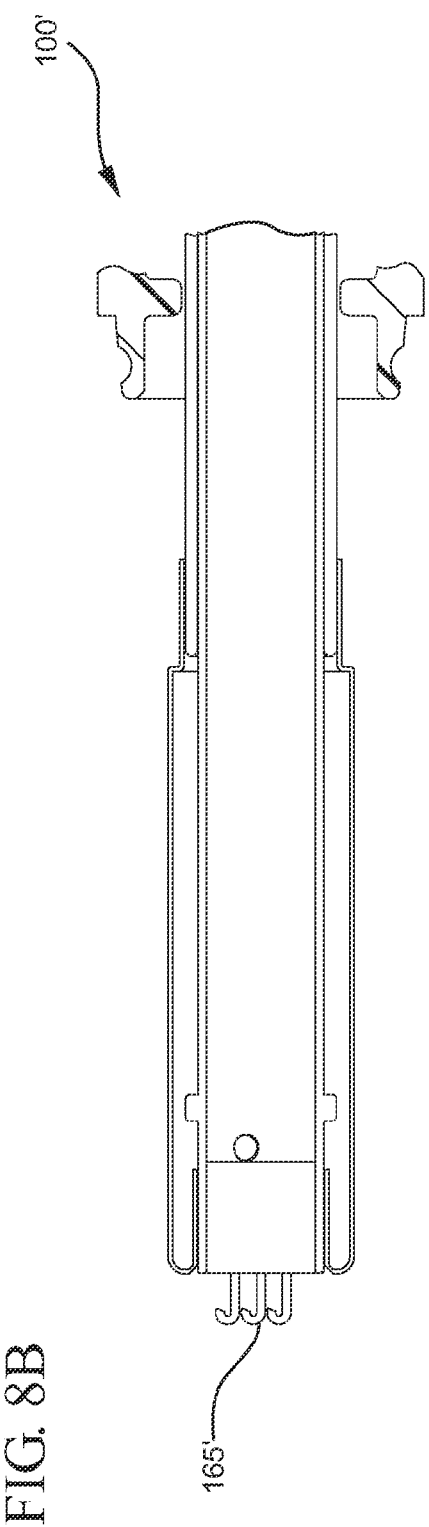
FIG. 8A
FIG. 8B

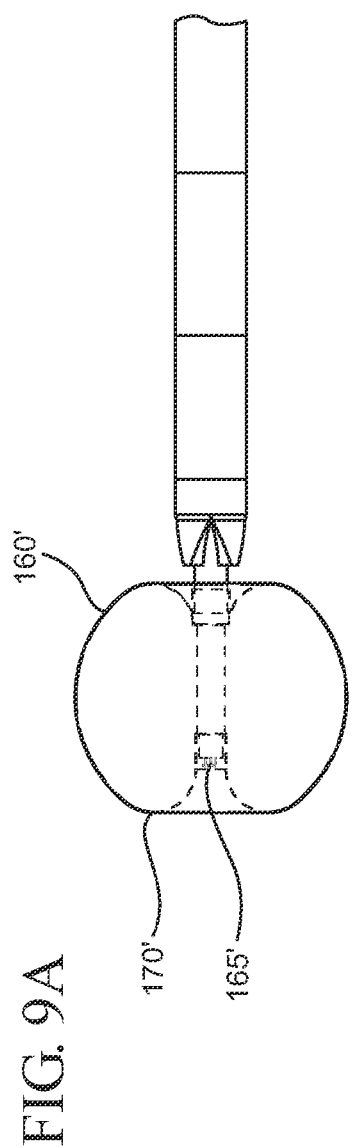
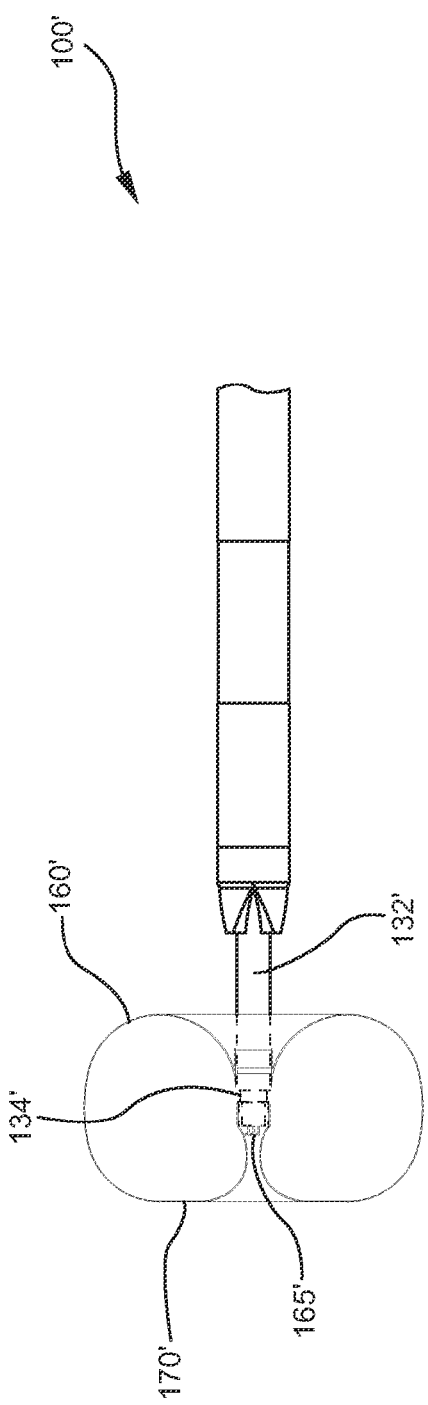
FIG. 9A
FIG. 9B

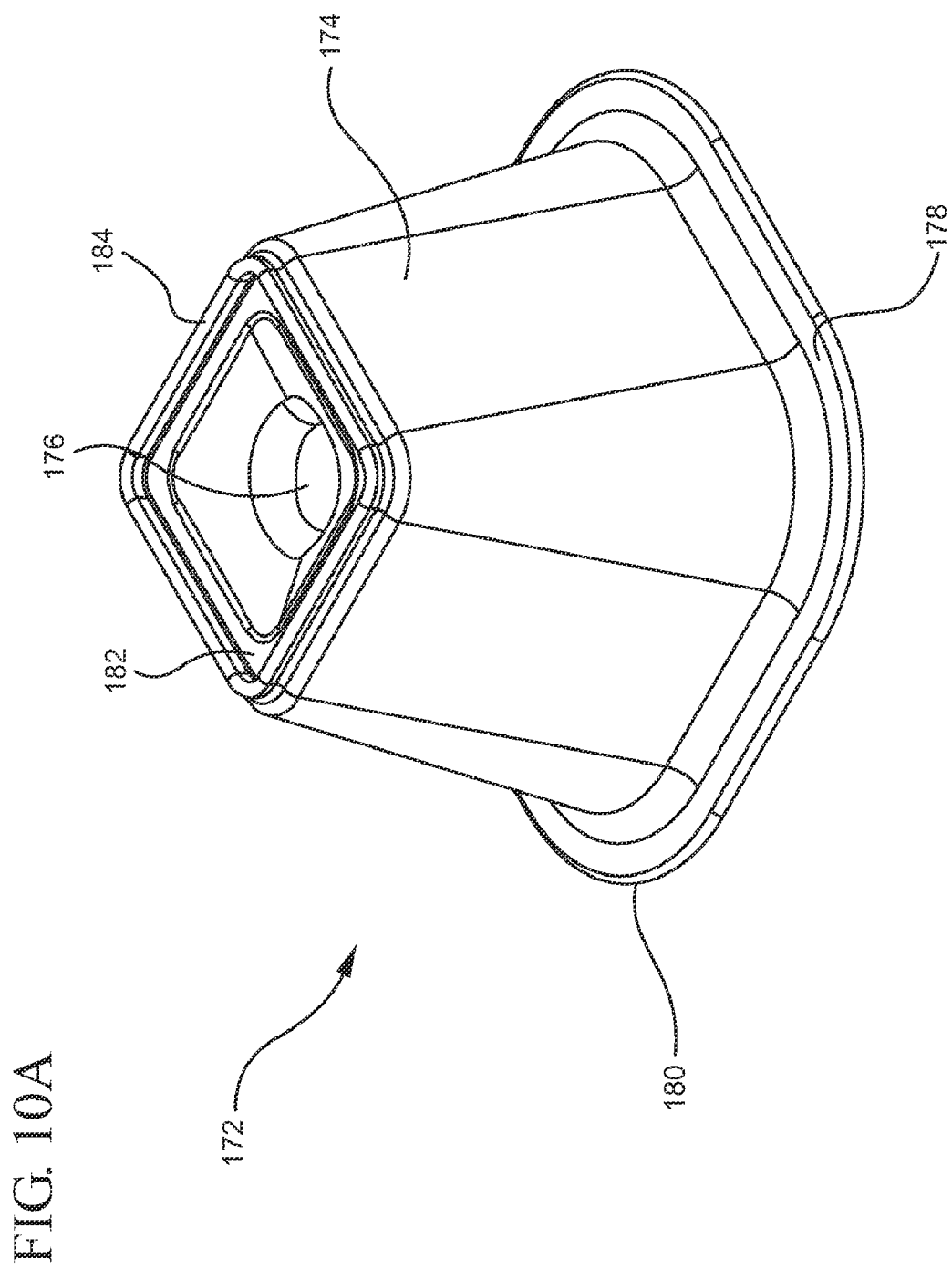

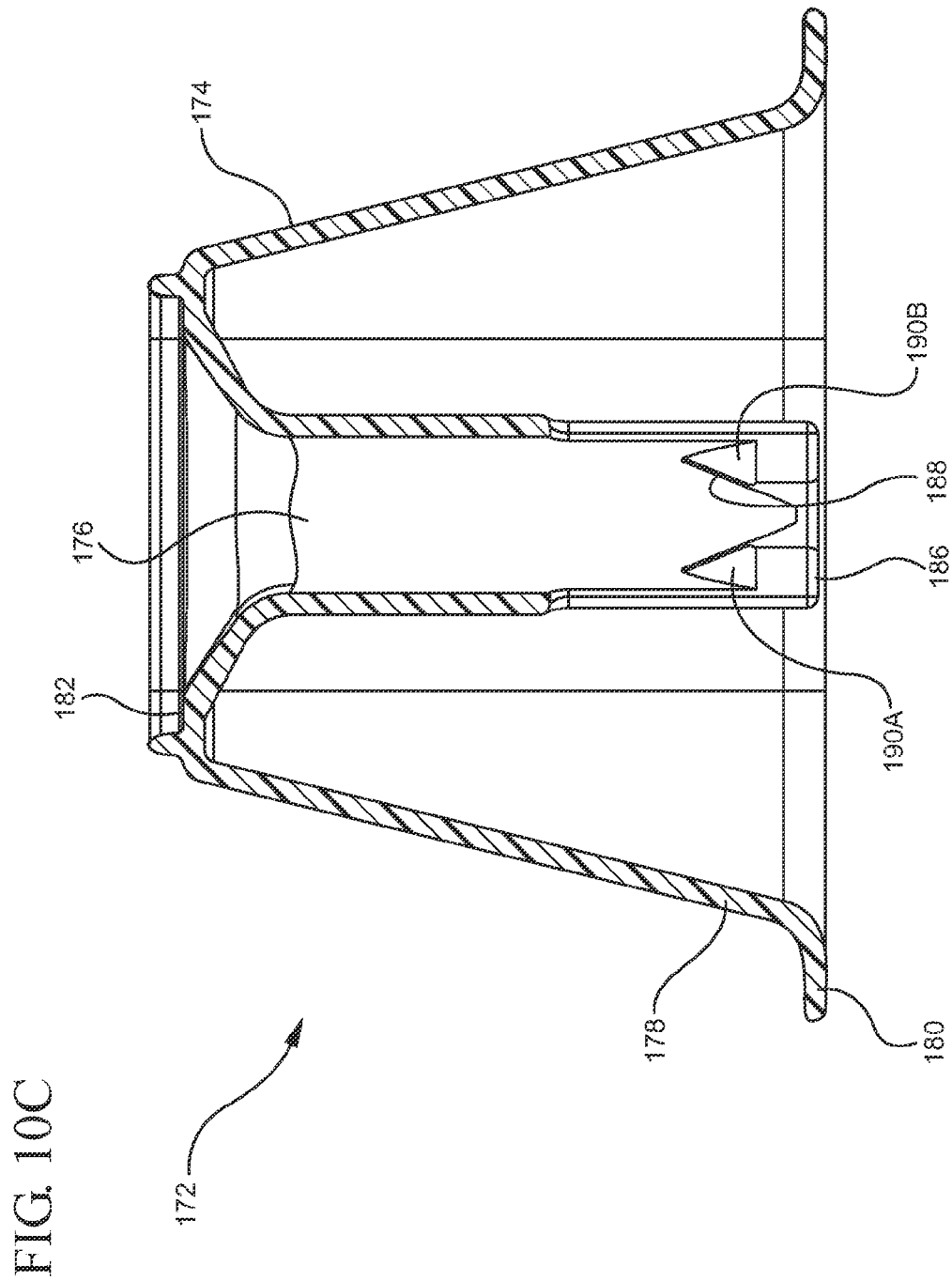

FIG. 21
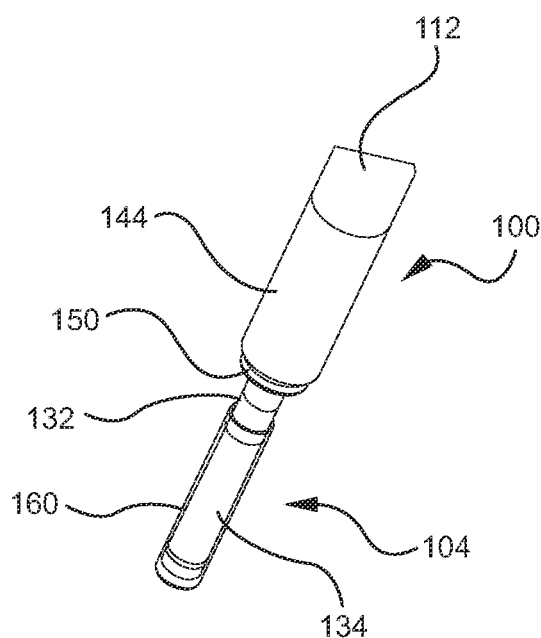
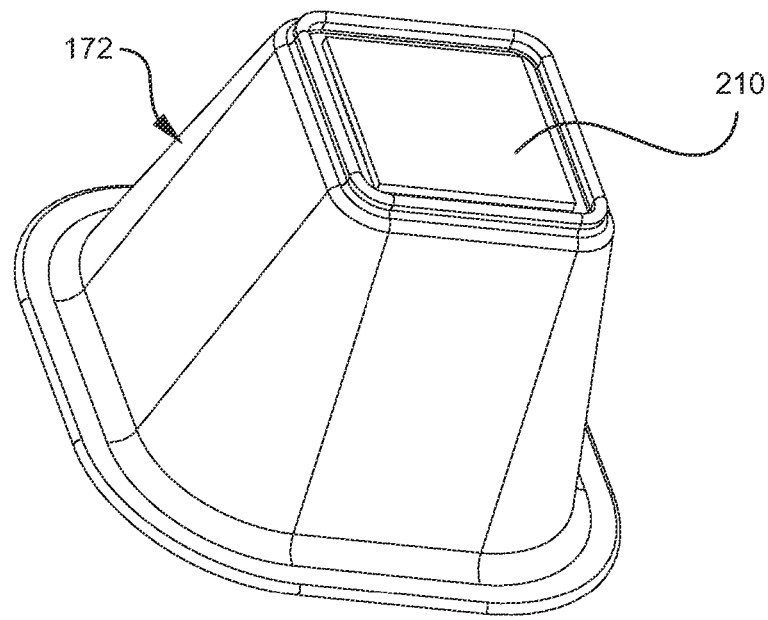

APPLICATOR INSTRUMENTS HAVING PROTECTIVE CARRIERS FOR HEMOSTATS AND METHODS THEREFOR

CROSS REFERENCE TO RELATED APPLICATIONS

The present application is related to commonly assigned U.S. patent application Ser. No. 12/049,849, entitled "APPLICATOR INSTRUMENTS FOR THE DELIVERY, DEPLOYMENT, AND TAMPONADE OF HEMOSTATS AND METHODS THEREFOR", filed on Mar. 17, 2008, the disclosure of which is hereby incorporated by reference herein.

BACKGROUND OF THE INVENTION

1. Field of the Invention

The present application is generally related to controlling bleeding, and is more specifically related to systems, instruments, and methods used for the delivery, deployment, and tamponade of hemostats.

2. Description of the Related Art

Medical textiles are used during surgical procedures to control bleeding, minimize blood loss, reduce post-surgical complications, and shorten the duration of surgery. Commonly used medical textiles include adhesion barriers, sponges, meshes, and hemostatic wound dressings that are applied to the surface of tissue. Hemostatic wound dressings include absorbable hemostats such as those sold by Ethicon, Inc. of Somerville, N.J. under the registered trademarks Surgicel®, Surgicel Nu-Knit®, and Surgicel® Fibrillar.

Traditionally, medical textiles have been delivered to surgical sites using grasping instruments such as clamps and forceps. It is also well-known to use applicator instruments for delivering medical textiles. For example, U.S. Pat. No. 3,857,395 discloses an inserter device having a pair of outwardly bendable arms that bilaterally spread an adhesion barrier within a vaginal cavity. The inserter device disclosed in the '395 patent, however, is not suitable for insertion through an endoscopic tube or trocar.

Commonly assigned U.S. Pat. No. 5,395,383 discloses an applicator instrument used for applying a sheet of surgical material (i.e. an adhesion barrier) through an endoscopic tube. The applicator instrument includes an expandable operating tip that is insertable into an endoscopic tube to enable a surgeon to apply the surgical material to tissue inside a body. In one embodiment, the applicator comprises a set of telescoping tubes including an outer delivery tube, an intermediate deployment tube, and an inner irrigation tube. The expandable operating tip is mounted at the distal end of the irrigation tube and is connected to the distal end of the deployment tube. The spreader tip is exposed at the distal end of the delivery tube by advancing the deployment tube and the irrigation tube relative to the delivery tube. The spreader tip is expanded by movement of the deployment tube relative to the irrigation tube to spread the sheet of surgical material over the tissue. A nozzle is provided at the distal end of the irrigation tube for applying a fluid, e.g., a saline solution, to the surgical material.

Commonly assigned U.S. Pat. No. 5,397,332 discloses an applicator for applying a sheet of surgical material, e.g., a surgical mesh, to internal body tissue. The applicator includes a delivery tube, a deployment tube slidably received within the delivery tube, and a shaft or irrigation tube slidably received within the deployment tube. An expandable spreader tip is connected between the distal ends of the shaft and the deployment tube. The spreader tip is collapsed and inserted in the delivery tube with the surgical mesh. The applicator is inserted through a trocar tube into a body cavity and the spreader tip is exposed by retracting the delivery tube relative to the deployment tube and shaft. The applicator has a first actuator for urging the spreader tip and surgical mesh into engagement with the tissue as the deployment tube is retracted, and a second actuator for advancing the deployment tube relative to the shaft to expand the spreader tip to apply the surgical mesh to the tissue. The spreader tip includes a plurality of flexible strips each having opposite ends pivotally connected to the distal ends of the shaft and the deployment tube. The applicator includes a return spring to bias the deployment tube proximally relative to the shaft to normally maintain the spreader tip in a collapsed configuration.

In spite of the above advances, there remains a need for improved instruments and methods for the delivery, accurate placement, deployment, and tamponade of medical textiles such as adhesion barriers, wound dressings, and topically applied hemostats. More particularly, there remains a need for applicator instruments that are insertable through an endoscopic tube and that are capable of spreading medical textiles over a tissue application area to minimize the need for manipulation of the medical textiles by separate grasping instruments.

In addition, there remains a need for instruments and methods for the delivery, deployment, and tamponade of medical textiles having moisture-sensitive components (e.g. moisture-sensitive adhesives), which may become ineffective when exposed to fluids or moisture before reaching a target tissue site.

Moreover, there also remains a need for applicator instruments and methods for the delivery, deployment, and tamponade of medical textiles having loosely bound additives such as thrombin and fibrinogen that may become dislodged before the medical textiles are placed in contact with the target tissue.

SUMMARY OF THE INVENTION

In one embodiment, the present invention discloses an applicator instrument used for the endoscopic delivery of medical textiles such as meshes, hemostats, adhesion prevention barriers, and sponges. In one embodiment, the applicator instrument is preferably adapted for the endoscopic delivery, deployment and tamponade of hemostats such as topically applied hemostats (TAH). The applicator instrument desirably protects the topically applied hemostat from exposure to fluids and moisture until the hemostat is delivered and deployed onto the target tissue. In the present application, the terms "hemostat" and "topically applied hemostat" are used most frequently to describe the various medical textiles that may be delivered and deployed by the present invention. However, the present application contemplates that these terms should be read broadly to cover all of the medical textiles described, as well as other materials conventionally used to control bleeding.

In one embodiment, the applicator instrument includes a balloon that is used to endoscopically deploy and tamponade a hemostat. The deflated balloon is desirably attached at each end to one of two pieces of concentric tubing such that one balloon end is movable and the shape of the inflated balloon is changeable from a rounder shape to a flatter shape, such as from a spherical shape to a toroidal shape. In one embodiment, the distal end of the balloon is inverted and the inverted surface is attached to the outer surface of one of the concentric tubes so that when the balloon is inflated the attachment of the distal end of the balloon to the distal end of the device is located inside the inflated balloon. This configuration provides a flatter surface area of the balloon for applying an evenly distributed tamponade pressure to the hemostat.

In one embodiment, a cartridge with a breakable or traversable seal at a distal end thereof protects the hemostat from moisture until the hemostat is applied to tissue. Barbed or Velcro®-like hooks may be incorporated at the distal end of the applicator instrument, and the hooks or barbs may be used to pick up the hemostat for loading the hemostat into the tubular cartridge. In other embodiments (e.g. where protection from moisture is not needed), the cartridge may not be used and the hooks hold the hemostat at the distal tip of the instrument as the instrument is passed through an endoscope or trocar to a surgical site. In one embodiment, a system for the delivery, deployment, and tamponade of hemostats may include an applicator device, a plurality of cartridges, and a stand or cartridge loader for aligning and loading the hemostats into the cartridges.

In one embodiment of the present invention, an instrument for controlling bleeding includes an intermediate shaft having a proximal end, a distal end, and a central lumen extending to the distal end thereof, and an inner shaft telescopically received within the central lumen of the intermediate shaft, the inner shaft having a proximal end and a distal end that extends distally from the intermediate shaft. The instrument preferably includes a balloon having a proximal end secured to the intermediate shaft and a distal end secured to the inner shaft, a first actuator for inflating the balloon, and a second actuator for moving the distal ends of the intermediate and inner shafts relative to one another for changing the shape of the inflated balloon. In one embodiment, the proximal end of the balloon is secured to the distal end of the intermediate shaft and the distal end of the balloon is secured to the distal end of the inner shaft. The distal end of the balloon may be inverted and the inverted surface of the balloon may be secured to the outer surface of the inner shaft at the distal end of the inner shaft.

The intermediate and inner shafts may be moved relative to one another for changing the shape of the inflated balloon. In one embodiment, the balloon has a rounder or spherical shape when the intermediate and inner shafts are in a first position and a flatter or toroidal shape when the intermediate and inner shafts are in a second position. In one embodiment, the balloon assumes a toroidal shape, and the flattened leading face of the balloon is used to apply tamponade pressure to one or more hemostats.

In one embodiment, the applicator instrument includes an outer shaft having a proximal end, a distal end, and a central lumen extending to the distal end of the outer shaft. The intermediate and inner shafts are preferably disposed within the central lumen of the outer shaft. The intermediate shaft desirably extends distally from the distal end of the outer shaft and is adapted to slide telescopically relative to the outer shaft. In one embodiment, the applicator instrument may include a third actuator coupled with the outer shaft for moving the distal end of the outer shaft proximally relative to the distal ends of the intermediate and inner shafts for the purpose of retracting/moving an attached cartridge connector and cartridge assembly as described in more detail below.

In one embodiment, the outer shaft has structure such as a cartridge connector provided at a distal end thereof that is adapted to be connected to a cartridge. The cartridge connector desirably has a groove or ridge that is adapted to form a detachable coupling or snap-fit connection with a cartridge. When an actuator coupled with the outer shaft is engaged, the outer shaft and the cartridge connected therewith move toward the proximal end of the instrument. In one embodiment, as the cartridge moves proximally, a hemostat is delivered through a fluid-resistant seal provided at a distal end of the cartridge.

The applicator instrument may include a hemostat disposed at the distal end of the inner shaft. The hemostat may be a medical textile, a topically applied adhesive, a hemostat patch folded over the distal end of the inner shaft, or any conventional medical device used to control bleeding. The inner shaft may have barbs or hooks provided at the distal end thereof for attaching the hemostat to the inner shaft. A fluid-resistant element may cover the hemostat and be connected to the distal end of the outer shaft. The fluid-resistant element may include a seal that may be broken for enabling the hemostat to pass through the seal. In one embodiment, the fluid-resistant element is a cartridge including a cartridge tube having an opening at a proximal end of the tube and a fluid-resistant seal at a distal end of the tube. The hemostat preferably remains in a fluid-resistant compartment defined by the cartridge until the fluid-resistant seal is broken and the hemostat passes through the broken seal.

In another embodiment of the present invention, an instrument for controlling bleeding includes an outer shaft having a proximal end, a distal end, and a central lumen extending to the distal end thereof, an intermediate shaft telescopically received within the central lumen of the outer shaft, the intermediate shaft having a proximal end, a distal end that extends distally from the distal end of the outer shaft, and a central lumen extending to the distal end thereof. The instrument desirably includes an inner shaft telescopically received within the central lumen of the intermediate shaft, the inner shaft having a proximal end and a distal end that extends distally from the intermediate shaft. The instrument desirably includes an inflatable balloon having a proximal end secured to the distal end of the intermediate shaft and a distal end that is inverted and secured to the distal end of the inner shaft. A fluid inlet is desirably located between the proximal and distal ends of the balloon for selectively inflating the balloon. A medical textile such as a hemostat is preferably disposed at the distal end of the inner shaft. The instrument desirably includes at least one actuator for selectively moving the distal ends of the intermediate and inner shafts relative to one another for changing the shape of the balloon. In one embodiment, the shape of an inflated balloon may be changed from a generally spherical shape to a generally toroidal shape.

In one embodiment, a fluid-resistant element may cover the hemostat and be connected with the distal end of the outer shaft. The fluid-resistant element desirably comprises a breakable, fluid-resistant seal through which the hemostat may pass for being delivered and deployed at a surgical site.

In one embodiment, the instrument includes a first actuator coupled with the outer shaft for selectively moving the outer shaft proximally relative to the distal ends of the intermediate and inner shafts, a second actuator for selectively inflating the balloon, and a third actuator coupled with at least one of the intermediate and inner shafts for selectively moving the distal ends of the intermediate and inner shafts relative to one another for changing the shape of an inflated balloon. In one embodiment, the intermediate and inner shafts desirably have tubular shapes, and at least one of the intermediate and inner shafts has an opening for introducing fluid, such as air, into the balloon.

In one embodiment of the present invention, an instrument for controlling bleeding includes an outer shaft having a proximal end and a distal end, a balloon disposed at the distal end of the outer shaft, a medical textile such as a hemostat disposed adjacent the balloon, an actuator for inflating the balloon, and another actuator for changing the shape of the inflated balloon. The outer shaft desirably has a central lumen extending to a distal end thereof.

The instrument may also include an intermediate shaft telescopically received within the central lumen of the outer shaft, the intermediate shaft having a proximal end, a distal end that extends distally from the distal end of the outer shaft, and a central lumen extending to the distal end thereof. The instrument also preferably includes an inner shaft telescopically received within the central lumen of the intermediate shaft, the inner shaft having a proximal end and a distal end that extends distally from the intermediate shaft, and the balloon having a proximal end secured to the distal end of the intermediate shaft and a distal end secured to the distal end of the inner shaft.

In one embodiment of the present invention, a method for controlling bleeding includes providing an applicator instrument, a hemostat such as a topically applied textile, a cartridge for holding the hemostat, and a cartridge loader for facilitating loading the hemostat into the cartridge and attaching the loaded cartridge to a distal end of the applicator instrument. In one embodiment, a cartridge loader is positioned atop a support surface and a cartridge is loaded into the cartridge loader. A hemostat such as a hemostatic patch may be placed atop an opening at a proximal or upper end of the cartridge loader. As the hemostatic patch is placed atop the cartridge loader, it is also centered over an opening at the proximal end of the cartridge. The distal tip of the applicator instrument may be abutted against the hemostatic patch for pushing the hemostatic patch into the cartridge. In one embodiment, the hemostat may have one surface treated with a component, and the treated surface may be oriented face up or face down as needed. As the distal tip is advanced into the cartridge, the hemostatic patch may wrap or fold around the distal tip. In one embodiment, the applicator tip is fully inserted into the cartridge until a snap-fit connection is formed between the cartridge and the tip of the applicator instrument. After the cartridge is connected to the tip of the applicator instrument, the tip of the applicator instrument and the cartridge may be removed from the central opening of the cartridge loader.

The applicator instrument, with the hemostatic patch and cartridge connected thereto, may be advanced to a surgical site such as by passing the cartridge and the tip of the applicator instrument through an endoscope or trocar. In one embodiment, the distal end of the cartridge includes a fluid-resistant seal such as a breakable seal including a rubber tip. The seal of the cartridge is advanced until the seal abuts against the target tissue at a surgical site. An actuator such as a trigger may be pulled to move the cartridge towards the proximal end of the applicator instrument. As the cartridge moves towards the proximal end, the hemostatic patch pierces through the fluid-resistant seal at the distal end of the cartridge so that the patch may be delivered against the tissue surface. In one embodiment, the applicator instrument includes a trigger lock. When the trigger lock is in a locked position, the trigger may not be pulled for delivering the hemostatic patch through the fluid-resistant seal. When the trigger lock is in an unlocked position, the trigger may be pulled for delivering the hemostat from the cartridge.

After the hemostatic patch has been delivered to the surgical site, a balloon at the distal end of the applicator instrument may be inflated by engaging an actuator such as a syringe plunger. As the balloon is inflated, the expanding balloon deploys the hemostatic patch by unfurling the hemostatic patch and advancing the edges of the hemostatic patch toward the tissue surface at the surgical site. When the balloon is inflated, it normally assumes a substantially spherical shape. The shape of the balloon may be changed, however, by engaging another actuator such as a deformation slider that changes the shape of the balloon into a substantially toroidal shape. In the toroidal shape, a leading face of the balloon now assumes a substantially flatter surface that provides more surface area for engaging the delivered and deployed hemostatic patch. In one embodiment, tamponade pressure is applied by the balloon to the hemostatic patch for approximately 1-5 minutes, and more preferably 2-3 minutes.

In one embodiment, the inflatable balloon is transparent so that the deployment and tamponade of the hemostat may be observed through the balloon. If bleeding has not been controlled after a predetermined period of time, this condition may be observed through the transparent balloon. In response to this condition, tamponade pressure may be applied for longer time periods until the bleeding has stopped or is under control.

In one embodiment, after the bleeding is under control, the deformation slider may be retracted for returning the intermediate and inner shafts to the normal spacing configuration. As the deformation slider is retracted, the balloon is preferably transformed from a toroidal shape back to the original spherical shape. The inflated balloon may be deflated by engaging a syringe plunger locking ring that releases the plunger for deflating the balloon. A spring provided inside the syringe may return the plunger to the retracted position. After the balloon is deflated, the tip of the applicator instrument may be retracted from the surgical site and removed from the endoscope or trocar. After the applicator instrument is withdrawn from the surgical site, the hemostat preferably remains in place atop the tissue at the surgical site for controlling bleeding.

Although the present invention is not limited by any particular theory of operation, it is believed that the present invention provides numerous benefits over prior art instruments, systems, and methods. One advantage of the present invention is that the instrument protects hemostats that include moisture-sensitive components from premature exposure to moisture or fluids (e.g. bodily fluids). This may be accomplished using a fluid-resistant element that surrounds the hemostat until the hemostat is delivered to the tissue surface at a surgical site.

In one embodiment, an instrument for delivering a hemostat, such as a topically applied hemostat, includes an outer shaft having a proximal end and a distal end, a hemostat disposed at the distal end of the outer shaft, and a fluid-resistant element connected to the distal end of the outer shaft and surrounding the hemostat, whereby the fluid-resistant element has a breakable, fluid-resistant seal at a distal end thereof. The fluid-resistant element may be snap-fit onto the distal end of the outer shaft. The breakable, fluid-resistant seal may be a pierceable membrane, a rubber seal, or a cross-slit (four-way duckbill) valve. The fluid-resistant element may include a cartridge having a breakable, fluid-resistant seal at a distal end thereof. The cartridge may include a cartridge tube having a proximal end, a distal end, and a central opening extending between the proximal and distal ends thereof. The cartridge may also include the breakable, fluid-resistant seal covering the central opening at the distal end of the cartridge tube. In one embodiment, the cartridge tube has structure for connecting to the distal end of the outer shaft. The connecting structure may include one or more ridges, projections, bumps, grooves, depressions, a press-fit, and/or threads.

The instrument may also include the outer shaft having a central lumen extending to the distal end thereof, an intermediate shaft telescopically received within the central lumen of the outer shaft, the intermediate shaft having a proximal end, a distal end that extends distally from the distal end of the outer shaft, and a central lumen extending to the distal end thereof, and an inner shaft telescopically received within the central lumen of the intermediate shaft, the inner shaft having a proximal end and a distal end that extends distally from the intermediate shaft. The instrument may also include a balloon having a proximal end secured to the distal end of the intermediate shaft and a distal end secured to the distal end of the inner shaft, whereby the hemostat is disposed at the distal end of the inner shaft and the fluid-resistant element is connected to the distal end of the outer shaft and surrounds the hemostat for forming a fluid-resistant chamber around the hemostat.

In one embodiment, the instrument includes a first actuator coupled with the outer shaft for selectively moving the distal end of the outer shaft and the fluid-resistant element proximally for breaking the fluid-resistant seal and delivering the hemostat from the distal end of the instrument. The instrument may also include a second actuator for inflating the balloon, and a third actuator for moving the distal ends of the intermediate and inner shafts relative to one another for changing the shape of the inflated balloon.

In one embodiment, the instrument includes a cartridge loader having an upper end with a platform, and a central opening extending from the platform toward a lower end of the cartridge loader, whereby the central opening is adapted to receive the cartridge and the cartridge platform is adapted to receive a hemostat prior to loading the hemostat into the cartridge. The central opening of the cartridge loader desirably has a closed end with a support surface that conforms to the fluid-resistant seal at the distal end of the cartridge.

In one embodiment, an instrument for controlling bleeding includes an outer shaft having a proximal end, a distal end, and a central lumen extending to the distal end thereof, an intermediate shaft telescopically received within the central lumen of the outer shaft, the intermediate shaft having a proximal end, a distal end, and a central lumen extending to the distal end thereof, and an inner shaft telescopically received within the central lumen of the intermediate shaft, the inner shaft having a proximal end and a distal end that extends distally from the intermediate shaft. The instrument also desirably includes a hemostat disposed at the distal end of the inner shaft, and a water-resistant element connected to the distal end of the outer shaft and surrounding the hemostat, whereby the water-resistant element has a breakable, water-resistant seal at a distal end thereof.

In one embodiment, an instrument for controlling bleeding includes an outer shaft having a proximal end and a distal end, a balloon disposed at the distal end of the outer shaft, a hemostat disposed adjacent to balloon, and a fluid-resistant element secured to the distal end of the outer shaft and surrounding the hemostat to form a fluid-resistant compartment around the hemostat, whereby the fluid-resistant element has a breakable, fluid-resistant seal at a distal end thereof.

In one embodiment, a protective enclosure surrounds the hemostats during the delivery of the hemostats to a surgical site to prevent excessive loss of loosely attached components disposed on hemostats before the deployment of the hemostats to target tissue. This feature is particularly important for hemostats having critical and/or costly components such as human thrombin or fibrinogen.

The present invention also enables the shape of an inflated balloon to be altered so as to maximize the surface area available for applying tamponade pressure to a deployed hemostat. The increased surface area and the flatter surface area allows for more efficient and enhanced tamponade pressure to be applied to the hemostats. This feature is particularly useful for applying pressure to topically applied hemostats.

In addition, in one embodiment, the present invention discloses an applicator instrument having a transparent balloon that enables medical personnel to observe a surgical site as tamponade pressure is applied to hemostats using the balloon.

In one embodiment, the intermediate shaft of the applicator instrument is not moveable, and the balloon does not change shape. After the balloon is inflated to a desired shape, either spherical or toroidal as described earlier, the fluid used to inflate the balloon is communicated between the outer diameter (OD) of the inner shaft and the inner diameter (ID) of the intermediate shaft. There is desirably no side hole in the inner shaft as described in other embodiments, and there is no distal end plug in the lumen of the inner shaft. The lumen of the inner shaft may be in communication through the proximal handle of the device. The proximal end of the inner shaft may have a syringe connector means, such as a Luer connector, attached thereto. The Luer connector may be used to attach a syringe that dispenses a fluid (e.g. SURGIFLO) through the lumen of the inner shaft into a surgical cavity, with the balloon in either an inflated or deflated state. The lumen of the inner shaft may also be used to guide, support and allow passage of other fluid delivery systems, such as the EVICEL Fibrin Sealant having a 45 cm catheter delivery device. Moreover, a Luer cap or plug may be attached to the Luer connector to prevent surgical cavity insufflation gases from undesirably exiting through the instrument. In one embodiment, a stylet may be attached to and through the Luer, the length of the stylet being such that its tip is in close proximity to the distal end of the lumen of the inner shaft. The distal tip of the stylet may have Velcro-like barbs, for the purpose of engaging and picking up and a textile based topically applied hemostat (TAH) as described herein in the present application.

In one embodiment, the applicator instrument may not have the intermediate shaft and its related features, and the balloon may not change shape after it is inflated to have either a spherical or toroidal shape as described earlier. In one embodiment, both the distal and proximal ends of the balloon are attached to the outer diameter (OD) of the inner shaft, in the manner as described earlier These and other preferred embodiments of the present invention will be described in more detail below.

BRIEF DESCRIPTION OF THE DRAWINGS

FIGS. 6A and 6B show cross-sectional views of a distal end of the instrument shown in FIGS. 1 and 2.

FIGS. 7A and 7A-1 show respective front elevational and cross-sectional views of the distal end of the instrument shown in FIGS. 1 and 2 with a balloon in an inflated state.

FIGS. 7B and 7B-1 show respective front elevational and cross-sectional views of the distal end of the instrument shown in FIGS. 7A and 7A-1 after the shape of the inflated balloon has been changed.

FIGS. 8A and 8B show cross-sectional views of the distal end of an instrument for the delivery, deployment, and tamponade of hemostats, in accordance with one embodiment of the present invention.

FIG. 9A shows the distal end of the instrument shown in FIGS. 8A and 8B with a balloon in an inflated state.

FIG. 9B shows the distal end of the instrument shown in FIG. 9A after the shape of the inflated balloon has been changed.

FIG. 10A shows a perspective view of a cartridge loader, in accordance with one embodiment of the present invention.

FIGS. 10B and 10C show cross-sectional views of the cartridge loader shown in FIG. 10A.

FIGS. 18-25 show a method of loading a hemostat into a cartridge and connecting a cartridge to a distal end of the instrument shown in FIGS. 1 and 2, in accordance with one embodiment of the present invention.

FIGS. 27G-1 and 27G-2 show other views of the step shown in FIG. 27G.

FIGS. 27I-1 and 27I-2 show other views of the step shown in FIG. 27I.

DETAILED DESCRIPTION

Figure 1:
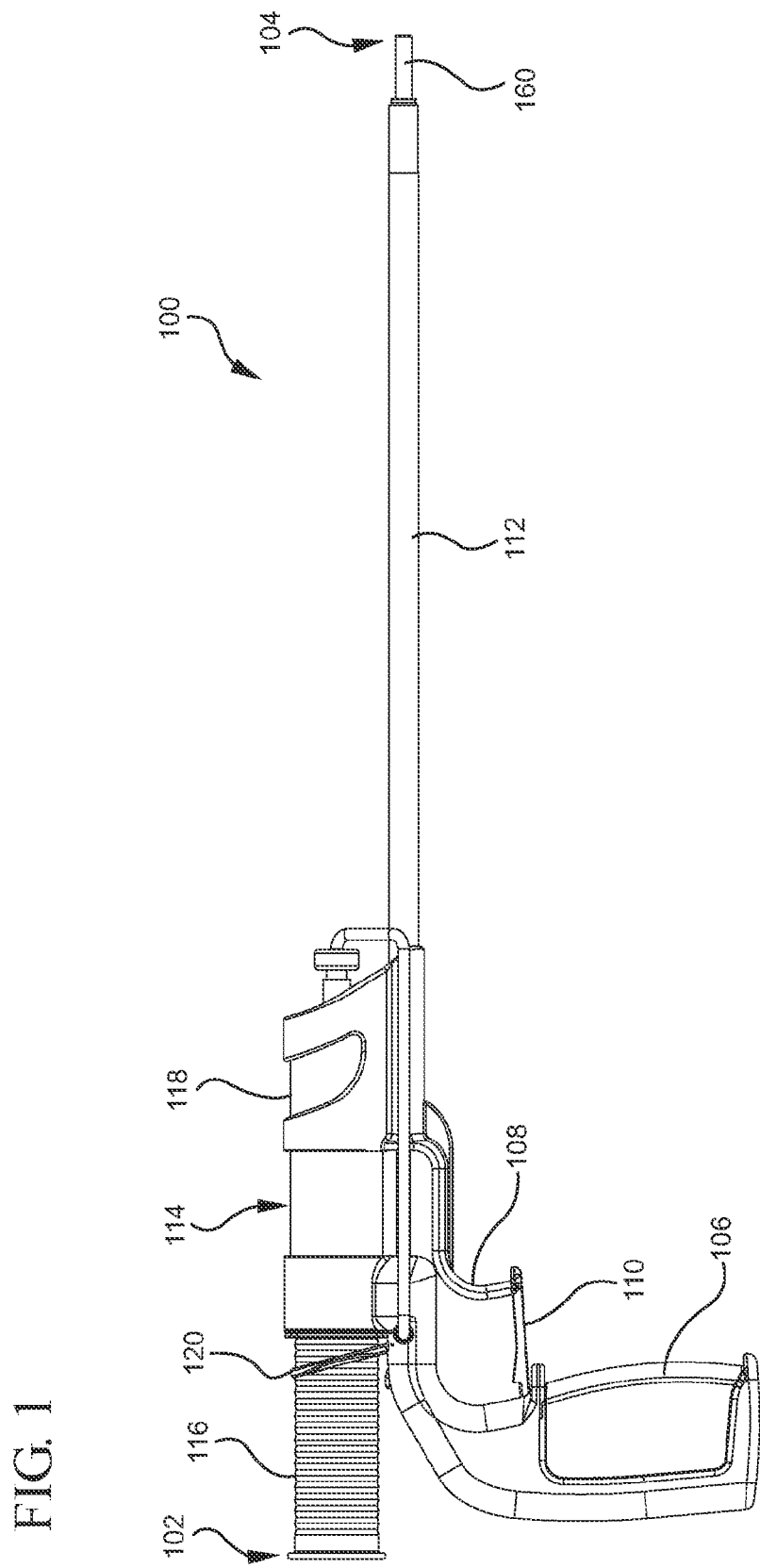
FIG. 1 shows a right side elevational view of an instrument for the delivery, deployment, and tamponade of hemostats, in accordance with one embodiment of the present invention.

The invention disclosed herein is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways.

The headings used herein are for organizational purposes only and are not meant to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

Figure 2:
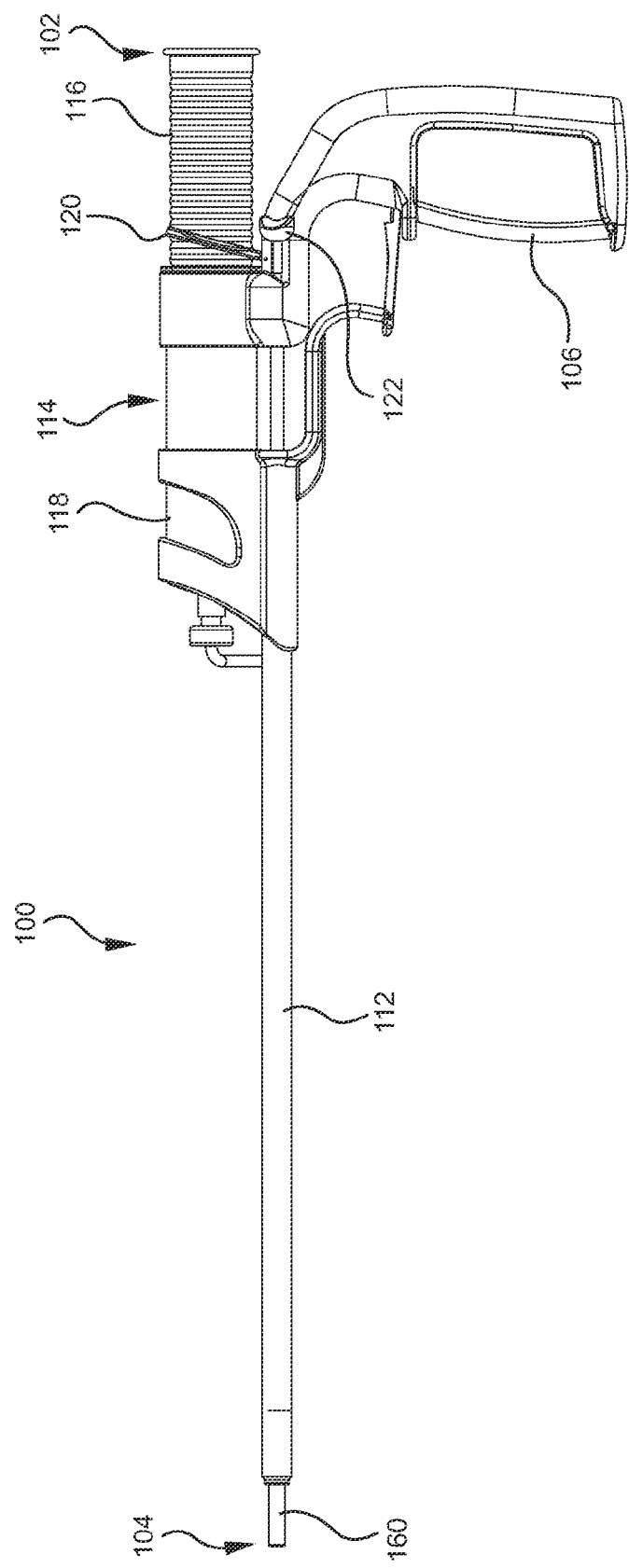
FIG. 2 shows a left side elevational view of the instrument shown in FIG. 1.

Referring to FIGS. 1 and 2, a system for the delivery, deployment, and tamponade of hemostats such as topically applied hemostats includes an applicator instrument 100 having a proximal end 102 and a distal end 104. The instrument 100 includes a handle 106 having a trigger 108 and a trigger lock 110. The trigger 108 is coupled with an outer shaft 112 that extends toward the distal end 104 of the instrument 100. The trigger 108 may be pulled for moving the outer shaft 112 in a proximal direction toward the proximal end 102 of the applicator instrument 100.

The instrument 100 also includes a syringe 114 that is used to selectively inflate a balloon 160 desirably located adjacent the distal end 104 of the instrument. The syringe 114 includes a plunger 116 and a barrel 118 that receives the plunger 116. The plunger 116 may be pressed toward the distal end 104 of the instrument 100 for inflating the balloon. The syringe 114 also includes a plunger locking ring 120 that desirably locks the plunger 116 from movement relative to the barrel 118. The plunger locking ring 120 may be moved to an unlocked position (e.g. moved toward the distal end 104 of the instrument 100) for enabling the plunger 116 to move relative to the barrel 118. The syringe 114 may include an internal spring for returning the plunger 116 to an extended position. In one embodiment, the syringe 114 may include a seal (not shown) that is positioned between the plunger and the barrel to maintain a pneumatic or hydraulic seal. Referring to FIG. 2, the applicator instrument 100 also includes a deformation slider 122 that may be pressed toward the distal end 104 of the instrument for changing the shape of the balloon 160 when the balloon is inflated, as will be described in more detail below.

Figure 3:
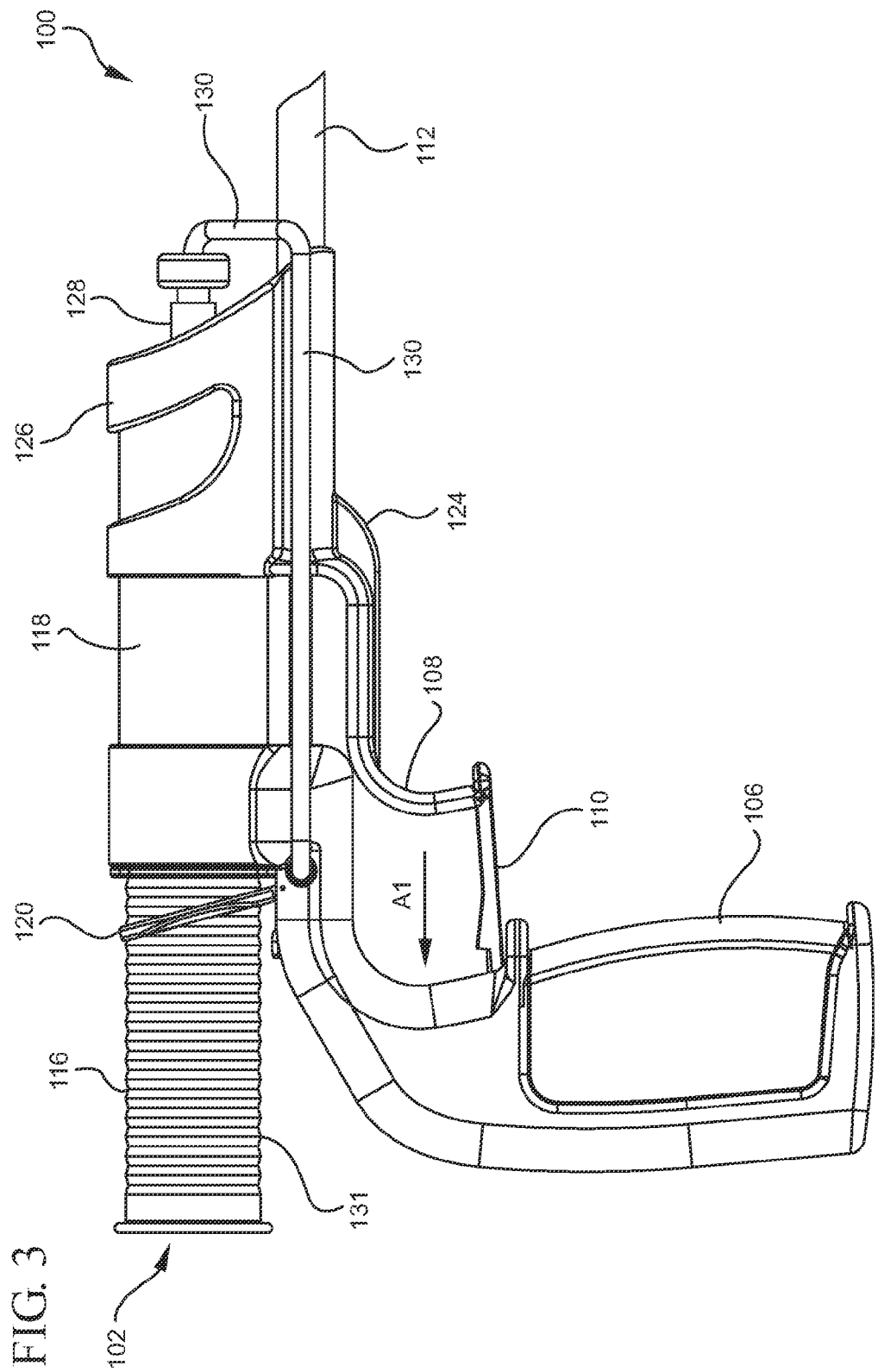
FIG. 3 shows a right side elevational view of a proximal end of the instrument shown in FIG. 1.

Referring to FIG. 3, the handle 106, located at the proximal end 102 of the instrument 100, includes the trigger 108 and the trigger lock 110. In operation, the trigger lock 110 may be moved to an unlocked position to enable the trigger 108 to be pulled toward the proximal end 102 of the instrument 100. The direction that the trigger 108 may be pulled is designated $A_1$ in FIG. 3. In other embodiments, the trigger or another form of actuator may be pulled in another direction. A leading end 124 of the trigger 108 may be connected to a hollow tube 126 that is adapted to slide over the plunger barrel 118. The trigger 108 is coupled to the outer shaft 112 via the trigger leading end 124 and the hollow barrel 126.

The distal end of the plunger barrel 118 includes a connector 128 that is coupled with a conduit 130 that is used to direct fluid such as high pressure air into the inflatable balloon (not shown). As will be described in more detail below, the fluid passes through an inner shaft having an opening located inside the inflatable balloon. As the plunger 116 is depressed into the barrel 118, the fluid is directed through the conduit 130 and into the balloon for inflating the balloon. When desired, the inflatable balloon may be deflated by enabling the plunger to return to an extended position as shown in FIG. 3.

When the plunger locking ring is in the position shown FIG. 3, the plunger 116 is locked in place relative to the plunger barrel 118. In order to return the plunger 116 to the extended position, the plunger locking ring 120 may be moved toward the distal end of the instrument 100. The outer surface of the plunger 116 desirably includes ridges 131 that may engage the plunger locking ring 118 for selectively locking the plunger 116 in place. In one embodiment, the outer surface of the plunger may not have ridges, but may have a smooth or roughened surface that allows frictional engagement with the inner diameter of the locking ring.

Figure 4:
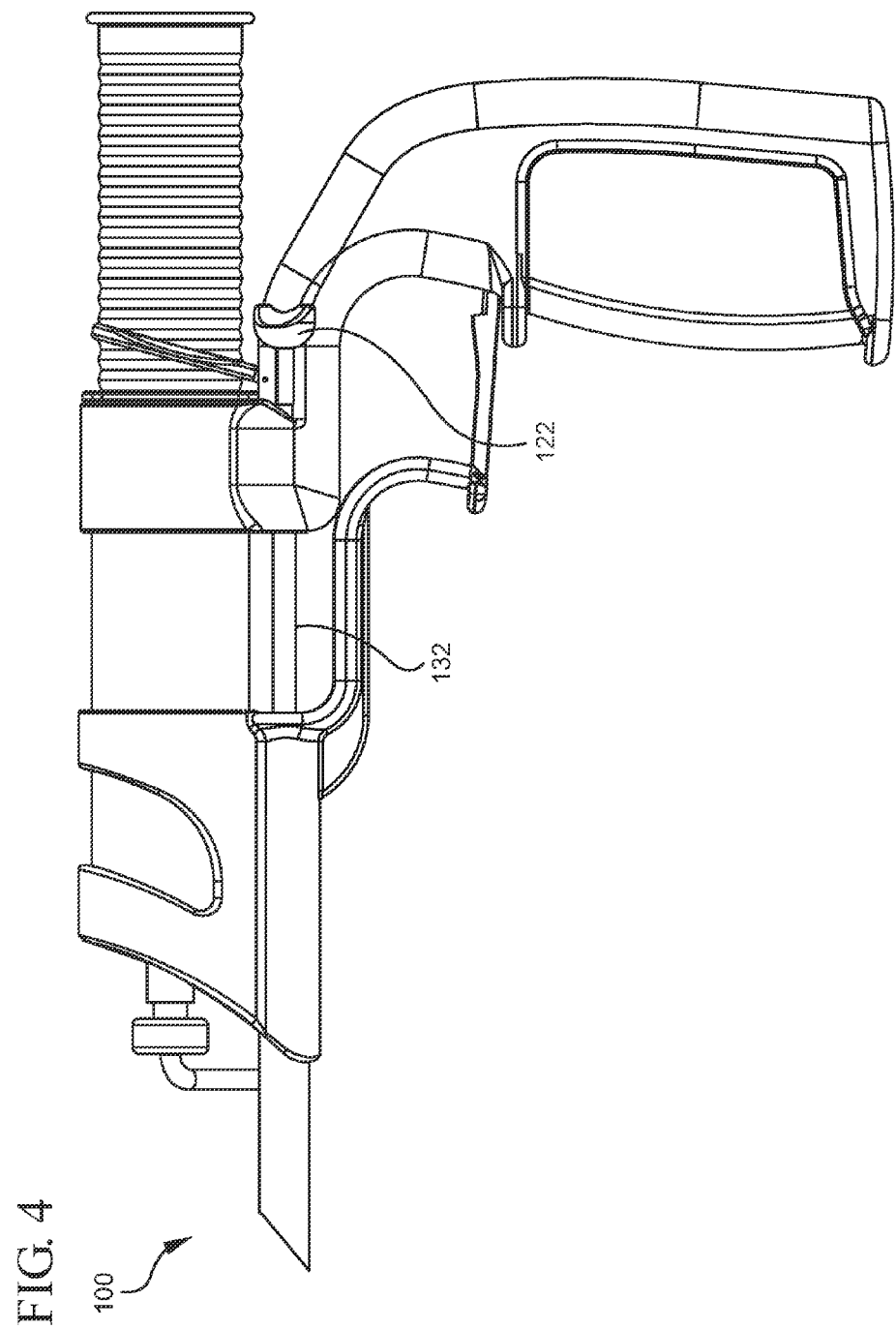
FIG. 4 shows a left side elevational view of the proximal end of the instrument shown in FIG. 2.

Referring to FIG. 4, in one embodiment of the present invention, the instrument 100 includes the deformation slider 122 that may be advanced toward the distal end of the instrument. The deformation slider 122 is coupled with a proximal end of an intermediate shaft 132. The intermediate shaft 132 has a distal end (not shown) that is attached to a proximal end of the inflatable balloon. In a preferred embodiment, the proximal end of the inflatable balloon is attached to the outer surface of the intermediate shaft 132 at the distal end of the intermediate shaft 132. An air-tight seal preferably exists between the proximal end of the inflatable balloon and the distal end of the intermediate shaft 132.

Figure 5:
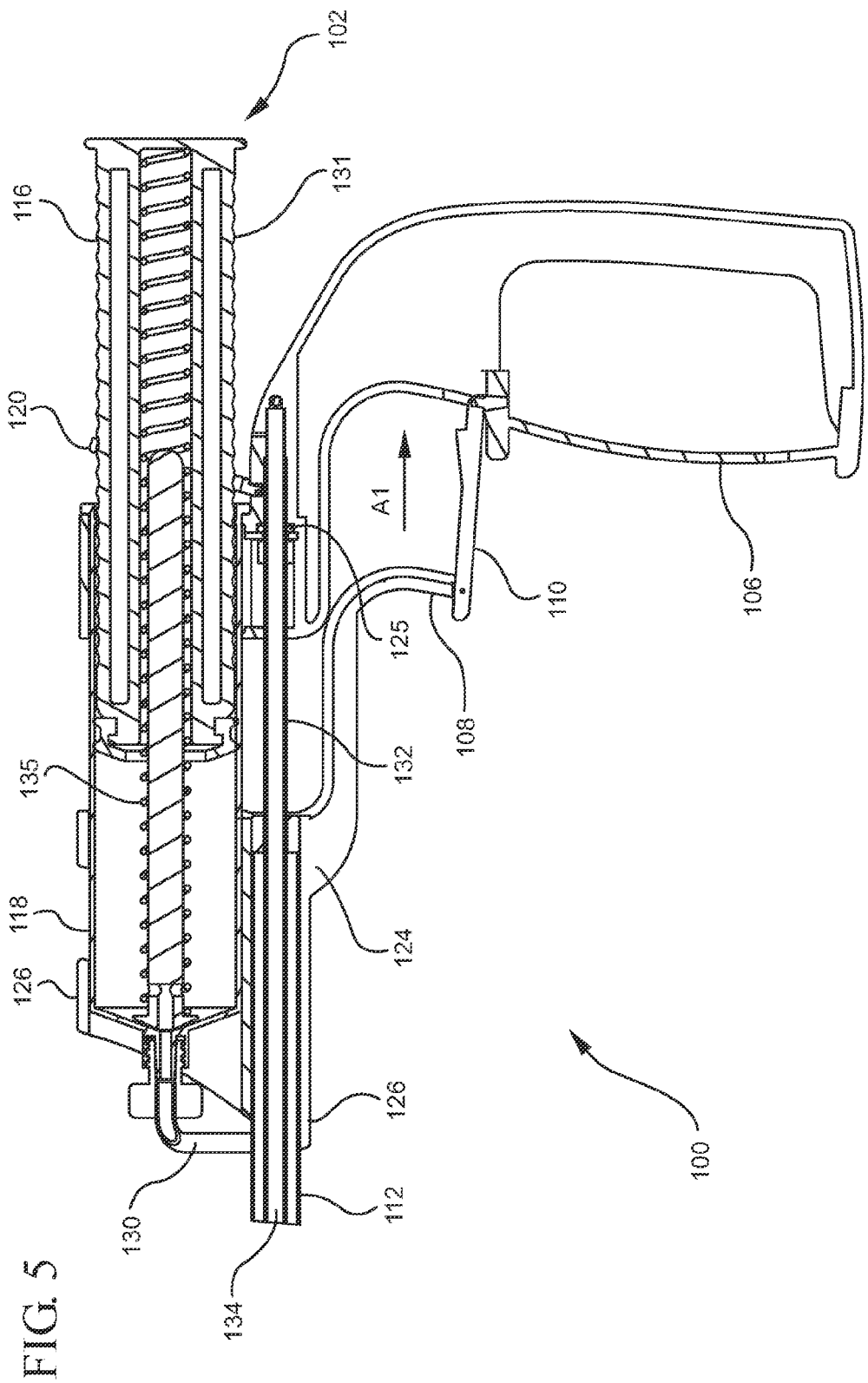
FIG. 5 shows a cross-sectional view of the proximal end of the instrument shown in FIG. 4.

FIG. 5 shows a cross-sectional view of the proximal end 102 of the instrument 100. The handle 106 includes the trigger 108 and the trigger lock 110. As noted above, the trigger lock 110 may be moved into an unlocked position for enabling the trigger 108 to be pulled toward the proximal end 102 of the instrument 100. The trigger 108 includes the leading end 124 that is coupled with the hollow tube 126. As the trigger 108 is pulled toward the proximal end of the instrument in the direction $A_1$, the trigger leading end 124 and the hollow tube 126 pull the outer shaft 112 toward the proximal end 102 of the instrument 100. The instrument 100 includes an O-ring seal 125 that engages the outer surface of the intermediate shaft 132.

In order to inflate the inflatable balloon (not shown), the plunger 116 may be pressed toward the distal end of the instrument for compressing the fluid (e.g. air) located within the plunger barrel 118. The compressed fluid is forced into conduit 130 which, in turn, directs the compressed fluid into an inner shaft 134 for inflating the inflatable balloon. After the plunger 116 has been depressed, plunger locking ring 120 engages the ridges 131 on the outside of the plunger 116 for locking the plunger 116 in place. The balloon will remain inflated as long as the plunger is locked in place. In order to deflate the balloon, the plunger locking ring 120 may be pressed toward the distal end of the instrument 100. After the plunger locking ring 120 is depressed, the plunger locking ring no longer closely engages the ridges 131 on the outer surface of the plunger portion 116, which enables the plunger 116 to move toward the proximal end 102 of the instrument 100. As shown in FIG. 5, the syringe desirably includes a spring 135 that returns the plunger 116 to the extended position. As noted above, the balloon deflates as the plunger 116 returns to the extended position.

As will be described in more detail below, the distal end of the inflatable balloon is attached to the distal end of the inner shaft 134. In one preferred embodiment, the distal end of the inflatable balloon is inverted and the inverted surface of the balloon is attached to the outer surface of the inner shaft 134. In addition, the proximal end of the inflatable balloon is attached to the outer surface of the intermediate shaft 132. After the balloon has been inflated, the intermediate shaft 132 may be advanced distally relative to the distal end of the inner shaft 134. As the intermediate shaft 132 advances distally relative to the inner shaft 134, the shape of the inflated balloon changes. In one embodiment, the inflated balloon initially has a generally spherical shape. After the intermediate shaft 132 is advanced distally, however, the inflated balloon changes shape from a rounder or more spherical shape to a generally flatter or more toroidal shape having a flatter leading surface. The flatter leading surface of the balloon provides a larger surface area for pressing against hemostats such as topically applied hemostats, as will be described in more detail below.

FIG. 6A shows the distal end 104 of the instrument 100, in accordance with one embodiment of the present invention. The instrument 100 includes the outer shaft 112 having a distal end 140 and a central lumen 142 extending from the distal end 140 toward the proximal end of the outer shaft 112. The instrument 100 includes a cartridge connector 144 having a proximal end 146 inserted into the central lumen 142 of the outer shaft 112 and a distal end 148 remote therefrom. The distal end 148 of the cartridge connector 144 has an annular groove 150 formed therein. As will be described in more detail below, the annular groove 150 is adapted to engage a proximal end of a cartridge for connecting the cartridge to the distal end 148 of the cartridge connector 144. The instrument 100 also includes a cartridge connector O-ring seal 152 that desirably forms an air-tight seal between the distal end 148 of the cartridge connector 144 and the outer surface 154 of the intermediate shaft 132. The O-ring seal 152 preferably prevents body or other fluids from entering and contaminating internal portions of the device. The O-ring seal 152 is desirably held in place by retainer wall 155.

The instrument 100 includes the intermediate shaft 132 that extends distally from the distal end 148 of the cartridge connector 144. The instrument 100 also includes the inner shaft 134 that extends distally from the intermediate shaft 132. The intermediate shaft 132 preferably has an internal lumen extending between proximal and distal ends thereof and the inner shaft 134 telescopically slides within the central lumen of the intermediate shaft 132. The intermediate shaft 132 may be selectively moved relative to the inner shaft 134 (e.g. by pressing the deformation slider toward the distal end of the instrument). In one embodiment, the inner shaft 134 includes an opening 156 that is in communication with the inside of the inflatable balloon 160 for selectively inflating and deflating the balloon.

Referring to FIGS. 6A and 6B, the instrument 100 includes the inflatable balloon 160 having a proximal end 162 attached to the outer surface 154 of the intermediate shaft 132 at the distal end of the intermediate shaft. The inflatable balloon 160 also has a distal end 164 that is attached to the outer surface of the inner shaft 134 at the distal end of the inner shaft. The balloon may be made of a wide array of materials used to make medical balloons including elastomers such as polyurethane elastomers and silicone elastomers, and polymers. For example, the balloons may include any of the medical balloons sold by Polyzen, Inc. As shown in FIG. 6B, the distal end 164 of the inflatable balloon 160 is inverted and the inverted surface is attached to the outer surface of the inner shaft 134. The instrument 100 also includes an inner shaft seal 166 that is inserted into the central lumen of the inner shaft 134 at the distal end of the inner shaft.

FIGS. 7A and 7A-1 show how the shape of the inflatable balloon 160 may be changed. Referring to FIG. 7A, as described above, fluid may be passed through the opening 156 in the inner shaft 134 for inflating the balloon 160. The proximal end 162 of the balloon 160 is attached to the intermediate shaft 132 and the distal end 164 of the balloon 160 is inverted, with the inverted surface attached to the distal end of the inner shaft 134.

Referring to FIGS. 7B and 7B-1, after the balloon 160 is inflated, the intermediate shaft 132 is moved toward the distal end 104 of the instrument 100 and relative to the inner shaft 134. As the intermediate shaft 132 is moved distally relative to the inner shaft 134, the shape of the balloon 160 will change. In one preferred embodiment, the inflatable balloon 160 assumes a toroidal shape having a substantially flat leading face 170. Although the present invention is not limited by any particular theory of operation, it is believed that the toroidal shaped balloon 160 and the substantially flat leading face 170 of the balloon provides both a flatter surface area and a larger surface area for more evenly applying pressure to hemostats such as topically applied hemostats, as will be described in more detail below.

In one embodiment, the intermediate shaft 132 has an outside diameter of about 0.2 inches, and a wall thickness of about 0.01 inches. The inner shaft 134 desirably has sufficient clearance to allow it to freely slide within the intermediate shaft. The wall thickness of the inner shaft 134 is preferably about 0.01 inches. In one embodiment, the distal end of the inner shaft 134 projects beyond the distal end of the intermediate shaft 132 by about one inch.

In one embodiment, a cylindrical balloon is attached to the intermediate and inner shafts. The distal end of the balloon is attached or bonded over the distal 0.25 inches of the inner shaft and the proximal end of the balloon is attached or bonded over the distal 0.25 inches of the intermediate shaft. The balloon's attachment at its distal end is such that the balloon is inverted over itself. When the balloon is inflated, the attachment of the distal end of the balloon to the distal end of the instrument is located inside the inflated balloon. In one embodiment, a seal is provided at the distal end of the inner shaft. The inner shaft may include a hole formed in a side wall thereof to allow for inflation and deflation of the balloon.

In one embodiment, a seal, such as an O-ring, may be disposed between the intermediate and inner shafts to prevent leakage when inflating the balloon. The proximal end of the inner shaft may be coupled with a device, such as a syringe, to inflate and deflate the balloon. The proximal ends of the intermediate and inner shafts may be contained within a housing that provides for easy manual control of the shafts for slidably moving the intermediate shaft forward a distance of up to about 0.75 inches. The housing also includes an element for manually inflating and deflating the balloon. The housing may resemble those of other trigger-operated endoscopic devices, such as the EES Proximate Stapler line or the Ethicon Morcellex device.

Referring to FIGS. 8A and 8B, in one embodiment, the instrument 100' includes Velcro®-like barbs or hooks 165' provided at a distal end thereof. As described in more detail herein, the Velcro®-like barbs or hooks 165' are adapted to engage a hemostat for holding the hemostat at the distal end of the instrument during delivery and deployment of the hemostat at a surgical site.

In one embodiment, the instrument does not include a cartridge that holds or covers the hemostat at the distal end of the instrument. In this embodiment, the Velcro®-like hooks or barb perform one of the functions provided by the cartridge so as to hold the hemostat at the distal end of the instrument.

FIG. 9A shows the applicator instrument 100' of FIGS. 8A and 8B after the balloon 160' has been inflated. As shown in FIG. 9A, the leading face 170' of the balloon 160' extends beyond the Velcro®-like hooks or barbs 165'. In FIG. 9B, the intermediate shaft 132' has been advanced distally relative to the inner shaft 134' so as to change the shape of the balloon 160'. As shown in FIG. 9B, the leading face 170' of the balloon is flatter than the leading face of the balloon of FIG. 9A.

Referring to FIG. 10A, in one embodiment of the present invention, a system for the delivery, deployment, and tamponade of hemostats includes a cartridge loader 172 having an upper end 174 including a central opening 176 and a lower end 178 including a support base 180. The upper end 174 of the cartridge loader 172 has a platform 182 that surrounds the central opening 176. The platform 182 is adapted to receive and hold a hemostatic device such as a hemostat patch for loading into a cartridge. A ridge 184 desirably extends around an outer perimeter of the platform 182 for centering and/or holding the hemostat in place over the central opening 176.

Figure 10B:
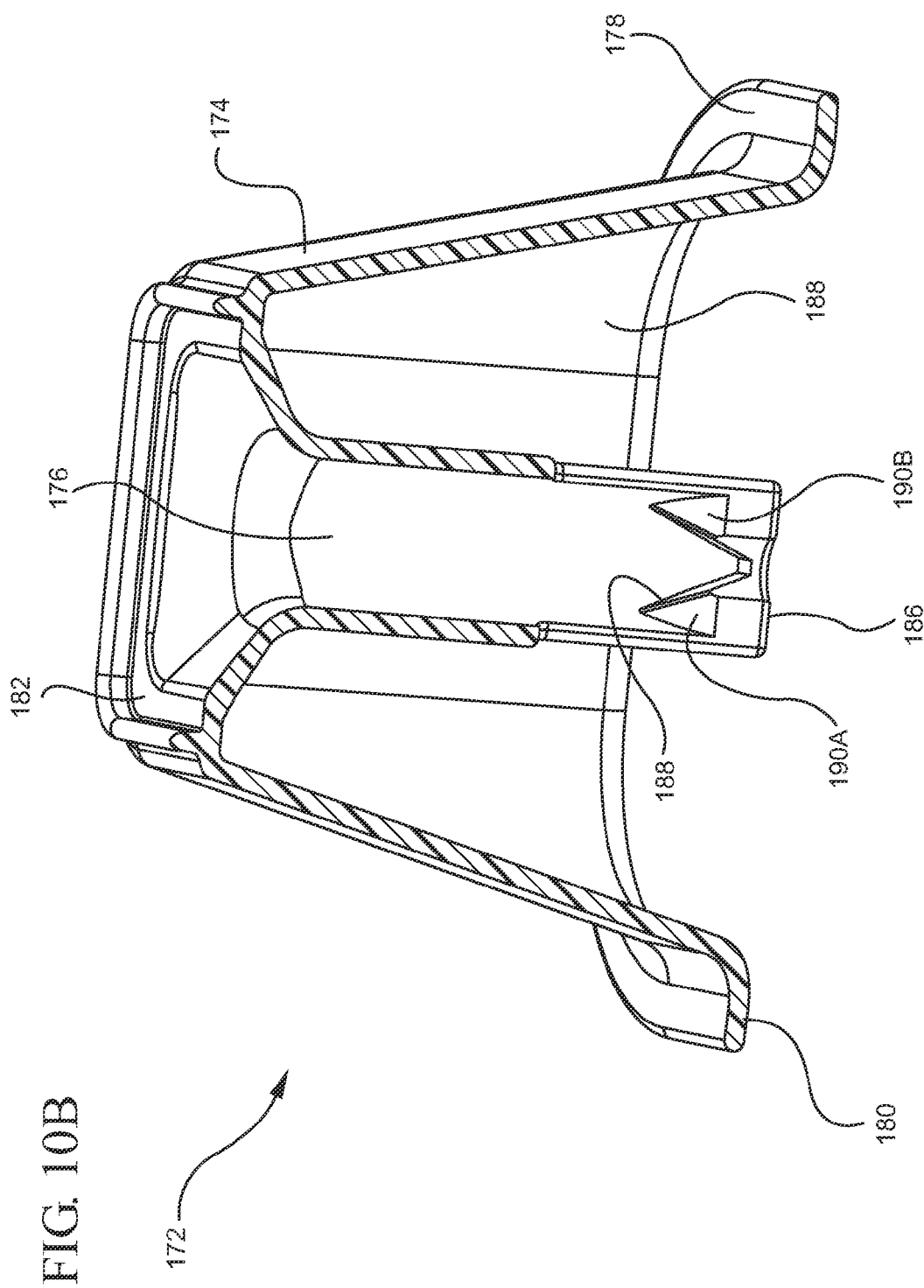

Referring to FIGS. 10B and 10C, the cartridge loader 172 includes the central opening 176 that extends between the upper end 174 and the lower end 178 of the cartridge loader. The central opening 176 has an open end adjacent the platform 182 and a closed end 186 adjacent the base 180. The closed end 186 of the central opening 176 includes a cartridge receiving surface 188 that is designed to receive and support a leading end of a cartridge (not shown). In one embodiment, the cartridge receiving surface 188 includes a pair of projections 190A that are adapted to support the leading end of the cartridge, while minimizing any damage to the seal provided at the leading end of the cartridge. The cartridge receiving surface 188 also maintains the seal end of a cartridge in a closed position as a hemostat is loaded therein, as will be described in more detail below.

Figure 11:
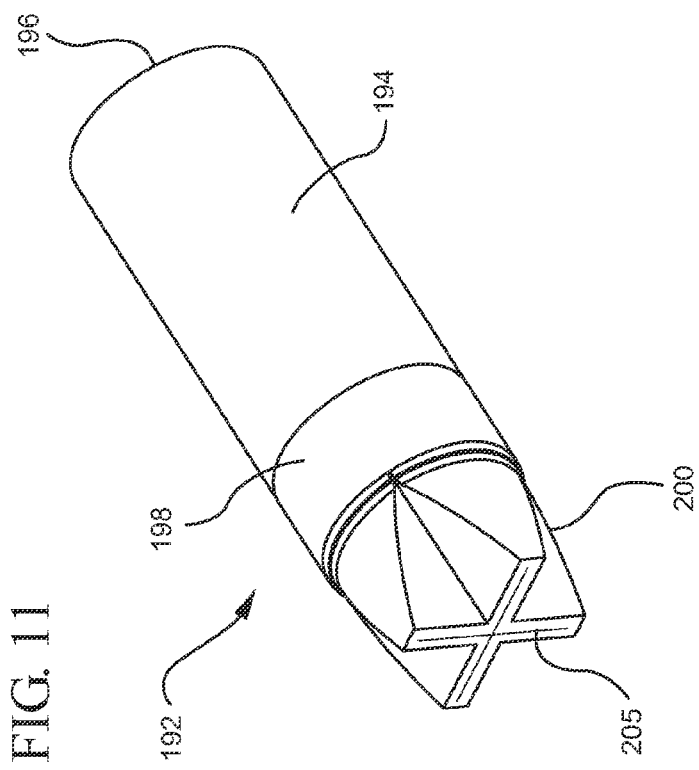
FIG. 11 shows a perspective view of a cartridge having a fluid-resistant seal, in accordance with one embodiment of the present invention.

Referring to FIG. 11, in one embodiment of the present invention, the system includes a cartridge 192 that is loadable into the cartridge loader 172 shown above in FIGS. 9-10B. The cartridge 192 preferably includes a cartridge tube 194 having a proximal end 196 that is open and a distal end 198 that has a fluid-resistant seal. In one embodiment, the fluid-resistant seal 200 is preferably secured over the distal end 198 of the cartridge tube 194. In the embodiment shown in FIG. 11, the fluid-resistant seal is a four-way duck bill valve, although other conventional fluid-resistant seals may be used. The distal-most end of the four-way duck bill valve has a cruciform shape with elongated slits or openings 205 provided at the distal end of the cruciform-shaped structure for enabling a hemostatic device to pass therethrough.

Figure 12:
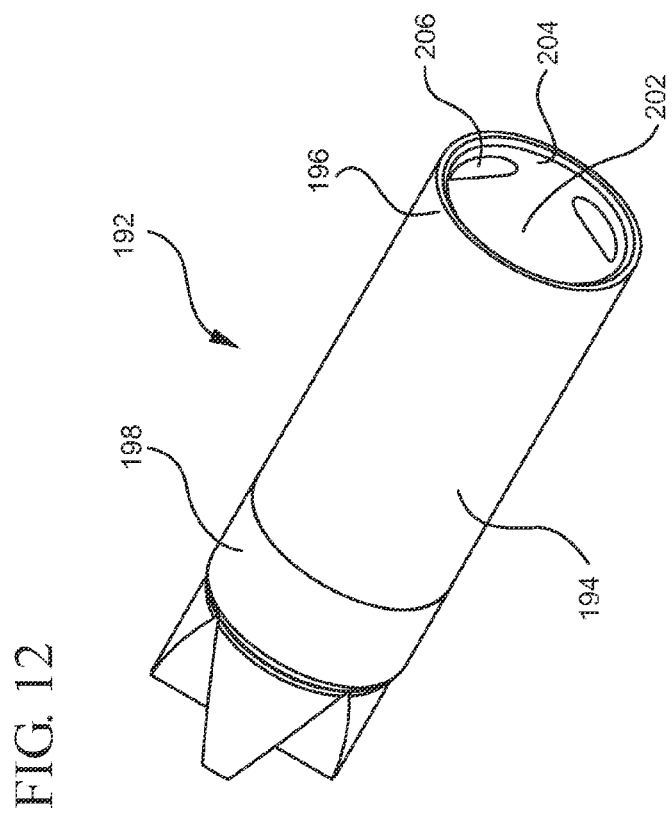
FIG. 12 shows another perspective view of the cartridge shown in FIG. 11.

Referring to FIG. 12, in one embodiment, the proximal end 196 of the cartridge tube 194 has a central opening 202 that extends from the proximal end 196 toward the distal end 198 thereof. The inner surface 204 of the cartridge tube 194 desirably has one or more projections 206 extending therefrom. The projections 206 preferably engage the annular groove 150 provided at the distal end 148 of the cartridge connector 144 for enabling the cartridge to form a snap-fit connection with the distal end of the instrument 100 (FIG. 1). The central opening 202 is preferably sized and shaped to enable a hemostat such as a medical textile or a topically applied hemostat to be loaded therein, as will be described in more detail below.

Figure 13:
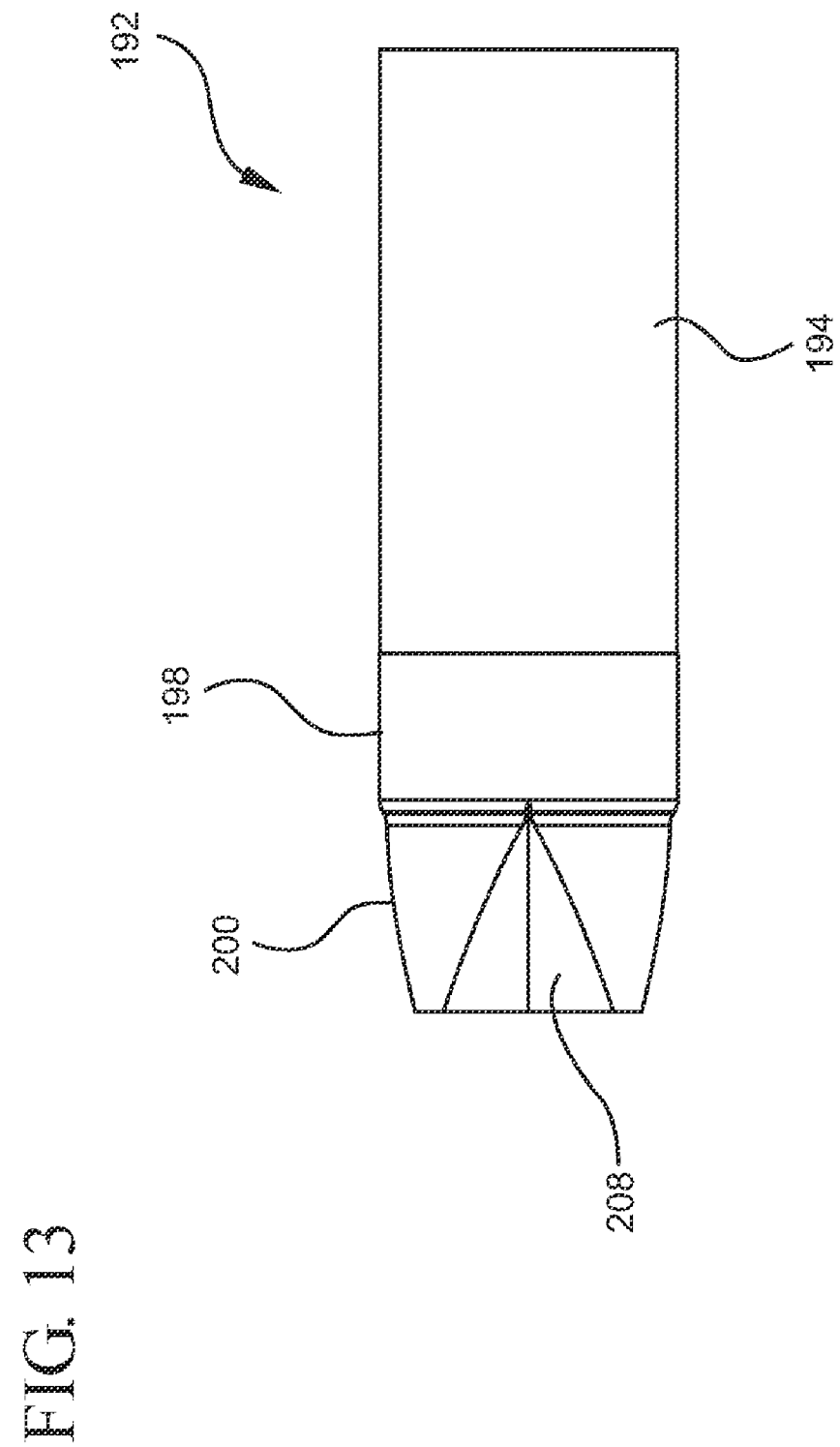
FIG. 13 shows a front elevational view of the cartridge shown in FIGS. 11 and 12.

Referring to FIG. 13, the cartridge 192 includes the fluid-resistant valve 200 secured over the distal end 198 of the cartridge tube 194. The distal end of the fluid-resistant valve 200 includes one or more depressions 208 adapted to sit atop the projections 190A, 190B provided at the closed end 186 of the central opening 176 of the cartridge loader 172 (FIG. 10B). Referring to FIGS. 10B and 13, the apexes of the projections 190A, 190B preferably abut against the distal-most end 198 of the cartridge tube 194 for supporting the cartridge tube 194 within the central opening 176, without damaging the fluid-resistant valve.

Figure 14B:
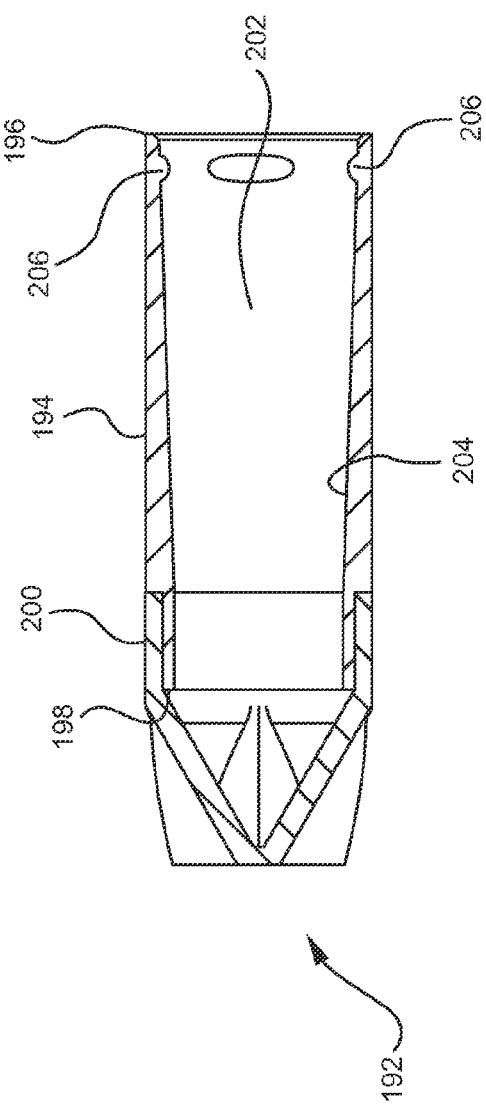
FIG. 14B shows another cross-sectional view of the cartridge shown in FIGS. 11-13.
Figure 14A:
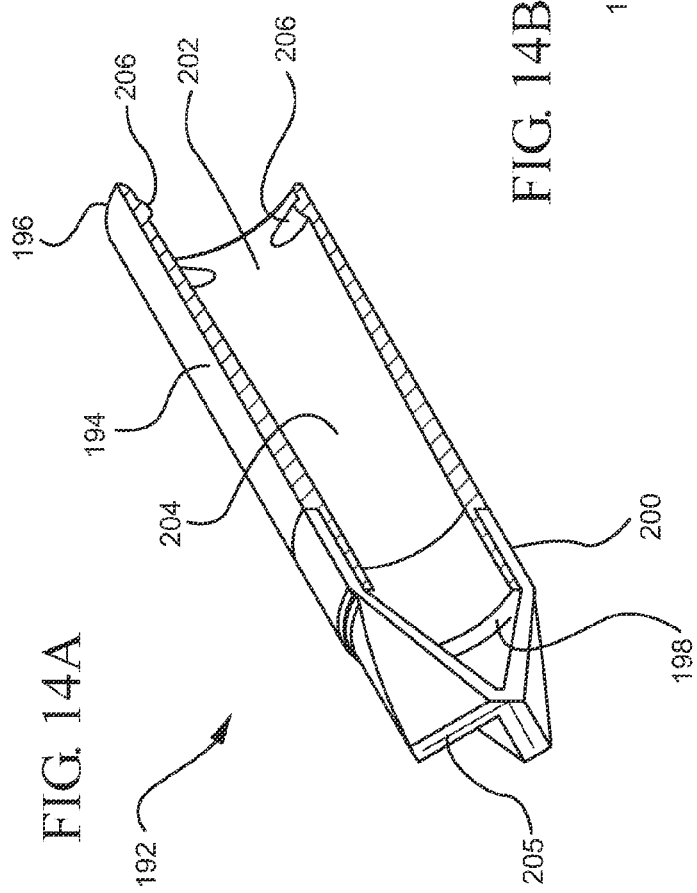
FIG. 14A shows a cross-sectional view of the cartridge shown in FIGS. 11-13.

Referring to FIGS. 14A and 14B, in one embodiment the cartridge tube 194 has a distal end 198 and the fluid-resistant seal 200 is secured over the distal end thereof. The seal 200 includes elongated openings or slits 205 that may be opened to enable a hemostat to pass therethrough. The cartridge tube 194 includes the central opening 202 that desirably extends from the proximal end 196 to the distal end 198 of the cartridge tube 194. The inner surface 204 of the cartridge tube 198 includes a series of projections 206 that enable the proximal end 196 of the cartridge tube 194 to be snap-fit connected to a cartridge connector (FIGS. 6A and 6B) located at the distal end of the instrument.

In one embodiment, the cartridge tube is a cylinder with an outer diameter of about 0.2-0.5 inches, and more preferably about 0.394 inches (10 mm), a wall thickness of about 0.02 inches, and a length of about 1.5 inches. In other embodiments, the dimensions indicated above may vary and still fall within the scope of the present invention. The distal end of the cartridge desirably has a pierceable, punctureable, or traversable seal. The proximal end of the cartridge tube may be open and may have a beveled edge resembling a funnel-like feature.

In one embodiment, the outer shaft of the instrument has an outer diameter of about 0.2-0.5 inches, and more preferably about 0.394 inches (10 mm) and a wall thickness of about 0.02 inches. The outer shaft is preferably positioned concentrically about the intermediate and inner shafts of the applicator instrument. The distal end of the outer shaft desirably has an element for concentrically engaging and securing the proximal end of the cartridge. In one embodiment, the distal end of the outer shaft is normally positioned about 1.5 inches proximal to the distal tip of the inner shaft. The outer shaft is adapted to slide axially toward the proximal end of the instrument.

The distal tip of the inner shaft may have barbed or Velcro®-like hooks that protrude distally. The barbs or hooks may be used to pick up the hemostat for loading the hemostat into a cartridge. In one embodiment, the length of the outer shaft (the "working length") is about 10-15 inches, and more preferably about 13 inches (33 cm).

Figure 15:
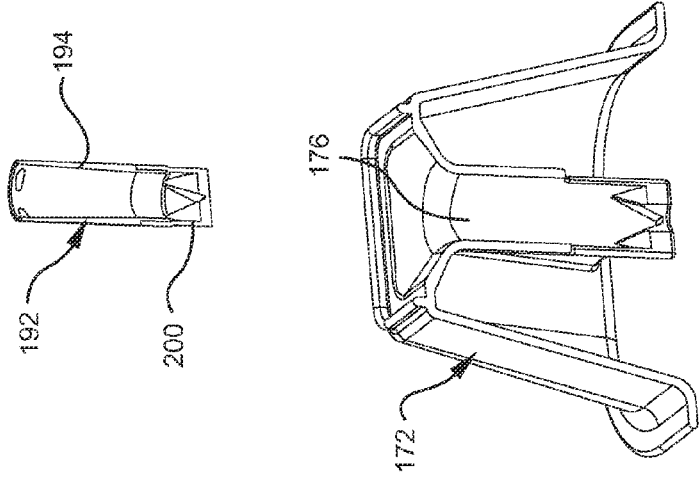
FIG. 15 shows the cartridge of FIGS. 11-14B being loaded into the cartridge loader of FIG. 9.
Figure 16:
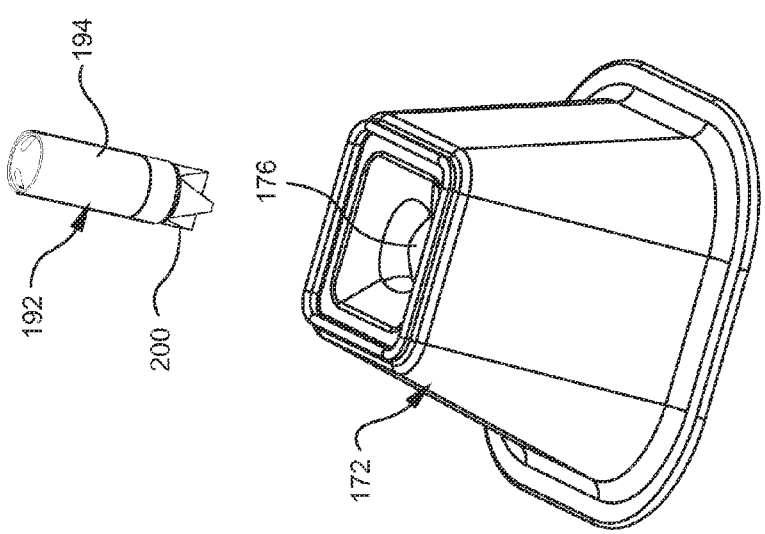
FIG. 16 shows cross-sectional views of the cartridge and the cartridge loader shown in FIG. 15.

Referring to FIGS. 15 and 16, in one embodiment of the present invention, the cartridge 192 is preferably loaded into the cartridge loader 172 by aligning the fluid-resistant seal 200 at the lower end of the cartridge tube 194 with the central opening 176 of the cartridge loader 172. The cartridge 192 may then be slid into the central opening until the lower end of the cartridge engages the cartridge supporting surfaces 188 (FIG. 10A).

Figure 17A:
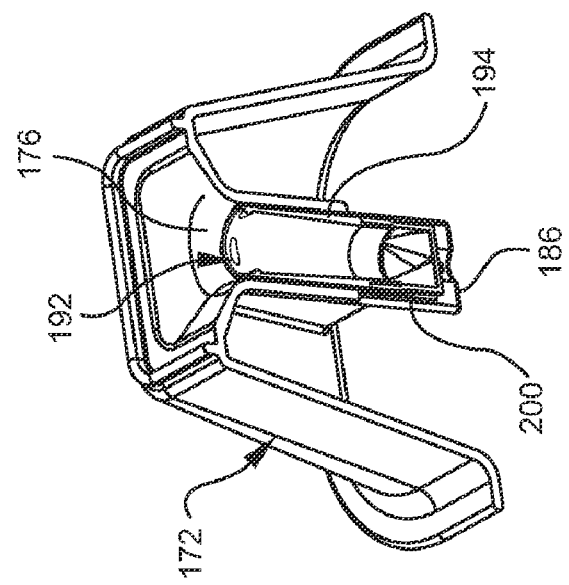
FIG. 17A shows a perspective view of the cartridge loader of FIG. 15 after the cartridge of FIG. 11 has been loaded therein.
Figure 17B:
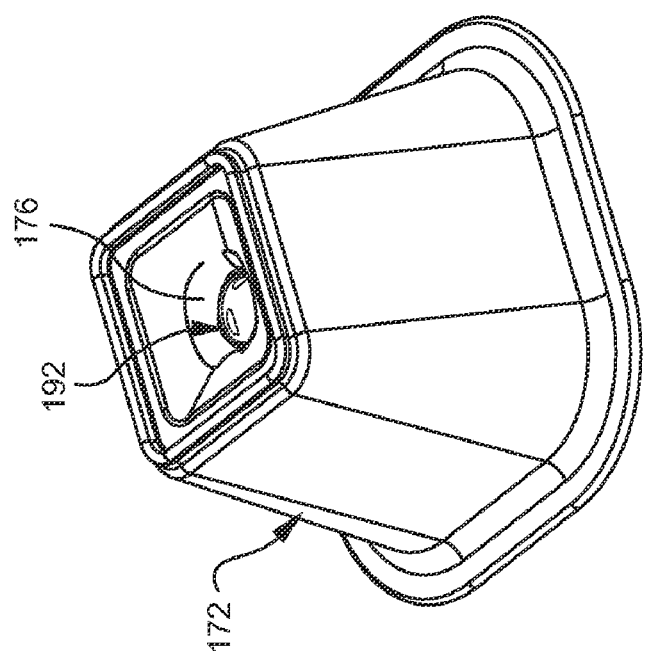
FIG. 17B shows a cross-sectional view of the cartridge loader and cartridge shown in FIG. 17A.

FIGS. 17A and 17B show the cartridge loader 172 after the cartridge 192 has been loaded into the central opening 176. Referring to FIG. 17B, the fluid-resistant seal 200 at the lower end of the cartridge 192 desirably engages the cartridge supporting projections (not shown) provided at the closed end 186 of the central opening. As described above, the projections preferably support the distal end of the cartridge tube 194, while minimizing the likelihood of damage to the fluid-resistant seal 200.

Figure 18:
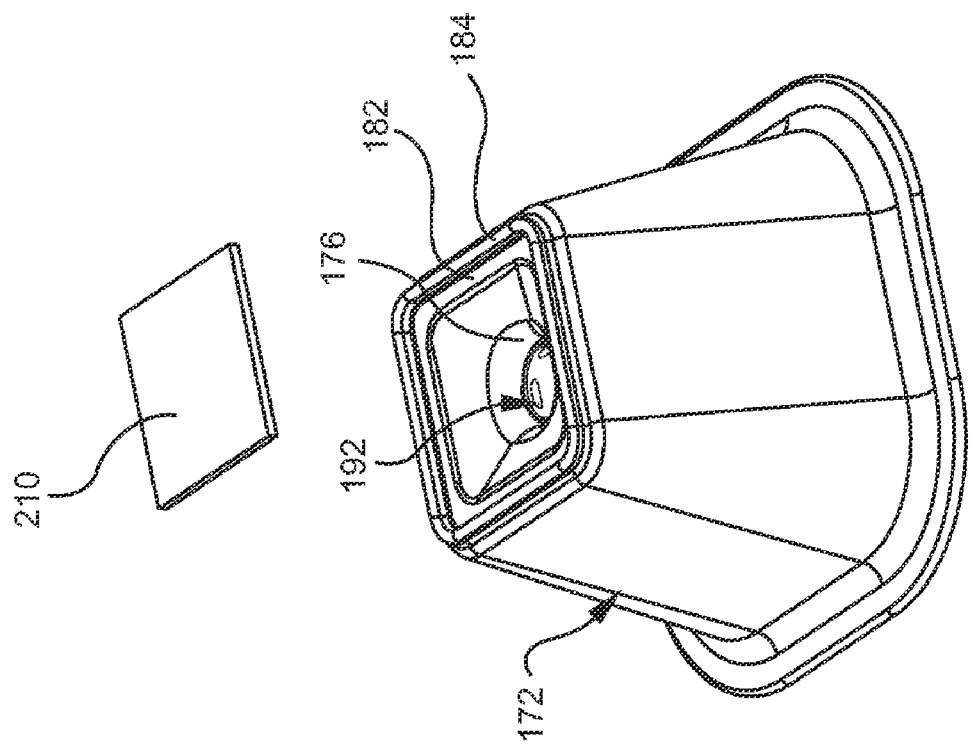

Referring to FIG. 18, in one embodiment of the present invention, after the cartridge 192 is positioned within the cartridge loader 172, a hemostat such as a hemostat patch 210 is placed atop the patch supporting platform 182 and within the ridge 184 surrounding the outer periphery of the platform 182. The hemostat patch is preferably centered over the central opening 176 provided at the top of the cartridge loader 172.

Figure 19B:
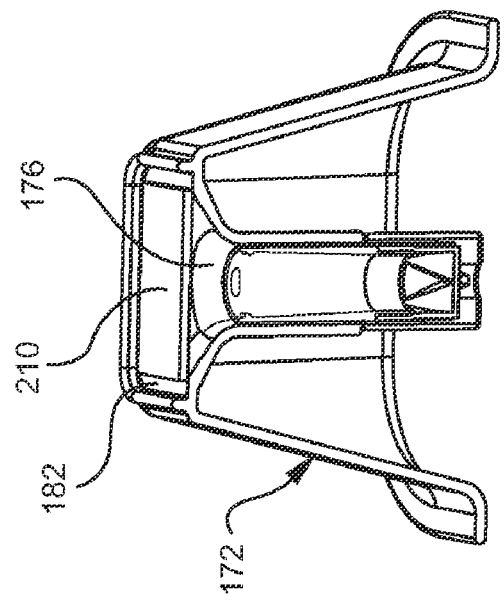
Figure 19A:
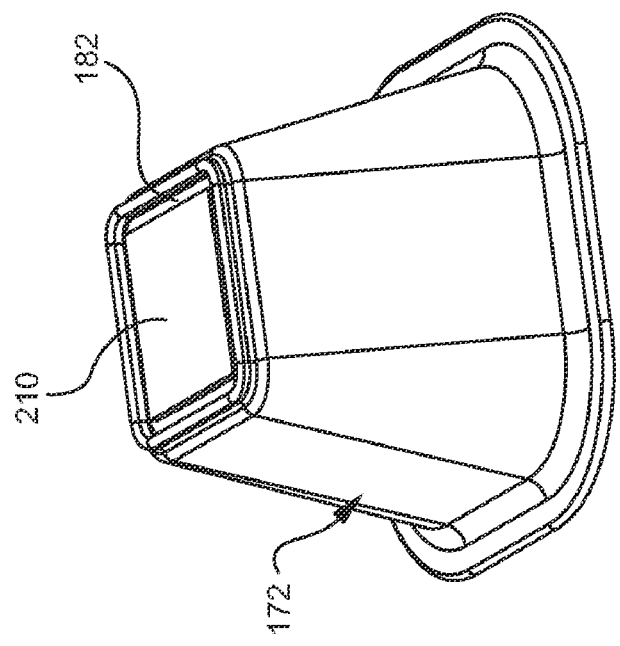

FIGS. 19A and 19B show the hemostat patch 210 positioned atop the platform 182 of the cartridge loader 172. As shown in FIG. 19B, the hemostat patch 210 overlies the proximal end of the cartridge tube 194 and the central opening 176 of the cartridge loader 172.

Figure 20:
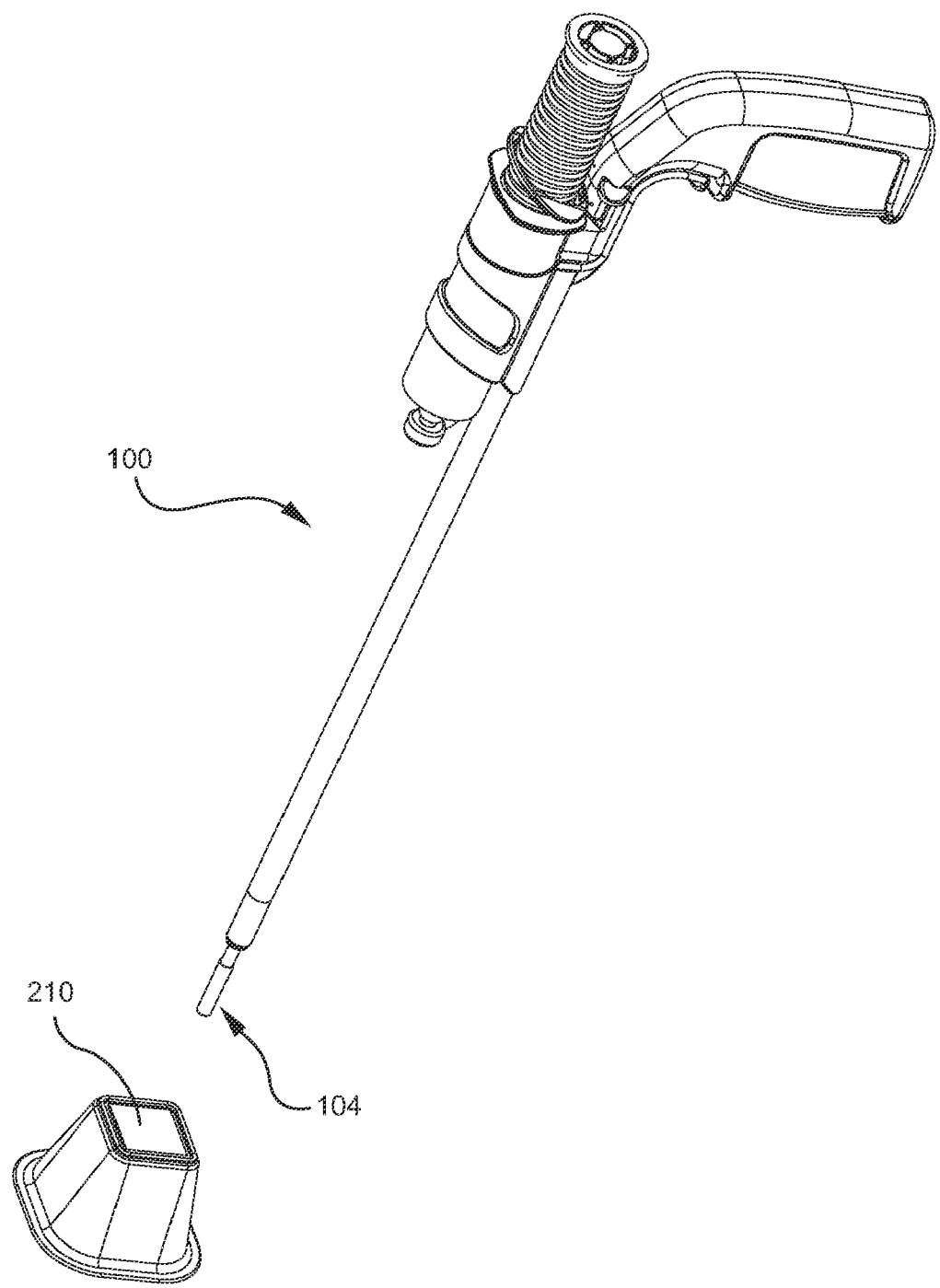

Referring to FIG. 20, in one embodiment of the present invention, the hemostat patch 210 is loaded onto the distal end of the instrument 100 by first aligning the distal end 104 of the instrument 100 with the hemostat patch 210, which in turn is centered atop the cartridge loader.

FIG. 21 shows the distal end 104 of the instrument 100 aligned over the hemostat patch 210 provided atop the cartridge loader 172. The instrument 100 includes the outer shaft 112 and the cartridge connector 144 secured to the distal end of the outer shaft 112. The distal-most end of the cartridge connector 144 includes an annular groove 150 adapted to engage projections provided at a proximal end of the cartridge (not shown). The instrument 100 includes intermediate shaft 132 and inner shaft 134 that extends from the distal-most end of the intermediate shaft 132. The instrument also includes the inflatable balloon 160 having its proximal end secured to the distal end of the intermediate shaft 132 and its distal end secured to the distal end of the inner shaft 134.

Figure 22A:
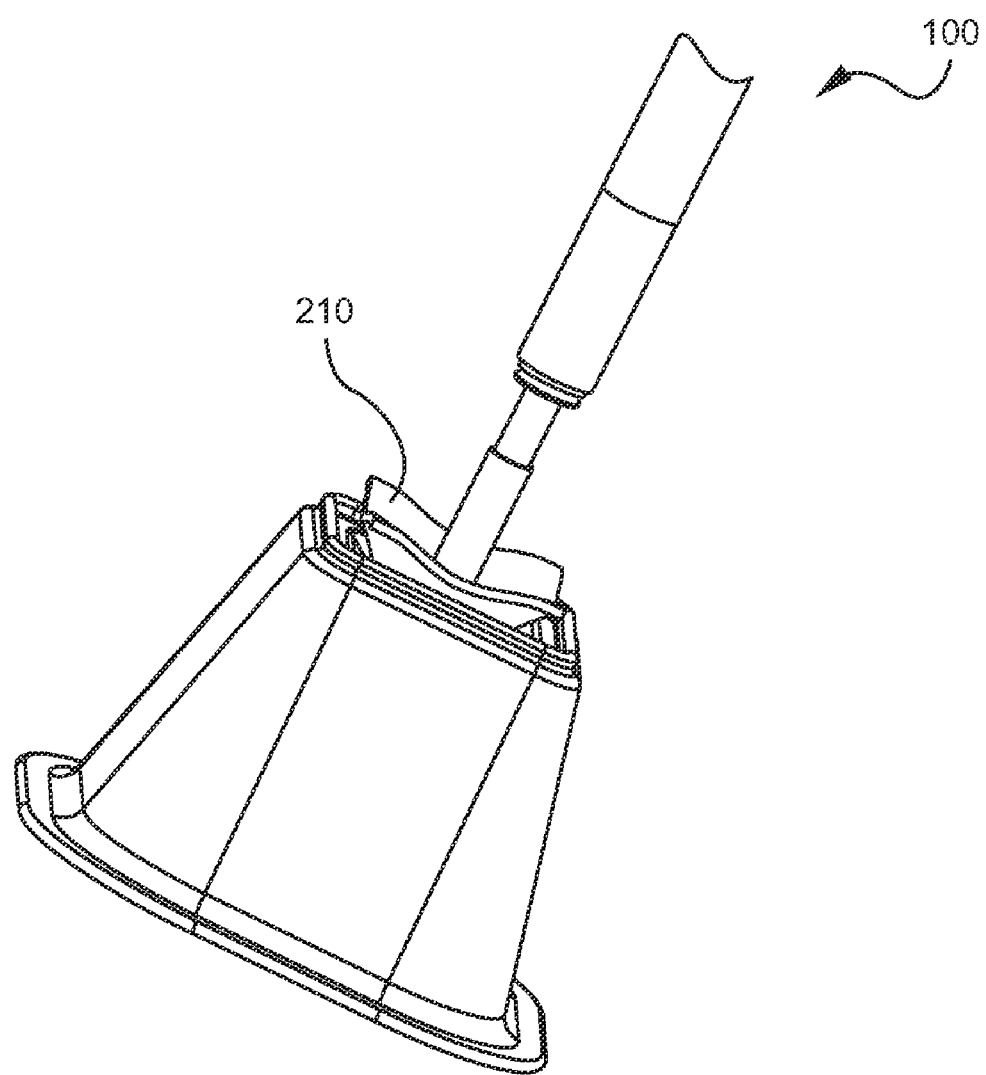
Figure 22B:
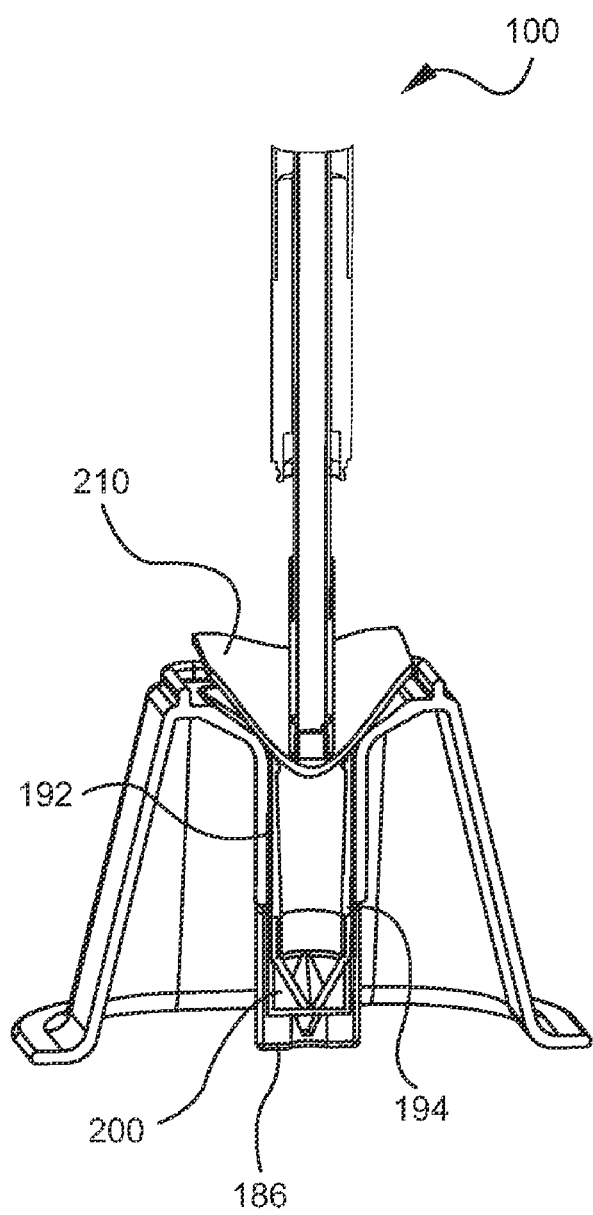

Referring to FIGS. 22A and 22B, the hemostat patch 210 is forced into the opening at the proximal end of the cartridge tube 194 by abutting the distal-most end of the instrument 100 against the hemostat patch 210. As shown in FIG. 22B, the distal-most end of the instrument 100 forces the hemostat patch 210 into the cartridge tube 194 and toward the fluid-resistant seal 200 at the distal end of the cartridge 192.

Figure 23:
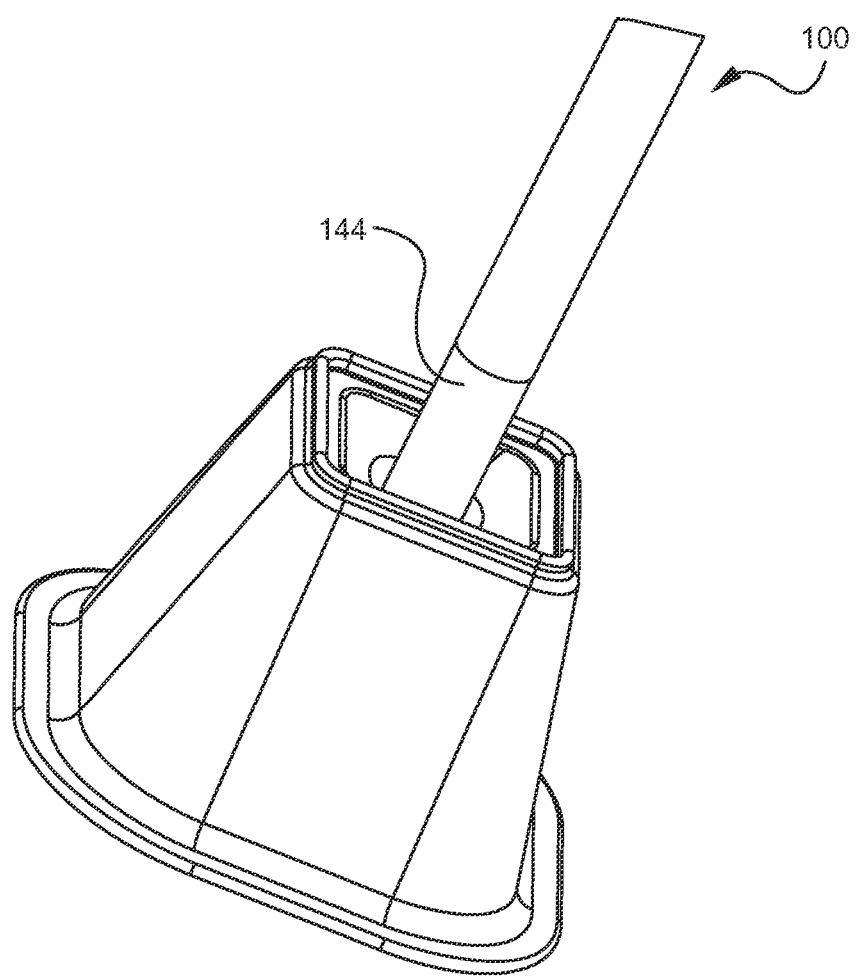
Figure 24:
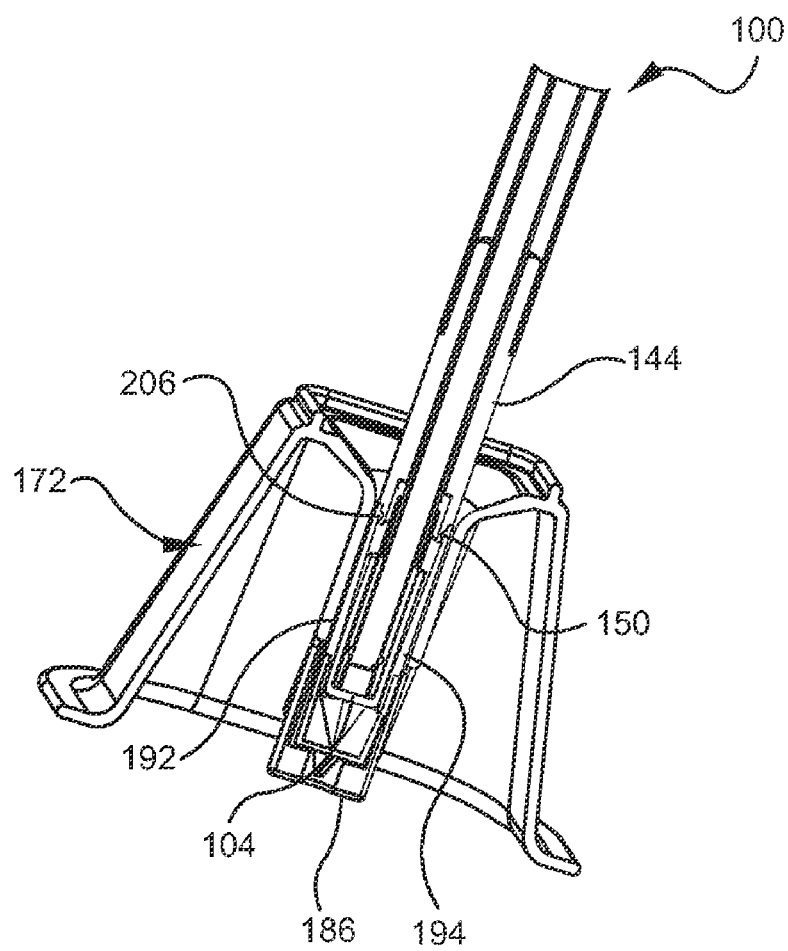

FIGS. 23 and 24 show the instrument 100 after the hemostat patch has been advanced into the cartridge and a snap-fit connection is formed between the cartridge 192 and the cartridge connector 144. As shown in FIG. 24, the distal end of the instrument 100 has been advanced to the closed end 186 of the central opening of the cartridge loader 172. As the distal end 104 moves toward the closed end 186 of the central opening, the hemostat patch 210 is forced into the opening in the cartridge tube 194. The annular groove 150 at the distal end of the cartridge connector 144 preferably forms a snap-fit connection with the projections 206 adjacent the proximal end of the cartridge tube 194.

Figure 25:
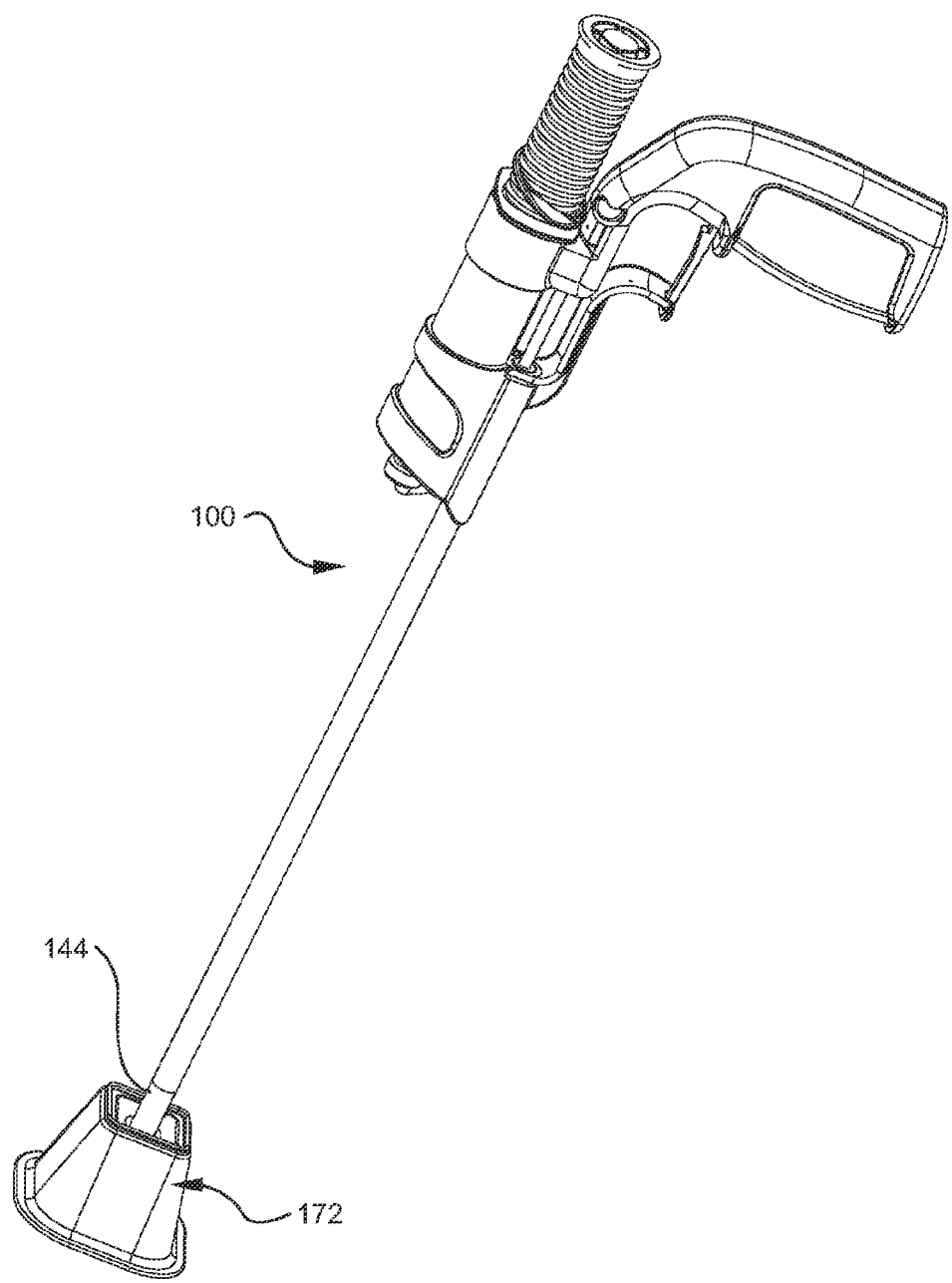

Referring to FIG. 25, after the hemostat patch is loaded into the cartridge opening and a snap-fit connection is formed between the cartridge and the cartridge connector 144, the distal end of the instrument 100 may be removed from the central opening of the cartridge loader 172.

Figure 26:
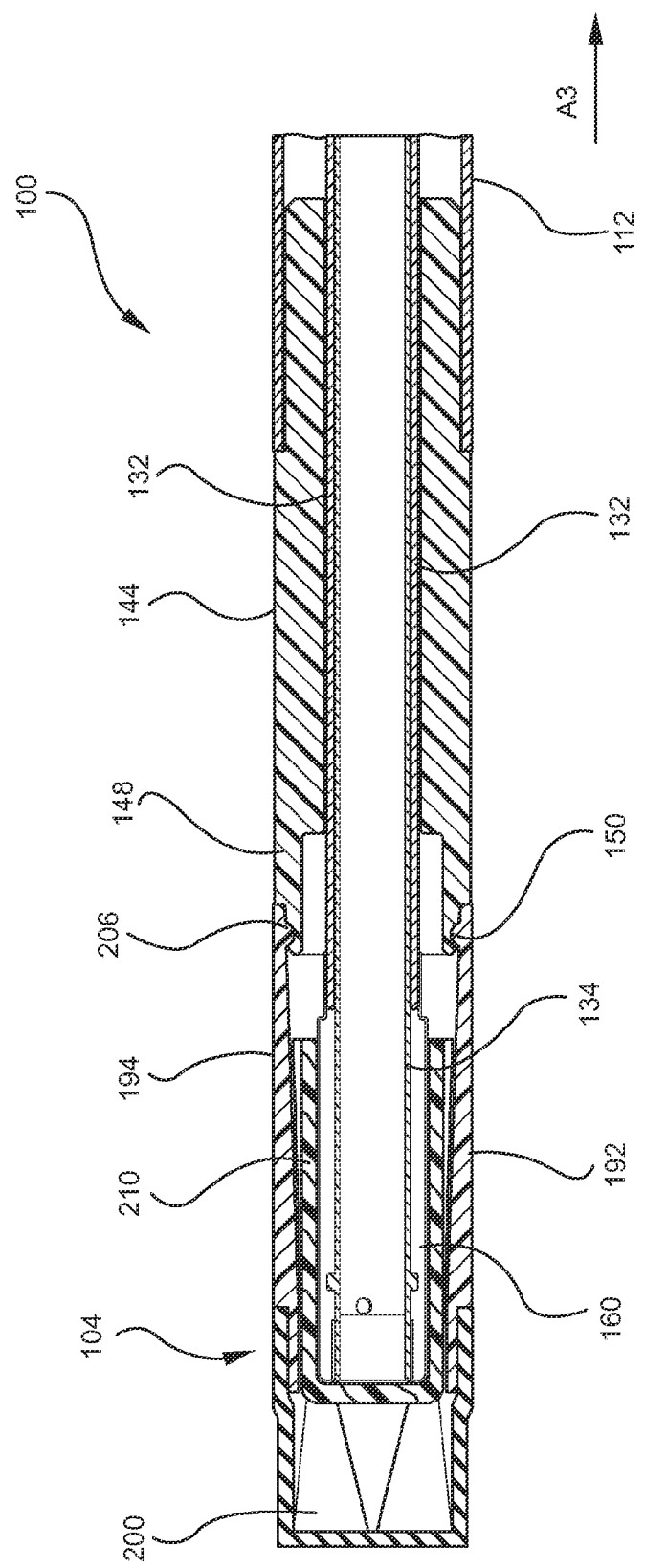
FIG. 26 shows the distal end of the instrument shown in FIGS. 1-2, 6A, and 6B with a hemostat and a cartridge connected to a distal end of the instrument.

FIG. 26 shows the distal end 104 of the instrument 100 after the hemostat patch 210 and the cartridge 192 have been loaded onto the distal end 104 of the instrument. As shown in FIG. 26, the projections 206 at the proximal end of the cartridge tube 194 engage the annular groove 150 at the distal end 148 of the cartridge connector 144. The balloon 160 is deflated and is located between the hemostat patch 210 and the outer surface of inner shaft 134. The fluid-resistant seal 200 at the distal-most end of the instrument 100 preferably maintains a moisture-free environment within the cartridge 192 to prevent moisture or fluids (e.g. bodily fluids) from prematurely contacting the hemostat patch.

In one embodiment, the hemostat patch 210 is delivered from the distal-most end of the instrument 100 by moving the outer shaft 112 toward the proximal end of the instrument 100 in the direction indicated by axis $A_3$. As the outer shaft 112 moves toward the proximal end of the instrument relative to the intermediate shaft 132 and the inner shaft 134, the cartridge 192 is pulled over the intermediate shaft 132 and the inner shaft 134 and toward the proximal end of the instrument through the snap-fit connection between the cartridge connector 144 and the proximal end of the cartridge. As the cartridge 192 is pulled toward the proximal end of the instrument, the hemostat patch 210 breaches the fluid-resistant seal 200 located at the distal end of the cartridge 192.

Figure 27A:
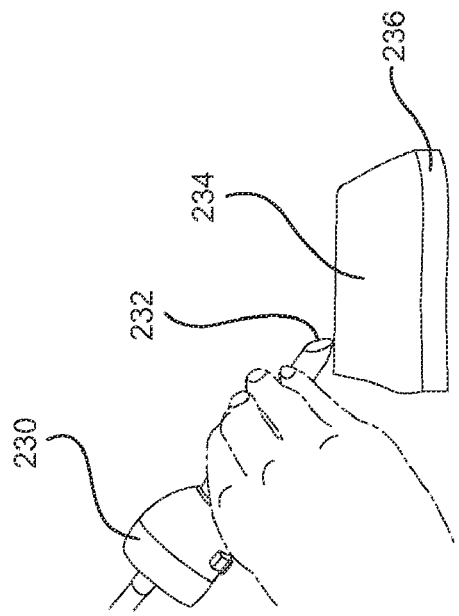
FIGS. 27A-27M show a method for the delivery, deployment and tamponade of a hemostat, in accordance with one embodiment of the present invention.

FIGS. 27A-27M show a method of delivering, deploying and tamponading a hemostat, in accordance with one embodiment of the present invention. Referring to FIG. 27A, after the hemostat and the cartridge have been loaded onto the distal end of an applicator instrument as shown in FIG. 26, the distal end of the instrument is passed through a trocar tube 230. The distal end 232 of the trocar tube 230 is desirably passed through an opening in a body, with the distal end 232 aimed towards a target site 234 on the tissue 236.

Figure 27B:
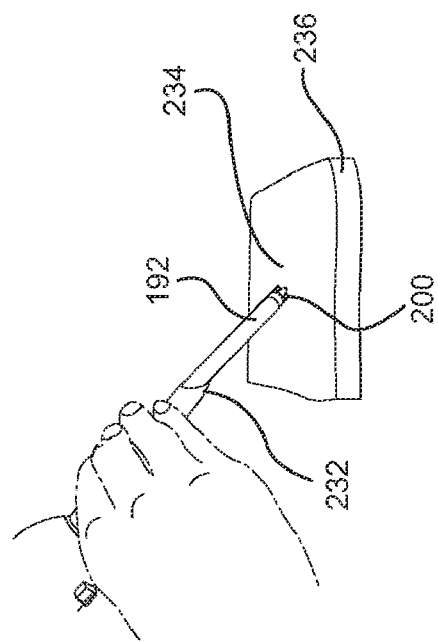

Referring to FIG. 27B, the cartridge 192 attached to the distal end of the applicator instrument is passed through an opening at the distal end 232 of the trocar until the fluid-resistant seal 200 abuts against the target site 234 on the tissue 236. The fluid-resistant seal may be preferably made of a flexible material such as rubber so as to minimize damage to the tissue. FIG. 27C shows the fluid-resistant seal 200 at the distal end of the cartridge 192 abutting against the target site 234 on the tissue 236.

Figure 27D:
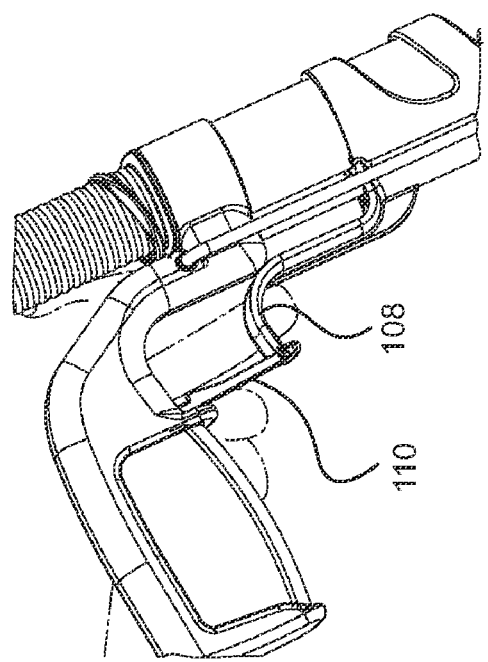
Figure 27C:
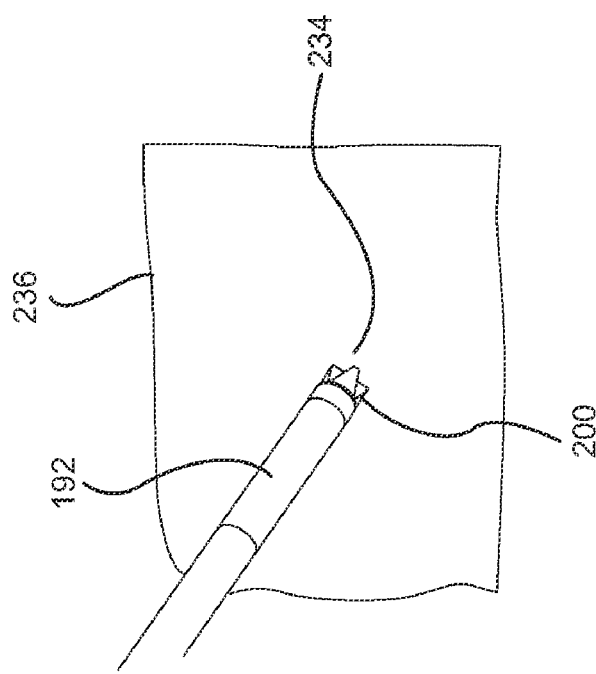
Figure 27F:
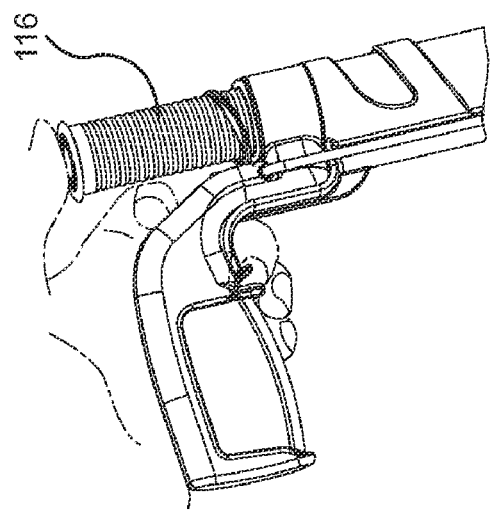
Figure 27E:
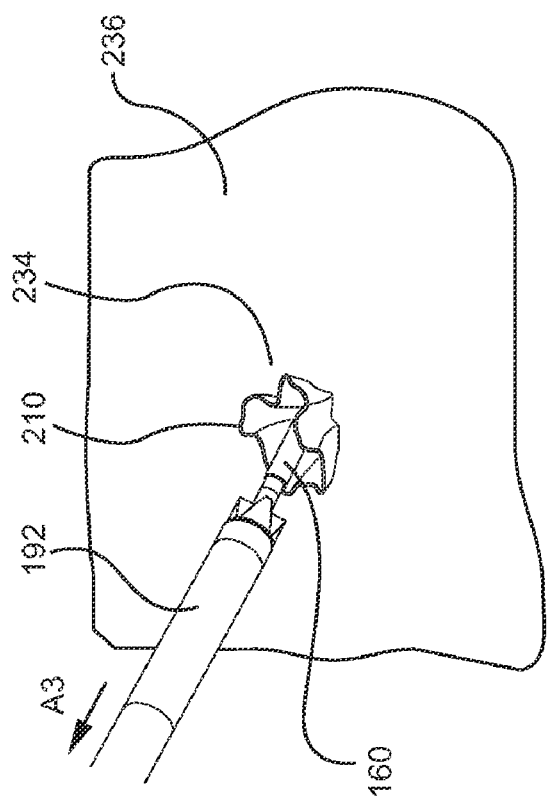

Referring to FIGS. 27D and 27E, the trigger lock 110 may be moved to the unlocked positioned for enabling the trigger 108 to be pulled. As the trigger 108 is pulled, the outer shaft 112 and the cartridge 192 are pulled toward the proximal end of the instrument in the direction indicated by axis $A_3$ so as to deliver the hemostat 210 to the target site 234 on the tissue 236. As shown in FIG. 27E, the balloon 160 provided at the distal end of the instrument 100 remains deflated.

Figure 27G:
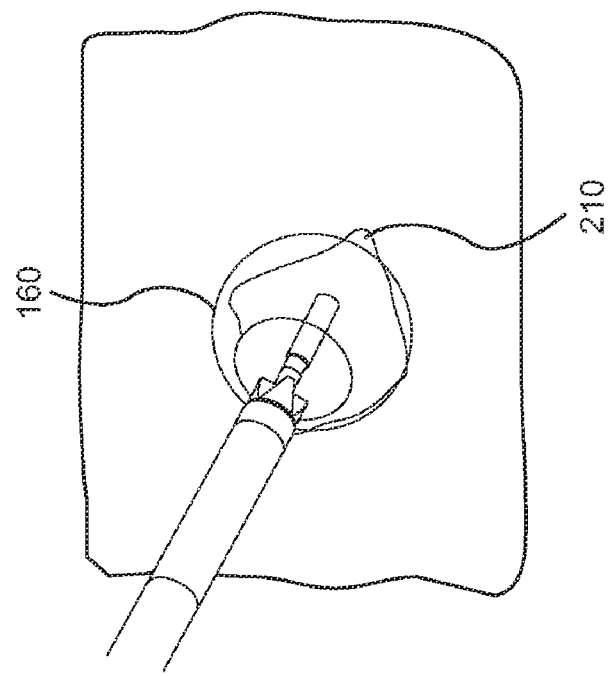
Figures 1, 27G:
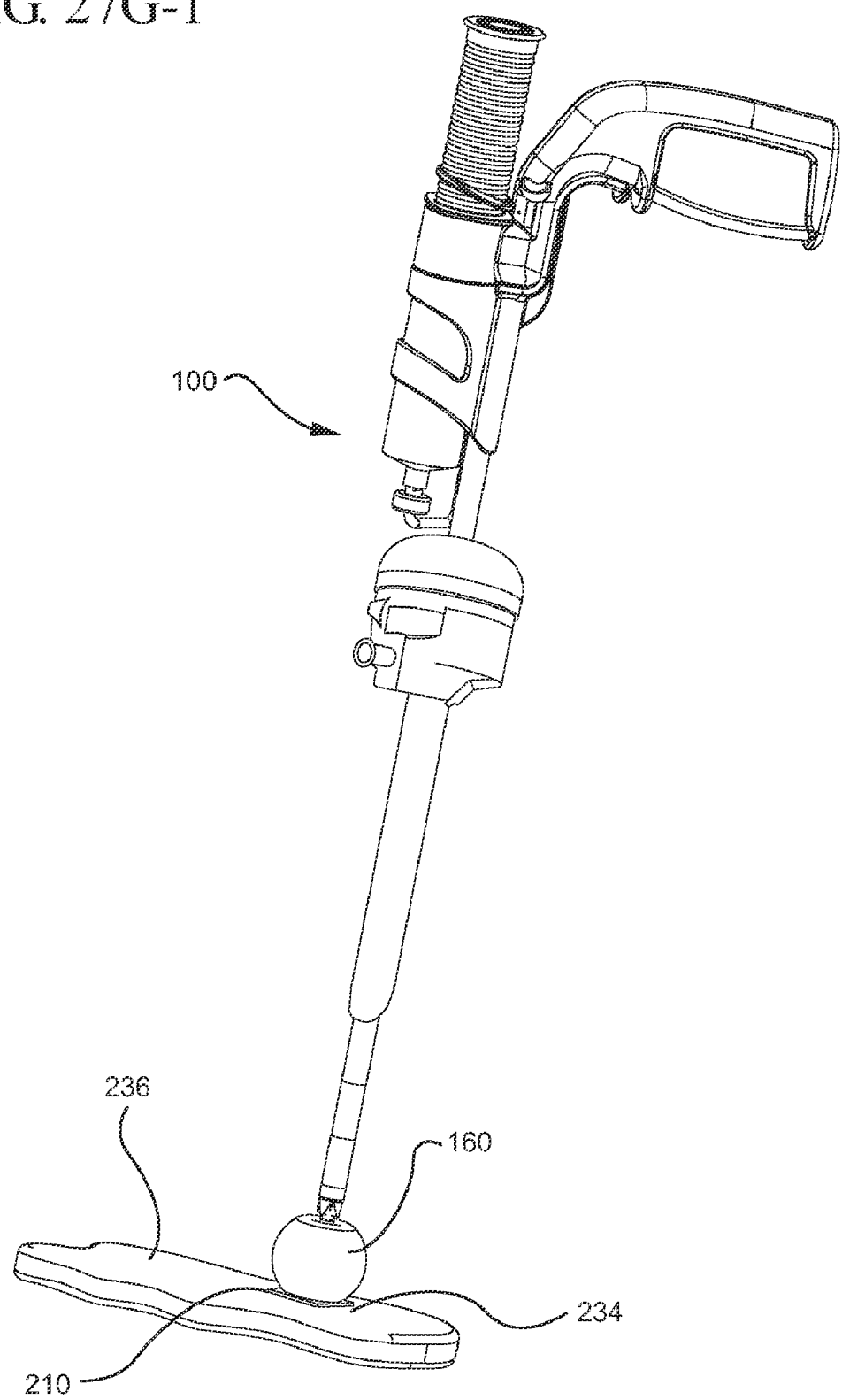
Figures 2, 27G:
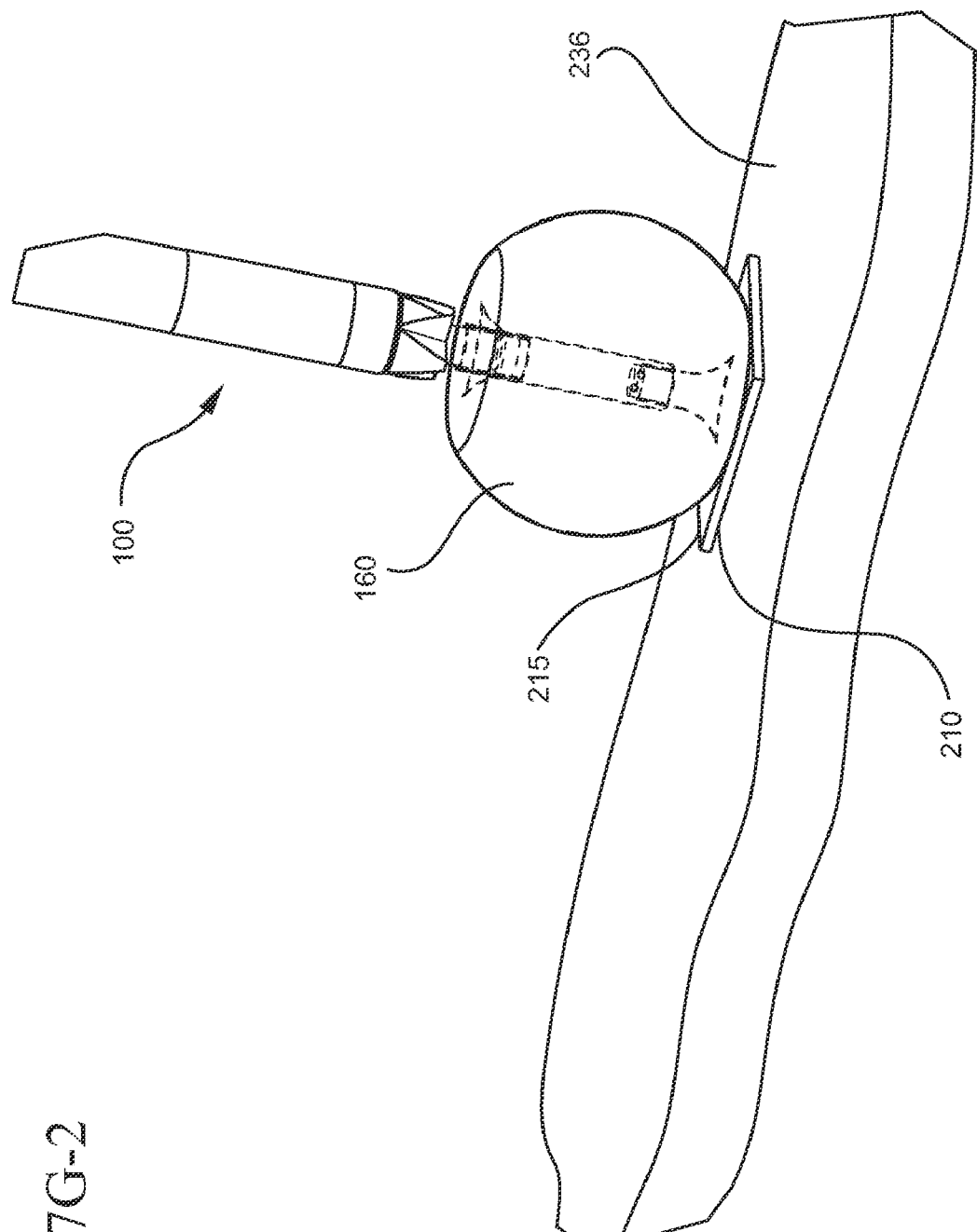

Referring FIGS. 27F and 27G, the syringe plunger 116 is depressed for forcing air into the inner shaft for inflating the balloon 160. In one embodiment, the balloon 160 is transparent so that the hemostat 210 and the surgical site may be continuously observed through the inflated balloon 160.

Figure 27H:
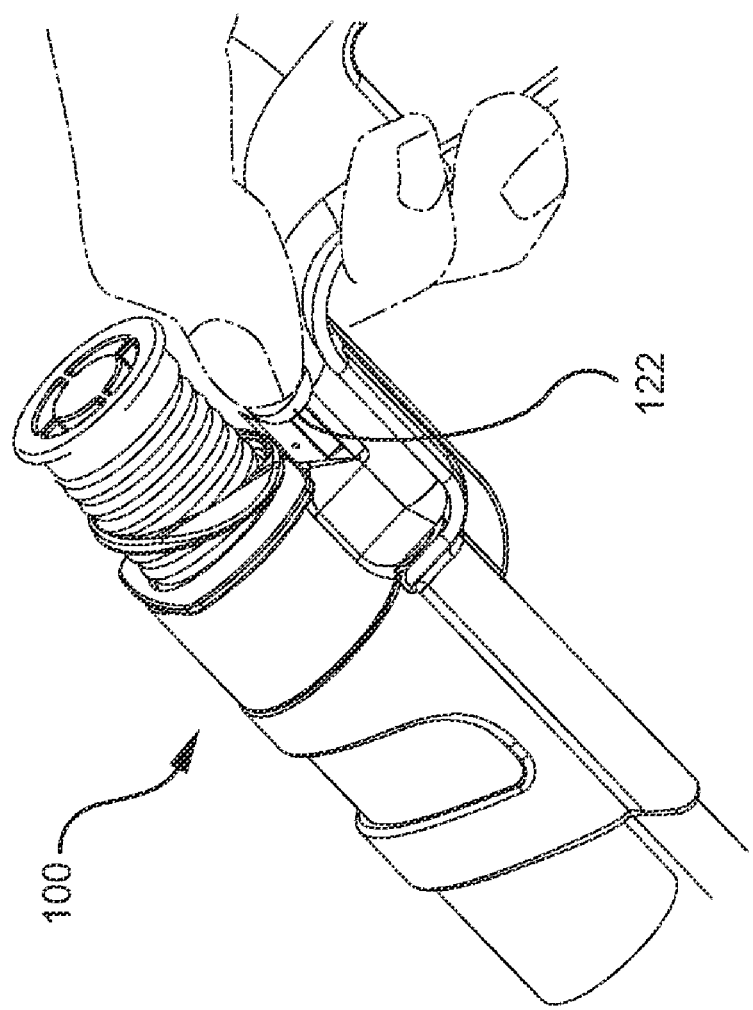
Figure 27I:
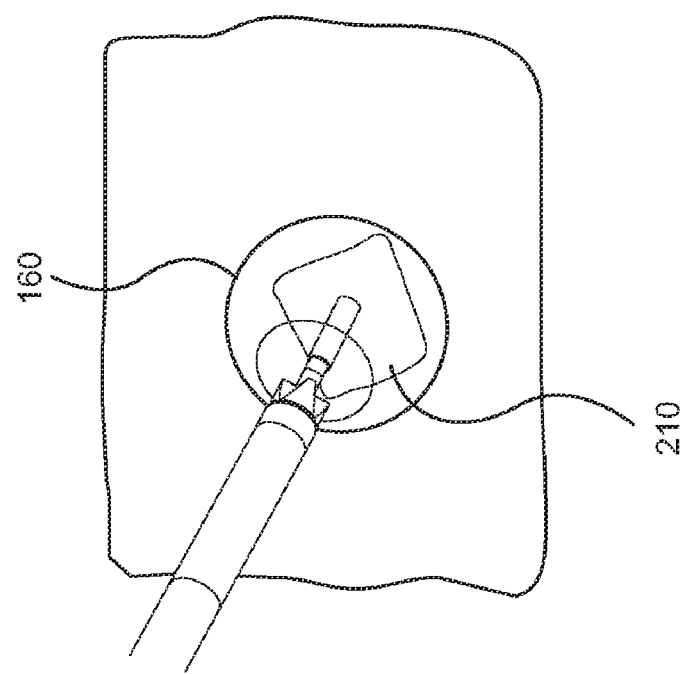
Figures 1, 27I:
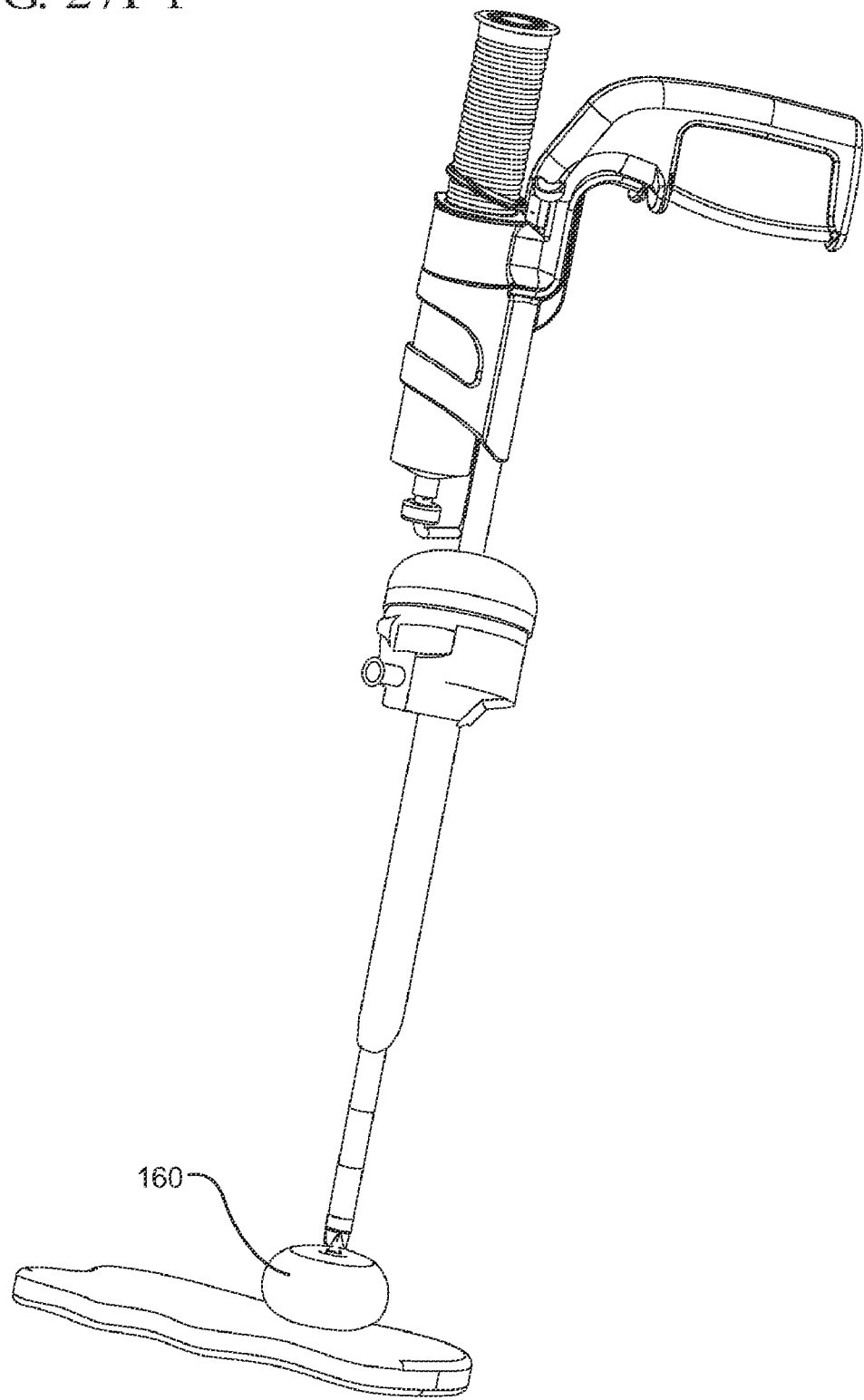
Figures 2, 27I:
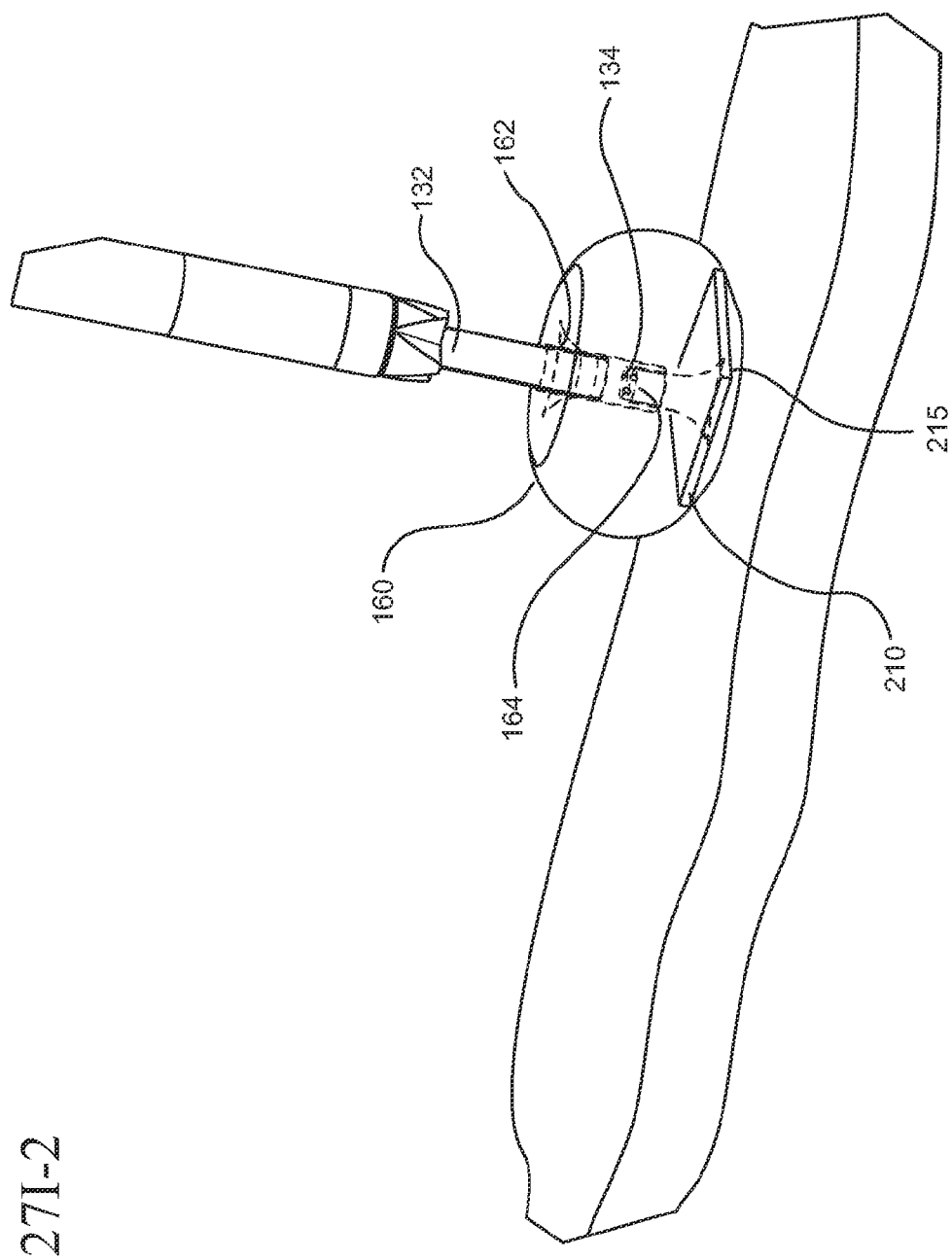

Referring to FIGS. 27H-27I, the deformation slider 122 may be pressed toward the distal end of the instrument 100 for changing the shape of the inflated balloon 160. As the deformation slider 122 is advanced, the distal end of the intermediate shaft moves distally relative to the distal end of the inner shaft. As the intermediate and inner shafts move relative to one another, the shape of the inflated balloon 160 becomes flatter. In particular, the leading face of the inflated balloon becomes flattened for providing more surface area contact with the hemostat 210. Tamponade pressure is applied by the leading face of the inflated balloon 160 for a period of time to stop bleeding at the desired tissue location. In one embodiment, the inflated balloon 160 is transparent so that the surgical site may be continuously observed through the balloon. In one embodiment, the tamponade pressure is applied for approximately 1-5 minutes, and more preferably approximately 2-3 minutes. In other embodiments, tamponade pressure is applied until the bleeding is stopped or is under control.

FIGS. 27G-1 and 27G-2 show other views of the inflated balloon 160 shown in FIG. 27G. Referring to FIG. 27G-1, the distal end of the instrument 100 has delivered and deployed the hemostat patch 210 to the desired site 236 atop tissue 234. Referring to FIG. 27G-2, the leading face of the balloon 160 engages the hemostat patch 210. However, the peripheral edges 215 of the hemostat patch 210 are not engaged by the leading face of the inflated balloon 160. This may be due, in part, to the substantially spherical shape of the balloon shown in FIG. 27G-2.

Referring to FIGS. 27I-1 and 27I-2, in order to flatten the leading face of the inflated balloon 160, the intermediate shaft 132 is moved distally relative to the inner shaft 134. As shown in FIG. 27I-2, the proximal end 162 of the balloon is secured to the distal end of the intermediate shaft 132 and the distal end 164 of the balloon 160 is secured to the distal end of the inner shaft 134. Thus, as the intermediate shaft moves distally relative to the inner shaft 132, the shape of the balloon 160 attached to the two shafts will flatten. As shown in FIG. 27I-2, the leading face of the inflated balloon 160 assumes a flatter shape and covers a larger area so as to fully engage the hemostat patch 210 including the peripheral edges 215 of the hemostat patch.

Figure 27K:
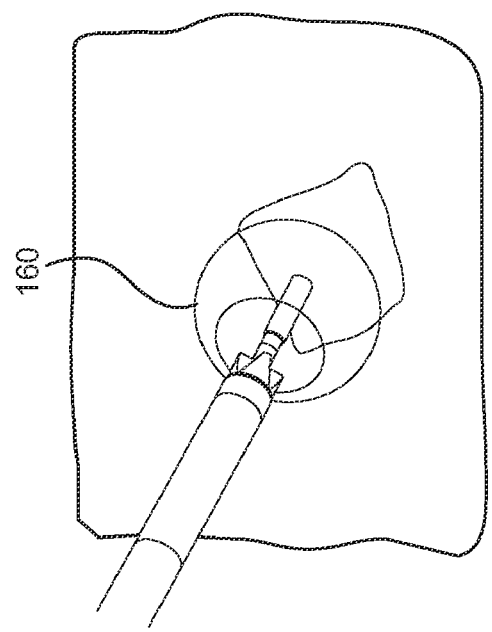
Figure 27J:
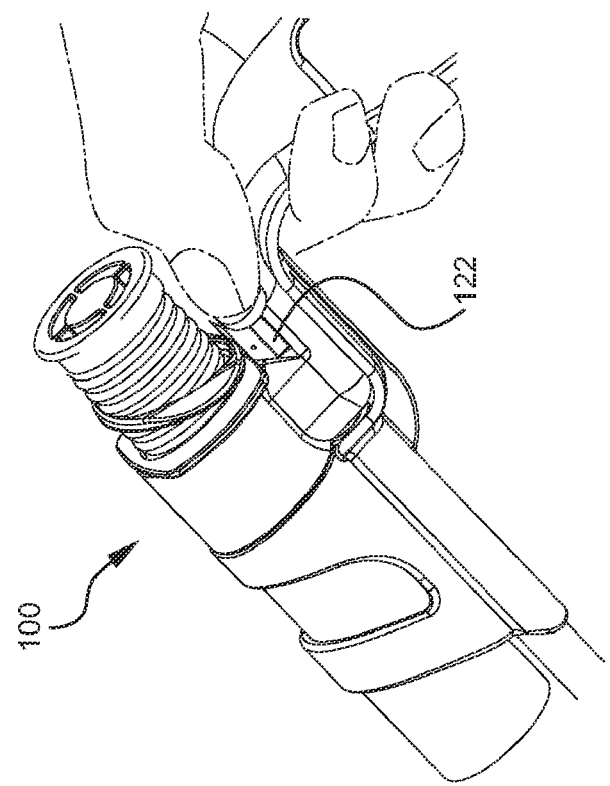

Referring to FIGS. 27J and 27K, after the tamponade pressure has been applied to the hemostat patch for a desired period of time (e.g. sufficient to stop bleeding), the deformation slider 122 may be retracted toward the proximal end of the instrument 100. As the deformation slider 122 retracts, the intermediate shaft moves proximally relative to the inner shaft to return the balloon 160 to the substantially spherical shape shown in FIG. 27K.

Figure 27M:
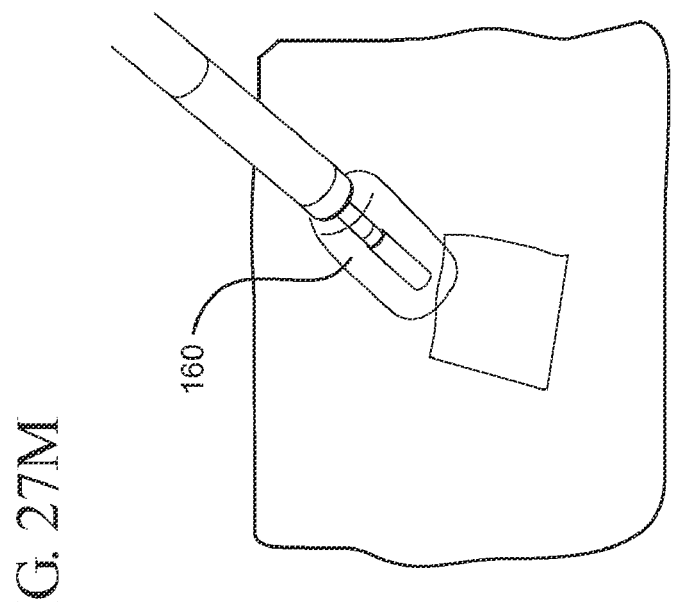
Figure 27L:
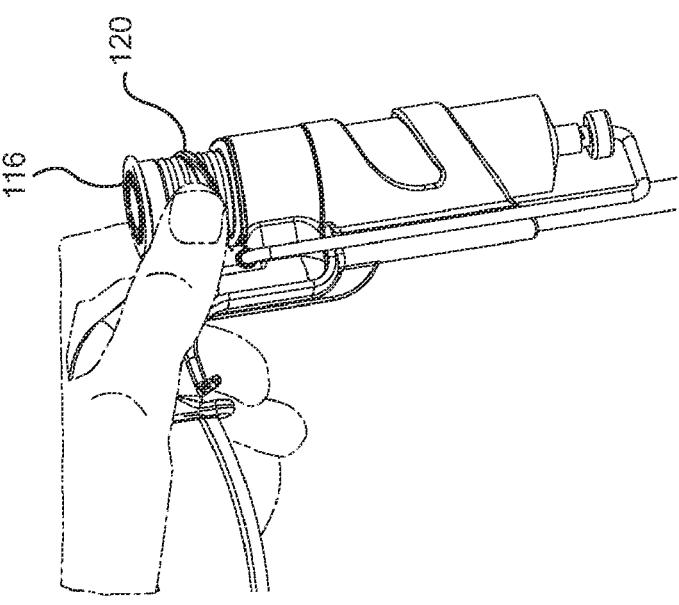

Referring to FIGS. 27L and 27M, after the balloon 160 is returned to the spherical shape, the balloon may be deflated by engaging the syringe plunger locking ring 120 so as to allow the plunger 116 to move proximally for releasing fluid from the balloon 160. The deflated balloon and the distal end of the applicator instrument may then be retracted from the trocar. After the instrument has been retracted, the hemostat patch preferably remains in place atop the tissue for stopping and/or controlling bleeding, or for other desired functions.

Figure 28:
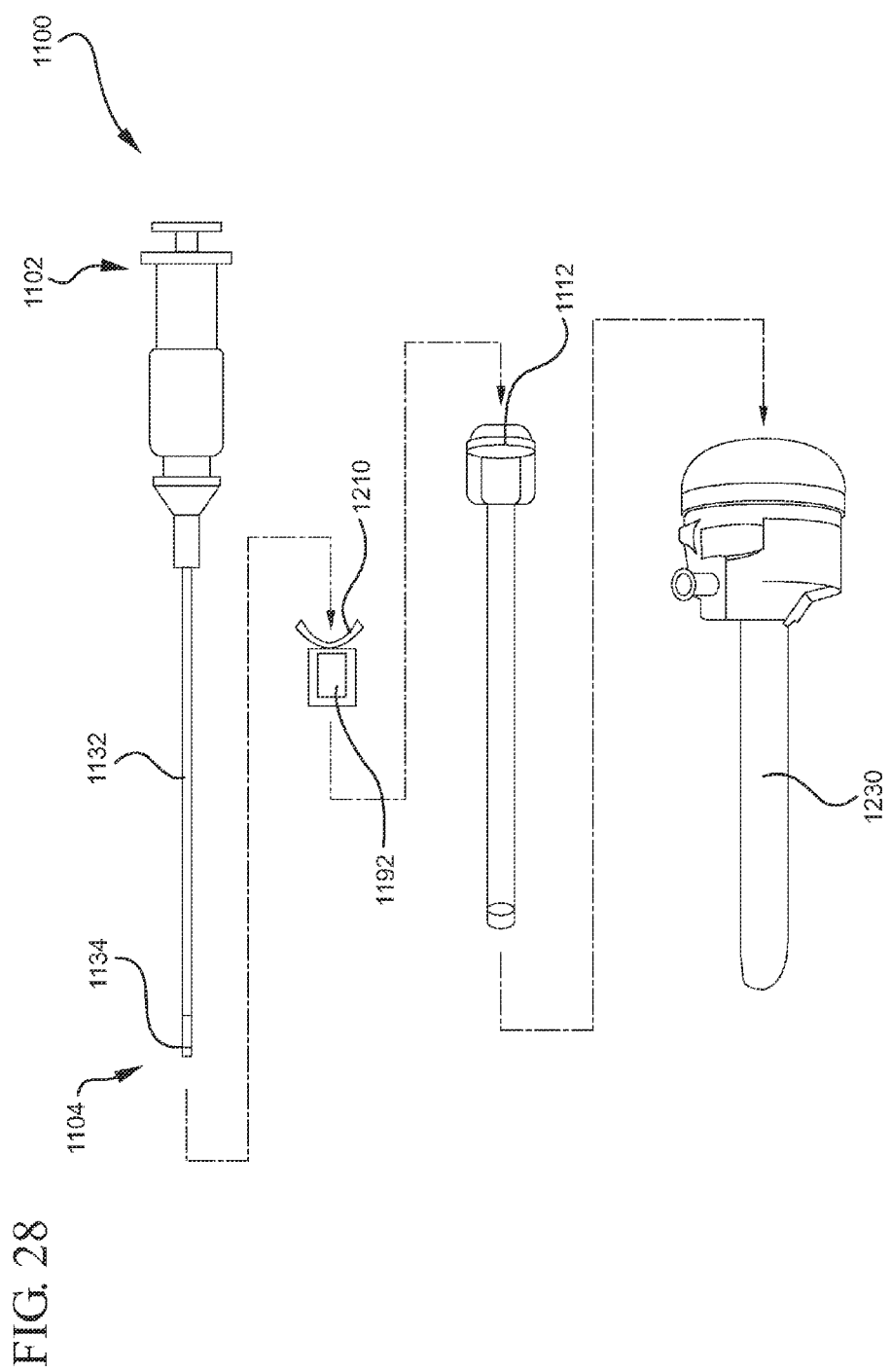
FIG. 28 shows a system for the delivery, deployment, and tamponade of a hemostat including an applicator instrument, a cartridge, an outer tube, and a trocar, in accordance with one embodiment of the present invention.

FIG. 28 shows a system for the delivery, deployment, and tamponade of a hemostat, in accordance with one embodiment of the present invention. The system may include one or more of the structural features and/or functions of the applicator instrument described above in FIGS. 1-27M. The system desirably includes an applicator instrument 1100 having a proximal end 1102, a distal end 1104, an intermediate shaft 1132, and an inner shaft 1134. The applicator instrument includes an inflatable balloon having one end secured to the intermediate shaft and one end secure to the inner shaft. The intermediate and inner shafts may be moved relative to one another for changing the shape of an inflated balloon. The system includes a cartridge 1192 that is adapted to receive a hemostat 1210. The system also has an outer tube 1112, and a trocar 1230.

Figure 29C:
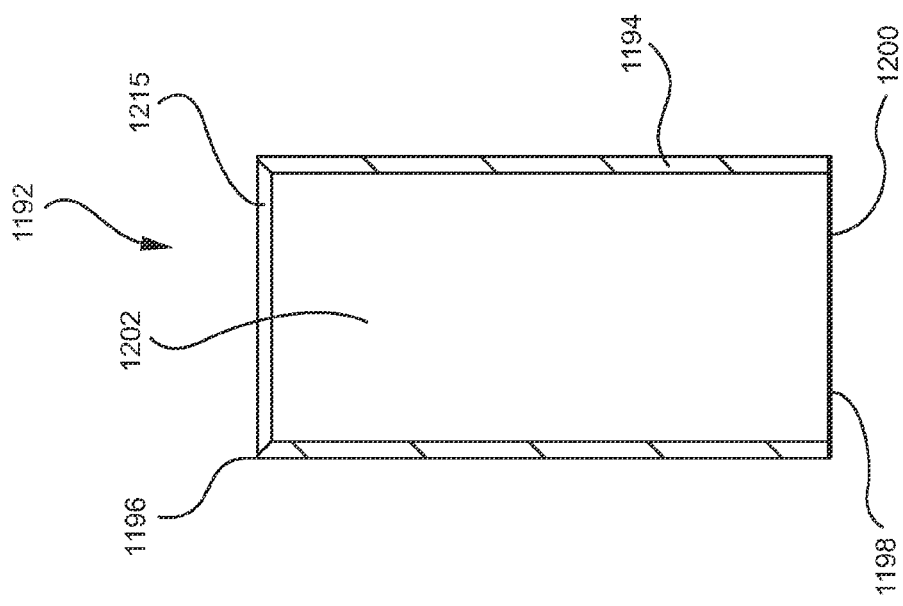
FIGS. 29A-29C show the cartridge of FIG. 28.
Figure 29B:
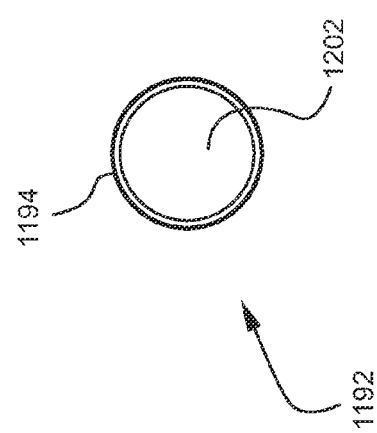
Figure 29A:
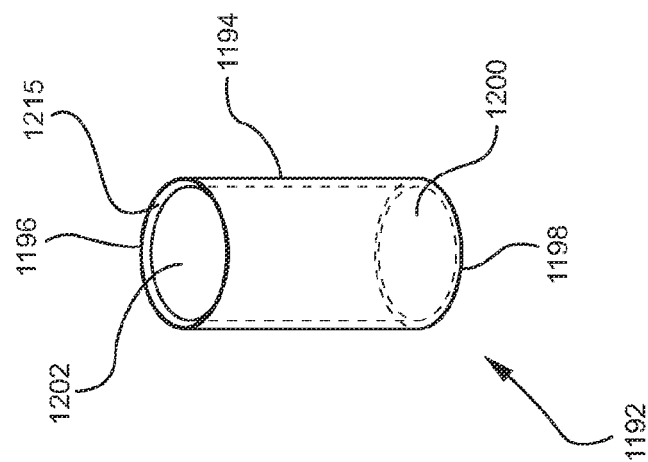

Referring to FIGS. 29A-29C, the cartridge 1192 for the system includes a cartridge tube 1194 having a proximal end 1196, a distal end 1198, a central opening 1202 extending between the proximal and distal ends, and a fluid-resistant or moisture impermeable seal 1200 covering the central opening 1202 at the distal end 1198 of the cartridge tube 1194. As shown in FIGS. 29A and 29B, the proximal end 1196 of the cartridge tube 1194 has a beveled edge 1215 that guides a hemostat patch into the central opening 1202 without snagging or damaging the hemostat patch on an edge of the cartridge.

Figure 30A:
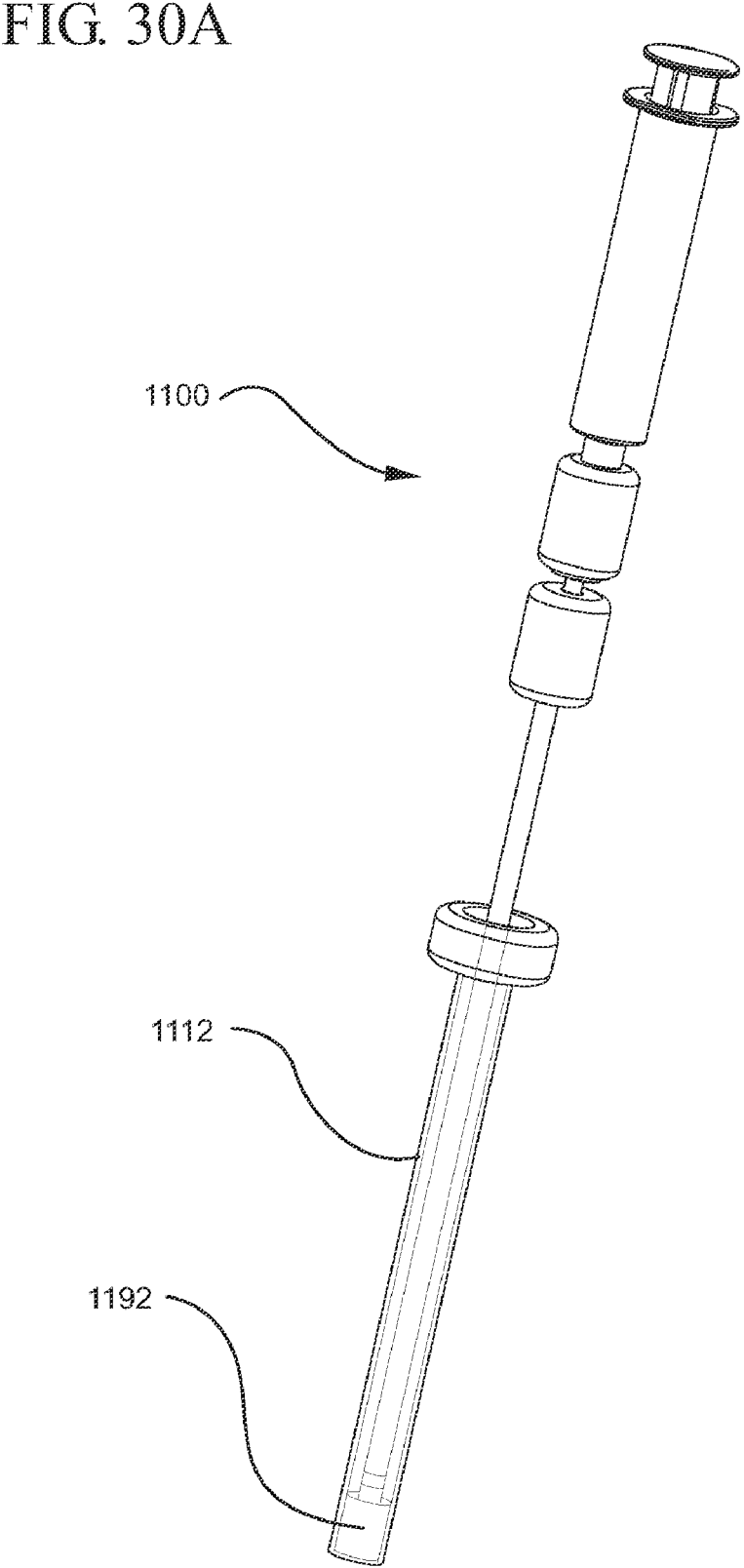
FIGS. 30A and 30B show a distal end of the applicator instrument of FIG. 28 being inserted into the outer tube of FIG. 28.
Figure 30B:
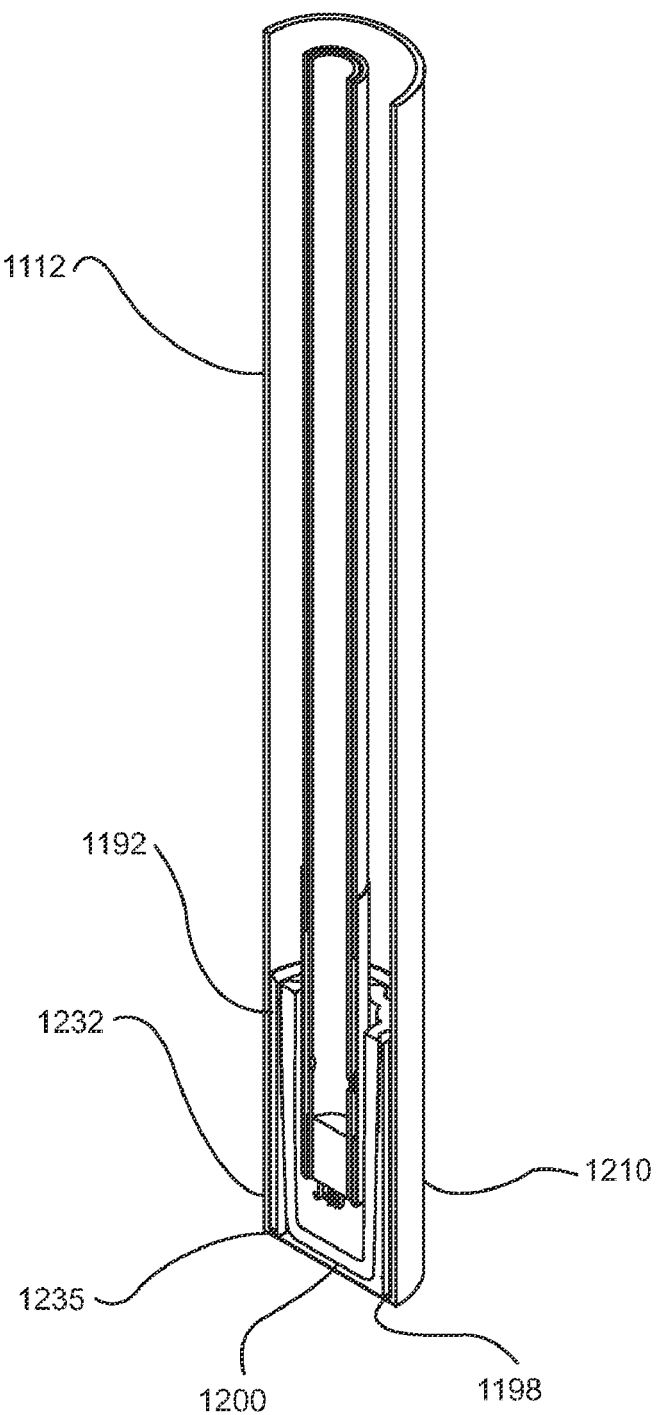

Referring to FIGS. 30A and 30B, after the hemostat has been loaded into the cartridge 1192 by the distal tip of the instrument 1100, the loaded cartridge is passed through the outer tube 1112. When the cartridge 1192 reaches the distal end 1232 of the outer tube 1112, the distal end 1198 of the cartridge 1192 engages a cartridge stop feature 1235 provided at the distal end 1232 of the outer tube 1112. After the cartridge 1192 has been positioned as shown in FIG. 30B, the fluid-resistant seal 1200 on the cartridge remains in place for preventing moisture from reaching the hemostat patch 1210 contained within the cartridge 1192.

Figure 31A:
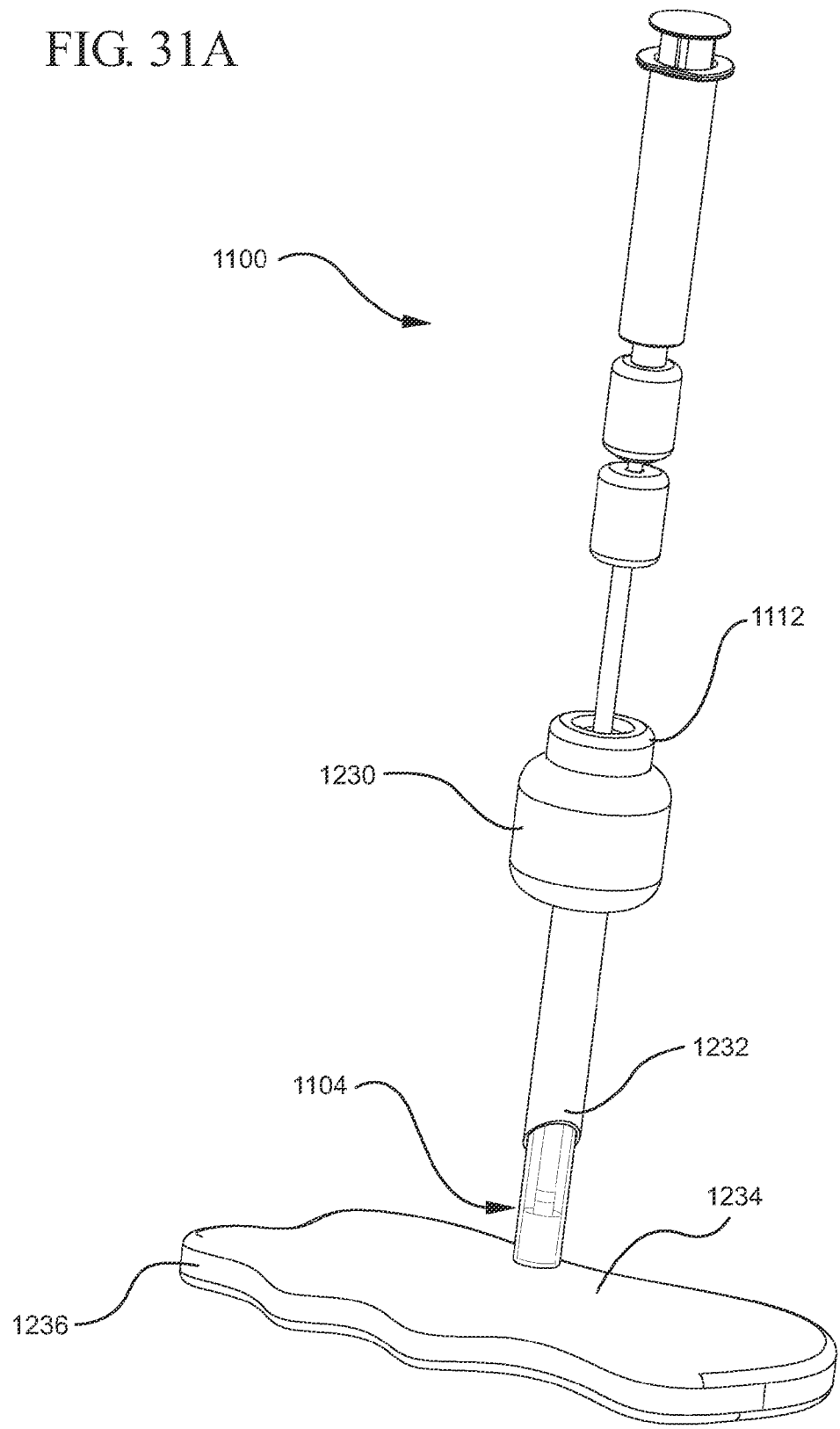
FIGS. 31A-31B show the delivery of a hemostat to a surgical site, in accordance with one embodiment of the present invention.
Figure 31B:
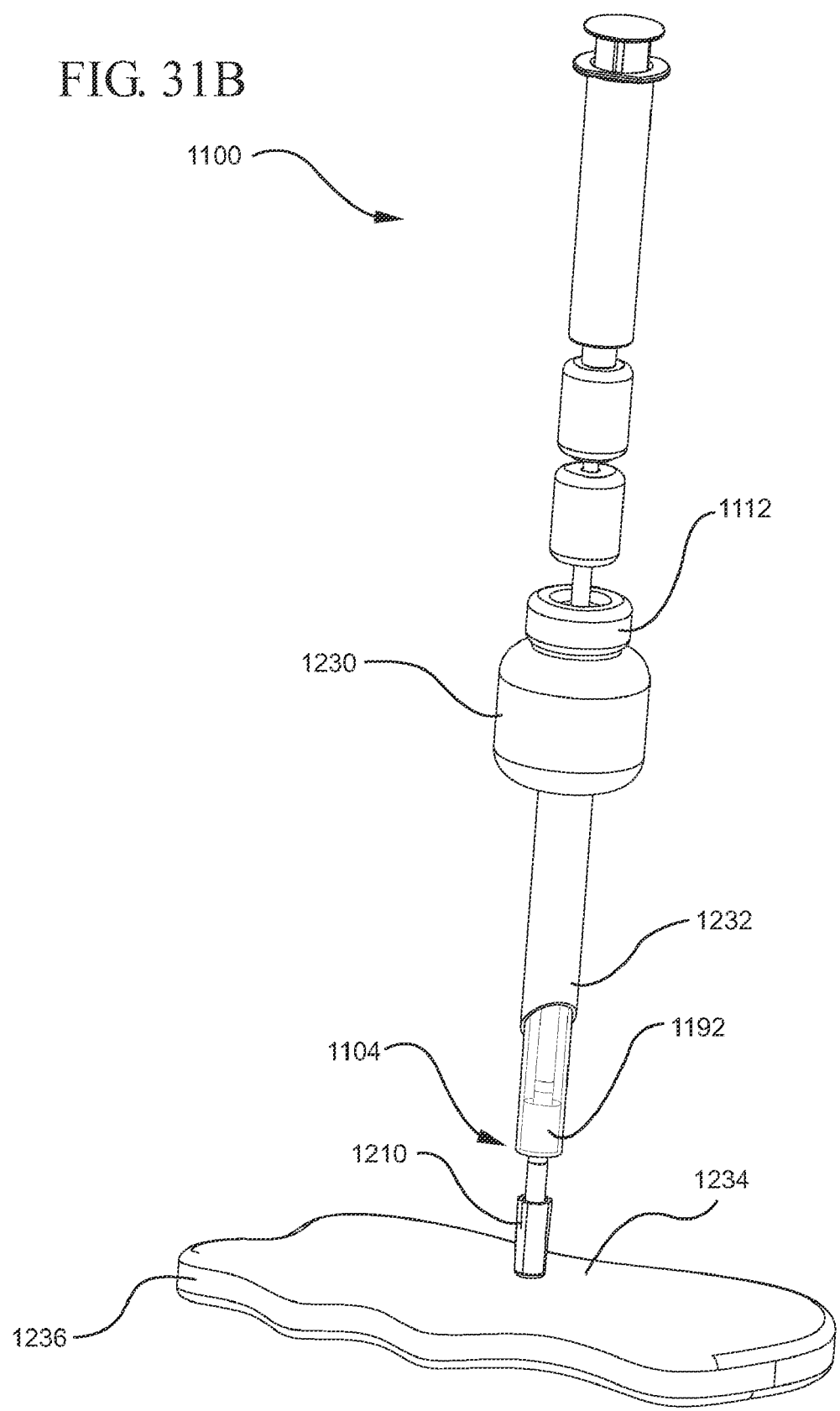

Referring to FIGS. 31A and 31B, the distal end 1104 of the instrument 1100 is advanced to a target location 1234 on tissue 1236 through a trocar tube 1230. The distal tip of the instrument 1100 is then advanced through the distal end 1232 of the trocar 1230. Referring to FIG. 31B, as the distal tip 1104 of the instrument 1100 is advanced further, the seal at the distal end of the cartridge 1192 is pierced and the hemostat 1210 is delivered to the desired site 1234 on the tissue 1236. A balloon provided at the distal end 1104 of the instrument 1100 may be inflated for deploying and tamponading the hemostat 1210 onto the tissue as described above.

Figure 32A:
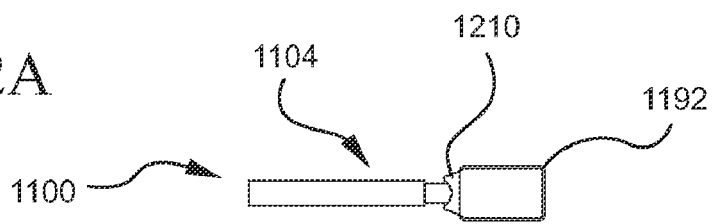
FIGS. 32A-32C show a method of advancing a hemostat through a fluid-resistant seal of a cartridge, in accordance with one embodiment of the present invention.
Figure 32B:
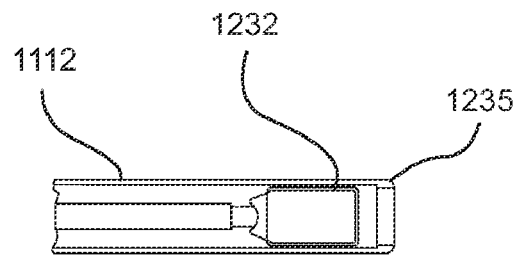
Figure 32C:
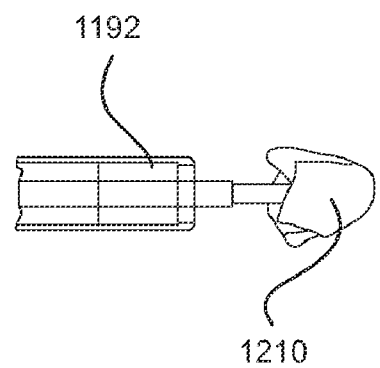

FIG. 32A shows the hemostat 1210 provided at the distal end 1104 of the instrument 1100 and loaded within the cartridge 1192. Referring to FIG. 32B, the loaded cartridge and the distal tip of the applicator instrument are then advanced toward the distal end of the outer tube 1112 until the distal end of the cartridge engages the cartridge stop feature 1235 provided at the distal end 1232 of the outer tube 1112. Referring to FIG. 32C, the instrument and the hemostat 1210 is then further advanced distally so as to pierce the fluid-resistant seal 1200 at the distal end of the cartridge 1192 for delivering the hemostat 1210 to a target site.

The present invention may be used to deliver, deploy and tamponade hemostats and medical textiles such as meshes, hemostats, adhesion prevention barriers, sponges, Surgicel Interceed, and Surgicel Nu-Knit. The present invention may also be used for the delivery, deployment and tamponade of other topically applied hemostats (TAH). The present invention preferably includes applicator instruments that protect the hemostats from exposure to fluids and moisture until the hemostats are deployed onto target tissue.

In one embodiment, the present invention provides an applicator instrument that includes an inflatable balloon that is used to endoscopically deploy and tamponade a textile or sponge form of hemostat. In one embodiment, the deflated balloon is tubular and is attached at each end to one of two pieces of concentric tubing such that one balloon end is movable and the balloon's shape is changeable from spherical to toroidal. The balloon's attachment at its distal end is such that the balloon is inverted over itself. When the balloon is inflated, the attachment of the distal end of the balloon to the distal end of the device is inside the inflated balloon.

In one embodiment, a cartridge has a fluid-resistant seal at the distal end thereof that protects the hemostats from moisture until the hemostats are applied to tissue. Barbed or Velcro®-like hooks may be incorporated at the distal end of the applicator instrument for engaging the hemostats and/or loading the hemostats into a cartridge. In one embodiment, the barbs or hooks preferably engage the fibers of the hemostat to hold the hemostat to the distal end of the instrument. In one embodiment, a system may include an applicator instrument, multiple cartridges, and a cartridge loader for aligning hemostats such as topically applied hemostats with the cartridges.

In one embodiment, an applicator instrument and cartridge protects topically applied hemostats from exposure to the environment such as exposure to moisture until the hemostat is applied to the target tissue. Preventing moisture from contacting the hemostat patch prevents premature activation of any medical components applied on the patch. The present invention also prevents the loss of patches attached to the distal end of an applicator instrument before the patches are applied to the target tissue. This feature may be particularly important for hemostat patches that are relatively expensive such as hemostats including human thrombin or fibrinogen.

In one embodiment, the present invention enables the shape of an inflated balloon to be changed so as to maximize the surface area available for selectively applying tamponade pressure to a medical patch. Thus, the present invention enables an increased balloon surface area to be applied to a medical patch. This may be particularly useful for applying pressure on hemostatic dressings.

While the foregoing is directed to embodiments of the present invention, other and further embodiments of the invention may be devised without departing from the basic scope thereof.

What is claimed is:

1. An instrument for delivering a hemostat comprising:
an outer shaft having a proximal end and a distal end;
a balloon disposed at the distal end of said outer shaft;
a hemostat disposed distal to the distal end of said outer shaft and distal to said balloon; and
a fluid-resistant element connected to and extending distally from the distal end of said outer shaft and surrounding said balloon and said hemostat, said fluid-resistant element having a breakable, fluid-resistant seal at a distal end thereof, wherein said outer shaft and said fluid resistant element connected to the distal end of said outer shaft slide together, axially toward a proximal end of said instrument and relative to said hemostat for delivering said balloon and said hemostat through said fluid-resistant seal.

2. The instrument as claimed in claim 1, wherein said breakable, fluid-resistant seal is selected from the group consisting of a pierceable membrane, a rubber seal, a slit valve, a cross-slit valve with two or more intersecting slits, a duckbill check valve, and a multi-faceted cross-slit check valve.

3. The instrument as claimed in claim 1, wherein said fluid-resistant element is detachably connected to the distal end of said outer shaft.

4. The instrument as claimed in claim 1, wherein said fluid-resistant element comprises a cartridge having the breakable, fluid-resistant seal at the distal end thereof.

5. The instrument as claimed in claim 4, wherein said cartridge comprises:
a cartridge tube having a proximal end, a distal end, and a central opening extending between the proximal and distal ends thereof; and
said breakable, fluid-resistant seal covering the central opening at the distal end of said cartridge tube.

6. The instrument as claimed in claim 5, wherein said cartridge tube has structure for connecting with the distal end of said outer shaft.

7. The instrument as claimed in claim 6, wherein said structure is selected from the group consisting of a ridge, a projection, a bump, a groove, a depression, a press-fit, and a thread.

8. The instrument as claimed in claim 1, further comprising:
said outer shaft having a central lumen extending to the distal end thereof;
an intermediate shaft telescopically received within the central lumen of said outer shaft, said intermediate shaft having a proximal end, a distal end that extends distally from the distal end of said outer shaft, and a central lumen extending to the distal end thereof;
a first actuator coupled with said outer shaft for selectively sliding said outer shaft axially relative to said intermediate shaft;
an inner shaft telescopically received within the central lumen of said intermediate shaft, said inner shaft having a proximal end and a distal end that extends distally from said intermediate shaft;
said balloon having a proximal end secured to the distal end of said intermediate shaft and a distal end secured to the distal end of said inner shaft, wherein said hemostat is distal to the distal end of said inner shaft and said fluid-resistant element is connected to the distal end of said outer shaft for forming a fluid-resistant chamber around said balloon and said hemostat.

9. The instrument as claimed in claim 8, wherein said first actuator is coupled with said outer shaft for selectively moving the distal end of said outer shaft and said fluid-resistant element proximally for breaking the fluid-resistant seal and delivering said hemostat from the distal end of said instrument.

10. The instrument as claimed in claim 9, further comprising:
a second actuator for inflating said balloon; and
a third actuator for moving the distal ends of said intermediate and inner shafts relative to one another for changing the shape of said inflated balloon.

11. The instrument as claimed in claim 8, wherein the distal end of said balloon is inverted and the inverted distal end of said balloon is secured to the distal end of said inner shaft.

12. The instrument as claimed in claim 5, further comprising a cartridge loader having an upper end with a platform, and a central opening extending from the platform toward a closed lower end of said cartridge loader, said cartridge tube being inserted into the central opening of said cartridge loader so that said breakable, fluid-resistant seal covering the distal end of said cartridge tube engages said closed lower end of said cartridge loader, and said hemostat is a hemostat patch positioned atop said platform, wherein said hemostat patch is aligned with the central opening of said cartridge loader for loading said hemostat patch into said cartridge tube.

13. The instrument as claimed in claim 12, wherein the closed lower end of said cartridge tube has a support surface that conforms to the fluid-resistant seal at the distal end of said cartridge tube.

14. An instrument for controlling bleeding comprising:
an outer shaft having a proximal end, a distal end, and a central lumen extending to the distal end thereof;
an intermediate shaft telescopically received within the central lumen of said outer shaft, said intermediate shaft having a proximal end, a distal end, and a central lumen extending to the distal end thereof;
a first actuator coupled with said outer shaft for sliding said outer shaft axially relative to said intermediate shaft;
an inner shaft telescopically received within the central lumen of said intermediate shaft, said inner shaft having a proximal end and a distal end that extends distally from said intermediate shaft;
a hemostat disposed distal to the distal end of said inner shaft and distal to the distal end of said outer shaft;
a fluid-resistant element connected to and extending distally from the distal end of said outer shaft and surrounding said hemostat, wherein said fluid-resistant element comprises a breakable, fluid-resistant seal at a distal end thereof, and wherein said outer shaft and said fluid-resistant element connected to the distal end of said outer shaft slide together, axially toward the proximal end of said instrument and relative to said intermediate shaft, said inner shaft and said hemostat for passing said hemostat through said fluid-resistant seal.

15. The instrument as claimed in claim 14, wherein said first actuator slides the distal end of said outer shaft and said fluid-resistant element in a proximal direction relative to said hemostat for breaking said fluid-resistant seal and delivering said hemostat.

16. The instrument as claimed in claim 15, further comprising:
a balloon having a proximal end secured to said intermediate shaft and a distal end secured to said inner shaft, wherein said hemostat overlies said balloon; and
a second actuator for inflating said balloon.

17. The instrument as claimed in claim 16, further comprising a third actuator for moving the distal ends of said intermediate and inner shafts relative to one another for changing the shape of said inflated balloon.

18. The instrument as claimed in claim 14, wherein at least one of said intermediate and inner shafts has an opening for introducing fluid into said balloon.

19. An instrument for controlling bleeding comprising:
an outer shaft having a proximal end and a distal end;
a balloon disposed at the distal end of said outer shaft;
a hemostat disposed adjacent said balloon and distal to the distal end of said outer shaft; and
a fluid-resistant element secured to and extending distally from the distal end of said outer shaft and surrounding said hemostat to form a fluid-resistant compartment around said hemostat, wherein said fluid-resistant element has a breakable, fluid-resistant seal at a distal end thereof, and wherein said outer shaft and said fluid-resistant element secured to the distal end of said outer shaft slide together, axially toward a proximal end of said instrument and relative to said balloon and said hemostat for delivering said hemostat through said fluid-resistant seal.

20. The instrument as claimed in claim 19, further comprising a first actuator coupled with said outer shaft for moving said outer shaft and said fluid-resistant element secured to the distal end of said outer shaft in a proximal direction for advancing said hemostat through said breakable, fluid-resistant seal.

21. The instrument as claimed in claim 20, further comprising:
a second actuator for inflating said balloon; and
a third actuator for changing the shape of said inflated balloon.

22. The instrument as claimed in claim 21, further comprising:
said outer shaft having a central lumen extending to the distal end thereof;
an intermediate shaft telescopically received within the central lumen of said outer shaft, said intermediate shaft having a proximal end, a distal end that extends distally from the distal end of said outer shaft, and a central lumen extending to the distal end thereof;
an inner shaft telescopically received within the central lumen of said intermediate shaft, said inner shaft having a proximal end and a distal end that extends distally from said intermediate shaft; and
said balloon having a proximal end secured to the distal end of said intermediate shaft and a distal end secured to the distal end of said inner shaft.

23. The instrument as claimed in claim 22, wherein said second actuator is coupled with at least one of said intermediate and inner shafts for moving the distal ends of said intermediate and inner shafts relative to one another for changing the shape of said balloon.

24. The instrument as claimed in claim 22, wherein the distal end of said balloon is inverted and the inverted distal end of said balloon is secured to the distal end of said inner shaft.

25. The instrument as claimed in claim 1, wherein said hemostat is selected from the group consisting of medical textiles, flowable hemostats and flowable sealants.

26. The instrument as claimed in claim 14, wherein said hemostat is selected from the group consisting of medical textiles, flowable hemostats and flowable sealants.

27. The instrument as claimed in claim 19, wherein said hemostat is selected from the group consisting of medical textiles, flowable hemostats and flowable sealants.

* * * * *